(12) United States Patent
Tarleton et al.

(10) Patent No.: US 7,888,135 B2
(45) Date of Patent: Feb. 15, 2011

(54) DIAGNOSTIC ASSAY FOR TRYPANOSOMA CRUZI INFECTION

(75) Inventors: Rick L. Tarleton, Watkinsville, GA (US); Ronald D. Etheridge, Jr., Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 554 days.

(21) Appl. No.: 11/587,283

(22) PCT Filed: Apr. 22, 2005

(86) PCT No.: PCT/US2005/013777
§ 371 (c)(1),
(2), (4) Date: Aug. 2, 2007

(87) PCT Pub. No.: WO2005/111622
PCT Pub. Date: Nov. 24, 2005

(65) Prior Publication Data
US 2008/0019995 A1    Jan. 24, 2008

Related U.S. Application Data

(60) Provisional application No. 60/564,804, filed on Apr. 23, 2004, provisional application No. 60/623,299, filed on Oct. 29, 2004.

(51) Int. Cl.
*G01N 33/53*    (2006.01)
(52) U.S. Cl. .................................. 436/518; 436/523
(58) Field of Classification Search ................ None
See application file for complete search history.

(56) References Cited

U.S. PATENT DOCUMENTS

| | | | |
|---|---|---|---|
| 5,232,844 | A | 8/1993 | Horowitz et al. |
| 5,756,662 | A | 5/1998 | Reed |
| 6,368,827 | B1 | 4/2002 | Tarleton et al. |
| 6,403,103 | B1 | 6/2002 | Paranhos-Baccala et al. |
| 6,419,933 | B1 | 7/2002 | Reed et al. |
| 6,875,584 | B1 | 4/2005 | Tarleton et al. |
| 2004/0241729 | A1 | 12/2004 | Liew |
| 2005/0158347 | A1 | 7/2005 | Tarleton et al. |
| 2005/0244505 | A1 | 11/2005 | Higbee et al. |
| 2006/0228300 | A1 | 10/2006 | Chang et al. |

FOREIGN PATENT DOCUMENTS

WO    WO 2005/111622 A2    11/2005

OTHER PUBLICATIONS

Luhrs et al. (Vaccine, 21:3058-3069, 2003).*
Mezzasoma et al. (Clin. Chem., 48:121-130, Jan. 2002).*
He et al. (Clin. Diag. Lab. Immunol., 7:899-903, 2000).*
Atwood et al., "The *Trypanosoma cruzi* proteome," *Science*, 2005, 309(5733):473-476.
Bio-Plex System and Suspension Array Technology. Bio-Rad Laboratories. Available online [retrieved Apr. 18, 2005]. Retrieved from the Internet: <http://www.biorad.com/B2B/BioRad/product/br_category.jsp?BV_SessionID=@@@@0429302147. 1179497201@@@@&BV_EngineID= ccchaddkmhhmfjkcfngcfkmdhkkdflm.0&categoryPath= %2fCatalogs%2fLife+Science+Research%2fMultiplex+ Suspension+Array+System%2fBio- Plex+System+and+Suspension+Array+Technology&catLevel= 4&divName=Corporate&loggedIn=false&lang=English&country= HQ&catOID-24083&isPA=false&serviceLevel=Lit+Request>;    5 pgs.
Bio-Plex Workstation and Software. Bio-Rad Laboratories. Available online [retrieved Apr. 18, 2005]. Retrieved from the Internet: <http://www.biorad.com/B2B/BioRad/product/br_category. jsp?BV_SessionID=@@@@0429302147.1179497201@@@@& BV_EngineID=ccchaddlunfihmfjkcfngcflcmdhkkdflm.0&divName=Life+Science+Research&categoryPath=%2fCatalogs%2fLife+Science+Research%2fMultiplex+Suspension+Array+System%2fBio-Plex+Workstation+and+Software&loggedIn=false&lang—English    &catLevel=4&country= HQ&catOID=-24084&isPA=false&serviceLevel=Lit+Request>;    3 pgs.
da Silveira et al., "Chagas disease: recombinant *Trypanosoma cruzi* antigens for serological diagnosis," 2001, *Trends Parasitol.*, 17(6):286-291.
Dias et al., "The Evolution of Chagas Disease (American Trypanosomiasis) Control after 90 Years since Carlos Chagas Discovery," 1999, *Mem. Inst. Oswaldo Cruz*, 94:Supp1.1:103-121.
Donnelly et al., "DNA Vaccines," *Ann.Rev.Immunol.* 15:617-648, 1997.
Endresz et al., "Induction of human cytomegalovirus (HCMV)-glycoprotein B (gB)pspecific neutralizing antibody and phosphoprotein 65 (pp65)-specific cytotoxic T lymphocyte responses by naked DNA immunization," 1999, *Vaccine*, 17:50-58.
Etheridge and Tarleton "What is wrong with this test: A high throughput screening of *Trypanosoma cruzi* antigens for seroligical diagnosis." Poster. Woods Hole ImmunoParasitology Conference: Woods Hole, MA. Apr. 25-28, 2004. 1 page; Abstract printed in meeting program.
Ferreira et al., "Enzyme-Linked Immunosorbent Assay for Serological Diagnosis of Chagas' Disease Employing a *Trypanosoma cruzi* Recombinant Antigen that Consists of Four Different Peptides," 2001, *J. Clin.Micro.*, 39(12):4390-4395.
Fifis et al., "Size-Dependent Immunogenicity: Therapeutic and Protective Properties of Nano-Vaccines against Tumors," 2004, *J. Immunol.*, 173:3148-3154.
Fifis et al., "Short peptide sequences containing MHC Class I and/or Class II epitopes linked to nano-beads induce strong immunity and inhibition of growth of antigen-specific tumor challenge in mice," 2004, *Vaccine*, 23:258-266.

(Continued)

*Primary Examiner*—N. M Minnifield
*Assistant Examiner*—Brian J Gangle
(74) *Attorney, Agent, or Firm*—Mueting Raasch & Gebhardt, P.A.

(57) ABSTRACT

A sensitive, multicomponent diagnostic test for infection with *T. cruzi*, the causative agent of Chagas disease, including methods of making and methods of use. Also provided is a method for screening *T. cruzi* polypeptides to identify antigenic polypeptides for inclusion as components of the diagnostic test, as well as compositions containing antigenic *T. cruzi* polypeptides.

10 Claims, 9 Drawing Sheets

OTHER PUBLICATIONS

Gateway® Cloning. Premier Biosoft International TechNotes. Available online [retrieved Apr. 15, 2005]. Retreived from the Internet: <http://www.premierbiosoft.com/tech_notes/Gateway_Cloning.html>; 6 pgs.

Giovanni, "NIAID Genomics Initiatives," Internet Article 2004. Retrieved from http://www.niaid.nih.gov/dmid/genomes/brc/PDF/gen_init. , entire document.

Hoffman et al., "Toward clinical trials of DNA vaccines against malaria," 1997, *Immunol. Cell Biol*. 75:376-381.

Jones et al., "Synthetic oligodeoxynucleotides containing CpG motifs enhance immunogenicity of a peptide malaria vaccine in Aotus monkeys," 1999, *Vaccine*, 17:3065-3071.

Laucella et al., "Frequency of Interferon-γ-Producing T Cells Specific for *Trypanosoma cruzi* inversely correlates with disease severity in chronic human Chagas Disease," 2004, *J. Infect. Dis*. Mar. 1;189(5):909-918.

LeBorgne et al., "In Vivo Induction of Specific Cytotoxic T Lumphocytes in Mice and Rhesus Macaques Immunized with DNA Vector Encoding an HIV Epitope Fused with Hepatitis B Surface Antigen," 1998, *Virology*. 240:304-315.

Luchtan et al., "TcruziDB: an integrated *Trypanosoma cruzi* genome," Nucleic Acids, Res., vol. 32, 2004, pp. D344-D346.

McCluskie et al., "Route and Method of Delivery of DNA Vaccine Influence Immune Responses in Mice and Non-Human Primates," 1999, *Mol. Med*. 5287-5300.

MMWR Morb Mortal Wkly Report. Mar. 15, 2001:51(10):210-2.

"MultiSite Gateway® Three-Fragment Vector Construction Kit." Instruction Manuel. Invitrogen life technologies. Catalog No. 12537-023. Version C; updated Nov. 29, 2004. Available online [retrieved Apr. 15, 2005]. Retrieved from the Internet: <http://www.invitrogen.com/content/sfs/manuals/multisite_gateway_man.pdf>; 68 pgs.

Nakazawa et al., "Excretory-Secretory Antigens of *Trypanosoma cruzi* are Potentially Useful for Serodiagnosis of Chronic Chagas' Disease," 2001, *Clin. Diag. Lab. Immunol*., 8:1024-1027.

Salomone et al., "*Trypanosoma cruzi* in Persons without Serologic Evidence of Disease, Argentina," 2003, *Emerg. Infect. Dis*. Dec;9(12):1558-1562.

Schutze-Redelmeier et al., "Introduction of Exogenous Antigens into the MHC Class 1 Processing and Presentation Pathway by *Drosophila* Antennapedia Homeodomain Primes Cytotoxic T Cells in Vivo," 1996, *J. Immunol*. 157:650-655.

Schwarze et al., "In Vivo Protein Transduction: Delivery of a Biologically Active Protein into the Mouse," 1999, *Science*, 285:1569-1572.

Soen et al., "Detection and Characterization of Cellular Immune Responses Using Peptide-MHC Microarrays," 2003, *PloS. Biol*., 1:429-438.

Stone et al., "HLA-restricted epitope identification and detection of functional T cell responses by using MHC-peptide and costimulatory microarrays," 2005, *PNAS USA*, 102:3744-3749.

Tacket et al., "Phase 1 safety and immune response studies of a DNA vaccine encoding hepatitis B surface antigen delivered by a gene delivery device," 1999, *Vaccine*, 17:2826-2829.

"TcruziDB: An integrated *Trypanosoma cruzi* Genome Resource." Online Database [retrieved May 17, 2007]. Funded by the American Heart Association. Last updated Nov. 7, 2006. Retrieved from the Internet: <http://www.tcruzidb.org/tcruzidb/>:, 2 pgs.

TcruziDB Gene: Tc00.1047053506563.40 (old ID No. 6998.t00004). Encoding eta-tubulin, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506563.40>; 4 pgs.

TcruziDB Gene: Tc00.1047053411235.9 (old ID No. 11788.t00001). Encoding alpha-tubulin, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053411235.9>; 4 pgs.

TcruziDB Gene: Tc00.1047053508299.60 (old ID No. 5568.t00006). Encoding 60S ribosomal protein L2, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key—Tc00.1047053508299.60>; 4 pgs.

TcruziDB Gene: Tc00.1047053506529.460 (old ID No. 6986.t00046). Encoding hypothetical protein, conserved. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506529.460>; 4 pgs.

TcruziDB Gene: Tc00.1047053506529.360 (old ID No. 6986.t00036). Encoding Cytochrome C oxidase subunit IV, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506529.360>; 3 pgs.

TcruziDB Gene: Tc00.1047053506529.610 (old ID No. 6986.t00061). Encoding hypothetical protein. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506529.610>; 3 pgs.

TcruziDB Gene: Tc00.1047053510887.50 (old ID No. 6003.t00005). Encoding hypothetical protein, conserved. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053510887.50>; 4 pgs.

TcruziDB Gene: Tc00.1047053509775.40 (old ID No. 5781.t00004). Encoding iron superoxide dismutase, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key—Tc00.1047053509775.40>; 3 pgs.

TcruziDB Gene: Tc00.1047053503583.40 (old ID No. 4650.t00004). Encoding trans-splicing factor, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053503583.40>; 3 pgs.

TcruziDB Gene: Tc00.1047053506297.270 (old ID No. 6890.t00027). Encoding 60S ribosomal protein L28, putative. Available online [retrieved May 18, 2007]. Retrieved from the Internet: <http://www.tcruzidb.org/tcruzidb/showRecord.do?name—GeneRecordClasses.GeneRecordClass&project_id=&primary_key=Tc00.1047053506297.270>; 4 pgs.

TcruziDB Gene: Tc00.1047053508441.20 (old ID No. 7730.t00002). Encoding glycosomal phosphoenolpyruvate carboxykinase (Phosphoenolpyruvate Carboxylkinase 9Pepck)), putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053508441.20>; 4 pgs.

TcruziDB Gene: Tc00.1047053508355.250 (old ID No. 7695.t00025). Encoding 60S acidic ribosomal subunit protein, putative (Calmodulin-ubiquitin Associated Protein CUB2.8). Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053508355.250>; 4 pgs.

TcruziDB Gene: Tc00.1047053506391.30 (old ID No. 6925.t00003). Encoding ef-hand protein 5, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506391.30>; 3 pgs.

TcruziDB Gene: Tc00.1047053509617.20 (old ID No. 8152.t00002). Encoding paraflagellar rod protein 3, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053509617.20>; 4 pgs.

TcruziDB Gene: Tc00.1047053510955.40 (old ID No. 8553.t00004). Encoding axoneme central apparatus protein, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053510955.40>; 4 pgs.

TcruziDB Gene: Tc00.1047053509695.220 (old ID No. 8171.t00022). Encoding serine carboxypeptidase (CBP1), putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053509695.220>; 4 pgs.

TcruziDB Gene: Tc00.1047053511289.30 (old ID No. 8647.t00003). Encoding aminopeptidase, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053511289.30>; 4 pgs.

TcruziDB Gene: Tc00.1047053510163.20 (old ID No. 8322.t00002). Encoding elongation factor-1 gamma, putative. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053510163.20>; 4 pgs.

TcruziDB Gene: Tc00.1047053506531.20 (old ID No. 6987.t00002). Encoding hypothetical protein, conserved. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506531.20>; 5 pgs.

TcruziDB Gene: Tc00.1047053506489.30 (old ID No. 6967.t00003). Encoding hypothetical protein, conserved. Available online [retrieved May 18, 2007]. Retrieved from the Internet: <http://www.tcruzidb.org/tcruzidb/showRecord.do?name=GeneRecordClasses.GeneRecordClass&project_id=&primary_key=Tc00.1047053506489.30>; 3 pgs.

Umezawa et al., Evaluation of Recombinant Antigens for Serodiagnosis of Chagas' Disease in South and Central American, 1999, *J. Clin. Micro.*, 37:1554-1560.

Umezawa et al., "An improved serodiagnostic test for Chagas' disease employing a mixture of *Trypanosoma cruzi* recombinant antigens," 2003, *Transfusion*, 43:91-97.

Wang et al., "Simultaneous Induction of Multiple Antigen-Specific Cytotoxic T Lymphocytes in Nonhuman Primates by Immunization with a Mixture of Four Plasmodium falciparum DNA Plasmids," 1998, *Infect. Immun.* 66:4193-4202.

Wang et al., Induction of Antigen-Specific Cytotoxic T Lymphocytes in Humans by a Malaria DNA Vaccine, 1998, *Science*, 282(5388):476-480.

Cooley et al., "High Throughput Selection of Effective Serodiagnostics for *Trypanosoma cruzi* infection," 2008. PLOS. vol. 2, Issue 10, e316. pp. 1-12.

* cited by examiner

DIAGNOSTIC ASSAY FOR *TRYPANOSOMA CRUZI* INFECTION

CROSS-REFERENCE TO RELATED APPLICATIONS

This application claims the benefit of U.S. Provisional Application Ser. No. 60/564,804, filed 23 Apr. 2004, and U.S. Provisional Application Ser. No. 60/623,299, filed 29 Oct. 2004, both of which are incorporated herein by reference in their entirety.

STATEMENT OF GOVERNMENT RIGHTS

This invention was made with government support under Grant AI44979 awarded by the National Institutes of Health. The United States Government may have certain rights in the invention.

BACKGROUND OF THE INVENTION

*Trypanosoma cruzi* is an obligate intracellular protozoan parasite. In mammalian hosts *T. cruzi* cycles between a trypomastigote stage which circulates in the blood and the amastigote stage which replicates in the cytoplasm of infected host cells (primarily muscle).

*T. cruzi* is the etiological agent of Chagas disease and is ranked as the most serious parasitic disease in the Americas, with an economic impact far outranking the combined effects of other parasitic diseases such as malaria, schistosomiasis, and leishmania (Dias et al., Mem. Inst. Oswaldo Cruz, 1999, 94:Suppl.1:103). Chagas disease is prevalent in almost all Latin American countries including Mexico and Central America, where approximately 18 million people are infected with *T. cruzi* and roughly 50,000 children and adults die of chronic Chagas disease every year due to lack of effective treatments. More than 90 million are at risk of infection in endemic areas. Additionally, 2-5% of fetus carried by infected mothers in endemic areas are either aborted or born with congenital Chagas disease. Loss of revenue in terms of productivity lost due to sickness and medical costs have an overwhelming effect on economic growth of these countries.

Recently, due to migration and immigration trends, *T. cruzi* has spread beyond the borders of Latin America and has been detected in Europe, Asia, and the United States (Ferreira et al., J. Clin. Micro., 2001, 39:4390). In the U.S., 50-100 thousand serologically positive persons progressing to the chronic phase of Chagas disease are present, and the number of infected immigrants in developed countries is increasing. It is expected that, due to the exponential increase in emigration from Latin America, Chagas disease may become a serious health issue in North America and Europe in the next decade.

As a result of the increase in the number of infected individuals, the risk of transmission of *T. cruzi* to non-infected individuals through blood transfusion and organ transplants from the infected immigrant donors is emerging as a route of *T. cruzi* transmission in more developed nations (Umezawa et. al. J. Clin. Micro., 1999, 37:1554; Silveira et. al. Trends Parasitol., 2001, 17; Chagas disease after organ transplantation—United States, 2001; MMWR Morb Mortal Wkly Rep. 2002 Mar. 15; 51(10):210-2). Each year, 15 million units of blood are transfused and approximately 23,000 organ transplants are performed in the United States alone, and presently almost none of the blood supply is tested for *T. cruzi*. A few cases of infection by *T. cruzi* through organ donation have already been reported to United States Centers for Disease Control since 2001. It has therefore become apparent that the screening of blood and organ donors is necessary not only in Latin America but also in developed countries that receive immigrants from endemic areas.

The most widely accepted serological tests for *T. cruzi* infection utilize antigens from either whole to semi-purified parasite lysates from epimastigotes that react with anti-*T. cruzi* IgG antibodies. These tests show a degree of variability due to a lack of standardization of procedures and reagents between laboratories, and a number of inconclusive and false positive results occur due to cross-reactivity with antibodies developed against other parasites (Nakazawa et. al. Clin. Diag. Lab. Immunol., 2001, 8:1024). Others report positive PCR and clinical disease in patients with negative serology. Salomone, et al. Emerg Infect Dis. 2003 December; 9(12): 1558-62. A diagnostic test that is able to reduce the rate of false-positives while simultaneously enhancing sensitivity is urgently needed.

SUMMARY OF THE INVENTION

The present invention provides new tools for diagnosing and treating *T. cruzi* infections in people and animals. In one aspect, the invention provides a method of screening for antigenic *T. cruzi* polypeptides. First and second substrates are provided that each include a plurality of individually addressable candidate antigens derived from *T. cruzi*. The antigens present on the first and second substrate are substantially the same in order to facilitate comparison. The candidate antigens of the first substrate are contacted with a body fluid of a first mammal known to be positive for *T. cruzi* infection. The candidate antigens of the second substrate are contacted with a body fluid from a second mammal known or reasonably believed to be unexposed to *T. cruzi* infection. At least one antigenic *T. cruzi* polypeptide is then identified using a process in which the antigenic *T. cruzi* polypeptide binds to an antibody present in the body fluid of the first mammal but exhibits little or no binding to an antibody present in the body fluid of the second mammal. Optionally, the first and second mammals may be humans.

Positive evidence of *T. cruzi* infection in the first mammal may, for example, be based on a detection method such as a T cell assay, polymerase chain reaction (PCR), hemoculture or a xenodiagnostic technique. Evidence of negative serology in the second mammal is preferably shown by a negative result when the mammal is tested for *T. cruzi* infection utilizing a conventional serodiagnostic test that relies on antigens from whole or semi-purified parasite lysates from *T. cruzi*, such as, for example, from a *T. cruzi* epimastigote lysate.

More than two substrates that include a plurality of individually addressable candidate antigens may be used. Each substrate is contacted with the body fluid from a mammal which exhibits a different level of serological reaction to *T. cruzi* using a conventional serodiagnostic test that relies on antigens from whole or semi-purified parasite lysates from *T. cruzi*. The method optionally further includes the step of preparing the polypeptide antigens from an expression vector including a nucleotide sequence from *T. cruzi*.

Optionally, the screening method may further include a preliminary screening step. The preliminary screening step includes providing a first and a second substrate comprising a plurality of individually addressable antigen pools derived from *T. cruzi* in which the antigen pools present on the first and second substrate are substantially the same. The first substrate is contacted with a body fluid of a first mammal known to be positive for *T. cruzi* infection and the second substrate is contacted with a body fluid from a second mammal known or reasonably believed to be unexposed to *T. cruzi* infection. An antigen pool is then identified that binds to an antibody present in the body fluid of the first mammal but exhibits little or no binding to an antibody present in the body fluid of the second mammal.

In another aspect, the present invention provides an article that includes a substrate and a plurality of individually addressable antigenic *T. cruzi* polypeptides. The antigenic peptides can be selected from the polypeptides identified in Table 1, and include antigenic analogs or subunits thereof. The polypeptides are immobilized onto a surface of the substrate. Optionally, the article may include at least one antigenic *T. cruzi* polypeptide identified according to the screening method described above, or antigenic analogs or subunits thereof, immobilized onto the surface of the substrate. In embodiment, the polypeptides are immobilized on the substrate surface to form a microarray. In another embodiment, the substrate includes at least one nanoparticle, with the polypeptides being immobilized on the surface of the nanoparticle.

The present invention also provides a kit for diagnosis of *T. cruzi* infection that includes an article that includes a substrate and a plurality of individually addressable antigenic *T. cruzi* polypeptides selected from the polypeptides identified in Table 1, in which the polypeptides are immobilized onto a surface of the substrate. The kit also includes packaging materials and instructions for use. Optionally, the kit may include at least on antigenic *T. cruzi* polypeptide identified by the screening method described above and immobilized onto the surface of the substrate. The kit may be formulated for medical or veterinary use.

The present invention also provides a method for obtaining information about a known or suspected *T. cruzi* infection in a mammal, or for determining whether a mammal is or has been infected by *T. cruzi*. Execution of the method involves obtaining a biological sample from the mammal, contacting the biological sample with an article that includes a substrate and a plurality of individually addressable antigenic *T. cruzi* polypeptides selected from the polypeptides identified in Table 1, or antigenic analogs or subunits thereof, in which the polypeptides are immobilized onto a surface of said substrate, and evaluating the presence, absence, intensity or pattern of interaction of components of the biological sample with the immobilized antigenic *T. cruzi* polypeptides. Information that can be obtained according to the method includes, for example, the presence or absence of *T. cruzi* infection, the identity of the infective strain, the length of the infection, the stage of the infection, whether the infection is still present or the mammal has been cured, the vaccination status of the mammal, the success of treatment, or any combination thereof. Optionally, the article includes at least one antigenic *T. cruzi* polypeptide identified according to the described screening method, or antigenic analogs or subunits thereof, that are immobilized onto the surface of the substrate. The method can, for example, be a serodiagnostic method, wherein the biological sample component that interacts with an immobilized antigenic *T. cruzi* polypeptide is an antibody from the mammal. Alternatively, the method may be embodied by a cellular assay method where the biological sample component that interacts with an immobilized antigenic *T. cruzi* polypeptide is T cell from the mammal. The method can be implemented as a multiplexed assay in which the biological sample is contacted simultaneously with the plurality of antigenic *T. cruzi* polypeptides. The biological sample can, for example, be obtained from a person suspected of having or being exposed to disease, or obtained from an actual or potential blood donor or transplant donor. Alternatively, the biological sample is obtained from a pooled blood product supply intended for use in transfusions or research.

In another aspect, the present invention provides a method for detecting contamination of a blood product supply with *T. cruzi*. The method of detecting contamination includes selecting a sample from the blood supply, contacting the sample with an article that includes a substrate and a plurality of individually addressable antigenic *T. cruzi* polypeptides selected from the polypeptides identified in Table 1, or antigenic analogs or subunits thereof, in which the polypeptides are immobilized onto a surface of said substrate, and evaluating the presence, absence, intensity or pattern of interaction of components of the sample with the immobilized antigenic *T. cruzi* polypeptides to determine whether the blood supply is contaminated with *T. cruzi*. The article may include at least one antigenic *T. cruzi* polypeptide identified according to the described screening method, or antigenic analogs or subunits thereof, and immobilized onto the surface of said substrate.

Blood products that can be tested include whole blood, a blood product, or a blood fraction. For example, a cellular blood component, a liquid blood component, a blood protein, or mixtures thereof, or a red blood cell concentrate, a leukocyte concentrate, a platelet concentrate, plasma, serum, a clotting factor, an enzymes, albumin, plasminogen, or a immunoglobulin, or mixtures of thereof, can be tested for contamination according to the method.

The method of detecting contamination can be a serodiagnostic method, wherein the sample component that interacts with an immobilized antigenic *T. cruzi* polypeptide is an antibody. Alternatively, the method can take the form of a cellular assay method, wherein the sample component that interacts with an immobilized antigenic *T. cruzi* polypeptide is T cell.

In yet another aspect, the present invention provides a multicomponent vaccine. In one embodiment, the vaccine includes a plurality of immunogenic *T. cruzi* polypeptides selected from the *T. cruzi* polypeptides listed in Table 1, or immunogenic subunits or analogs thereof. Embodiments of the multicomponent vaccine include having at least one immunogenic *T. cruzi* polypeptide identified according to the described screening method, or immunogenic subunit or analog thereof. In another embodiment, the multicomponent vaccine that includes a plurality of nucleotide sequences, where each nucleotide sequence encoding an immunogenic *T. cruzi* polypeptide selected from the *T. cruzi* polypeptides listed in Table 1, or immunogenic subunits or analogs thereof. In embodiments of the multicomponent vaccine includes a plurality of nucleotide sequences, the immunogenic *T. cruzi* polypeptide includes polypeptides identified according to the screening method, or immunogenic subunit or analog thereof. The multicomponent vaccine may be a therapeutic or prophylactic vaccine.

BRIEF DESCRIPTION OF THE DRAWINGS

FIG. 6 shows testing of four different serum samples using a panel of serodiagnostic proteins; A, strong seropositive serum; B, Subject 58: T cell reactive/seronegative serum; C, Subject 44: T cell non-reactive/seronegative serum; D, Subject 60: T cell non-reactive/seronegative. From left to right, in each panel at each of the sera dilutions, the test proteins are: lysate control, ovalbumin, protein 3K-1, 3K-3, 1A-1 and 4A-3, and pool 3K. Subject 58, declared seronegative by standard serological assay but exhibiting T cell reactivity to *T. cruzi* antigens, is of particular interest because antibodies are detected that recognize the recombinant *T. cruzi* antigens but not the parasite lysate.

DETAILED DESCRIPTION OF ILLUSTRATIVE EMBODIMENTS

In one aspect, the present invention is directed to the detection of *T. cruzi* infection in a mammal, particularly a human. A plurality of *T. cruzi* polypeptides, or subunits or analogs thereof, that are detectable by antibodies present in a bodily fluid, such as blood, plasma or serum, of at least some individuals that are infected with *T. cruzi* are included in a multicomponent panel for use in a diagnostic assay, which may be a serodiagnostic assay or a cellular assay. The term "serodiagnostic" is used because the assay is typically performed on a blood component such as whole blood, plasma or serum, but it should be understood that any bodily fluid that may provide evidence of an immune response to *T. cruzi* can be assayed using the serodiagnostic test of the invention.

The panel components are contacted with a bodily fluid of an individual such as blood, plasma, serum, urine, saliva or tears and the like, and the presence of absence of evidence of an immune response to *T. cruzi* in the individual is evaluated. The body fluid that is tested can be that of an individual patient to be screened, or it can be a body fluid that is part of a blood or plasma supply, for example, pooled or unpooled, that is available for transfusion and/or research.

An immune response indicative of *T. cruzi* infection may be evidenced by the binding of antibodies in the biological fluid to panel components. The panel components can likewise be used to assess the presence of a T cell response in the subject.

In a preferred embodiment, the diagnostic test is highly specific for *T. cruzi* infection and sufficiently sensitive to detect infection in subjects considered negative with conventional serological assays based on *T. cruzi* lysates due to a poor or inconsistent B cell response to infection. Optionally the test can include, as specificity controls, polypeptide antigens that are recognized when other infections are present.

The diagnostic test can detect the presence or absence of *T. cruzi* infection. In some embodiments, and depending on the antigenic polypeptides selected for including in the multicomponent panel, the pattern of antigen recognition may provide additional information such as the stage of infection or the severity of disease. The antigen recognition pattern may also be useful to discriminate among patients with active or latent infections, and those who have been cured or vaccinated.

The invention is applicable to human disease but also has veterinary applications. For example, a diagnostic assay developed according to the invention can be used to diagnose *T. cruzi* infection in farm animals or pets, such as dogs.

Antigenic Polypeptides

A *T. cruzi* polypeptide, or subunit or analog thereof, that is suitable for inclusion in the panel is one that reacts to antibodies in the sera of individuals infected with *T. cruzi*. Such a polypeptide is referred to herein as an antigenic polypeptide or a polypeptide antigen.

A preferred antigenic polypeptide, or antigenic subunit or analog thereof, is one that detectably binds antibodies in a bodily fluid of a subject who is known to be infected or to have been infected by *T. cruzi*, but whose bodily fluid is seronegative when assayed by conventional means. A bodily fluid that is seronegative when assayed by conventional means is one that, for example, does not show a positive reaction (antibody binding) when exposed to antigens from either whole or semi-purified parasite lysates, for example those from epimastigotes, in conventional diagnostic tests. A subject who shows evidence of *T. cruzi* infection using, for example, a T cell assay, polymerase chain reaction (PCR), hemoculture, or xenodiagonstic techniques, is considered to known to be infected or to have been infected by *T. cruzi*, even if the subject shows a negative response to a conventional serodiagnostic test.

Another preferred polypeptide, or subunit or analog thereof, is one that detectably binds antibodies in a bodily fluid of a subject who is seropositive when assayed by conventional means, regardless of whether the polypeptide also exhibits detectable binding to antibodies in a bodily fluid of a subject who is known to be infected or to have been infected by *T. cruzi*, but whose bodily fluid is seronegative when assayed by conventional means.

The antigenic *T. cruzi* polypeptides, and antigenic subunits and analogs thereof, bind antibodies in a bodily fluid of a subject, such as blood, plasma or sera, thereby providing evidence of exposure to *T. cruzi*. These antigenic polypeptides, and antigenic subunits and analogs thereof, may also be immunogenic; i.e., they may also, when delivered to a subject in an appropriate manner, cause an immune response (either humoral or cellular or both) in the subject. Immunogenic *T. cruzi* polypeptides, as well as immunogenic subunits and analogs thereof, are therefore expected to be useful in vaccines, as described below.

It should be understood that the term "polypeptide" as used herein refers to a polymer of amino acids and does not refer to a specific length of a polymer of amino acids. Thus, for example, the terms peptide, oligopeptide, and protein are included within the definition of polypeptide.

An antigenic *T. cruzi* polypeptide according to the invention is not limited to a naturally occurring antigenic *T. cruzi* polypeptide; it can include an antigenic subunit or antigenic analog of a *T. cruzi* polypeptide. Likewise the antigenic polypeptide can be a multivalent construct that includes epitopes obtained from different antigenic polypeptides of *T. cruzi*. An antigenic analog of an antigenic *T. cruzi* polypeptide is a polypeptide having one or more amino acid substitutions, insertions, or deletions relative to an antigenic *T. cruzi* polypeptide, such that antigenicity is not entirely eliminated. Substitutes for an amino acid are preferably conservative and are selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free—OH is maintained; and Gln for Asn to maintain a free $NH_2$. Antigenic subunits of an antigenic *T. cruzi* polypeptide are antigenic *T. cruzi* polypeptides that are truncated at either or both of the N-terminus or C-terminus, without eliminating their ability to detect serum antibodies against *T. cruzi*. Preferably, an antigenic subunit contains an epitope recognized by a host B cell or T cell. Fragments of an antigenic *T. cruzi* protein contain at least about eight amino acids, preferably at least about 12 amino acids, more preferably at least about 20 amino acids.

Figure 1C:
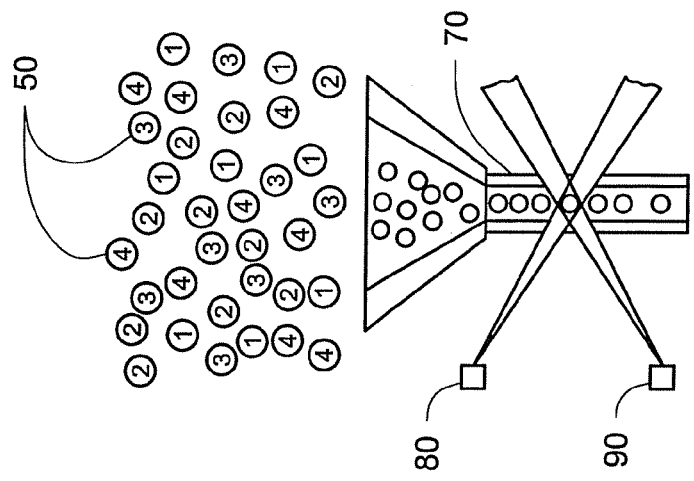
FIG. 1 provides a pictoral overview of the BIO-PLEX array analysis method;
A) shows the protein-antibody-microsphere complex used by the BIO-PLEX method,
B) shows multiple complexes in the well of a microplate substrate, and C) shows laser excitation of the complexes as they flow through a flow cytometer.

Examples of antigenic *T. cruzi* polypeptides suitable for inclusion in the multicomponent panel of the invention are listed in Table I. The "Gene ID Numbers" represent gene numbers assigned by annotators of the *T. cruzi* genome and are accessed via the *T. cruzi* genome database on the worldwide web at "TcruziDB.org".

other, with the antigenic *T. cruzi* polypeptides of Table I, and/or with other known antigens, in diagnostic and therapeutic applications relating to *T. cruzi* infection as described is also envisioned. It should be understood that the antigenic *T. cruzi* polypeptides described herein or identified using the screening method described herein are generally useful in any of diagnostic and/or therapeutic applications relating to *T. cruzi* infection.

Antigenic polypeptides used in the multicomponent panel of the invention preferably include polypeptides that are abundant during the two stages (amastigote and trypomastigote) that are prevalent in the life cycle of the parasite in mammals. In a mammalian host, *T. cruzi* cycles between a dividing intracellular stage (the amastigote) and a non-replicative extracellular trypomastigote form which circulates in the blood. The presence of two developmental stages of *T. cruzi* in mammalian hosts provides two anatomically and (to some degree) antigenically distinct targets of immune detection—the trypomastigotes in the bloodstream and the amastigotes in the cytoplasm of infected cells. The intracellular location of amastigotes of *T. cruzi* has long been considered a "hiding place" for the parasite wherein it is not susceptible to immune recognition and control. Notably, most current serological tests for *T. cruzi* are based upon antigens from epimastigotes, the form of *T. cruzi* present in insects but not humans. Thus, in a preferred embodiment, an antigenic polypeptide for use in a *T. cruzi* diagnostic test or vaccine according to the invention can be one that is expressed by *T. cruzi* in the extracellular (trypomastigote) stage, in the intracellular (amastigote) stage, or during both stages of the life cycle.

Diagnostic Method

The diagnostic of the invention utilizes a multicomponent panel to assess the presence of an immune response (e.g., the

TABLE I

Representative antigenic *T. cruzi* polypeptides

| Protein | Gene ID Numbers | SEQ ID NO |
|---|---|---|
| Tc beta-tubulin | 6998.t00004 | SEQ ID NO: 1 |
| Tc alpha tubulin | 11788.t00001 | SEQ ID NO: 2 |
| 60S ribosomal protein L2, putative | 5568.t00006 | SEQ ID NO: 3 |
| hypothetical protein, conserved | 6986.t00046 | SEQ ID NO: 4 |
| Cytochrome C oxidase subunit IV, putative | 6986.t00036 | SEQ ID NO: 5 |
| hypothetical protein | 6986.t00061 | SEQ ID NO: 6 |
| hypothetical protein, conserved | 6003.t00005 | SEQ ID NO: 7 |
| iron superoxide dismutase, putative | 5781.t00004 | SEQ ID NO: 8 |
| trans-splicing factor, putative | 4650.t00004 | SEQ ID NO: 9 |
| 60S ribosomal protein L28, putative | 6890.t00027 | SEQ ID NO: 10 |
| glycosomal phosphoenolpyruvate carboxykinase, putative (Phosphoenolpyruvate Carboxykinase (Pepck)) | 7730.t00002 | SEQ ID NO: 11 |
| ubiquitin-fusion protein, putative (polyubiquitin/ribosomal protein CEP52) | 7355.t00001 | SEQ ID NO: 12 |
| 60S acidic ribosomal subunit protein, putative (Calmodulin-ubiquitin associated protein CUB2.8) | 7695.t00025 | SEQ ID NO: 13 |
| ef-hand protein 5, putative | 6925.t00003 | SEQ ID NO: 14 |
| paraflagellar rod protein 3 | 8152.t00002 | SEQ ID NO: 15 |
| axoneme central apparatus protein, putative | 8553.t00004 | SEQ ID NO: 16 |
| serine carboxypeptidase (CBP1), putative | 8171.t00022 | SEQ ID NO: 17 |
| aminopeptidase, putative | 8647.t00003 | SEQ ID NO: 18 |
| elongation factor-1 gamma, putative | 8322.t00002 | SEQ ID NO: 19 |
| hypothetical protein, conserved | 6987.t00002 | SEQ ID NO: 20 |
| hypothetical protein, conserved | 6967.t00003 | SEQ ID NO: 21 |

Furthermore, as described below, the present invention also includes a method for identifying additional antigenic polypeptides indicative of *T. cruzi* infection. The use of the additional *T. cruzi* polypeptides thus identified, or antigenic subunit or analog thereof, alone or in combination with each presence of antibodies or reactive T cells) in the subject to multiple antigenic *T. cruzi* polypeptides, or antigenic subunits or analogs thereof. The panel may contain a number of antigenic *T. cruzi* polypeptides, or antigenic subunits or analogs thereof, wherein said number is between 5 and 50 or even more, depending on the embodiment and the intended application. For example, the panel may contain 5, 8, 10, 12, 15, 18, 20, 25, 30, 40 or more antigenic *T. cruzi* polypeptides. A typical multicomponent panel may contain 10 to 20 antigenic *T. cruzi* polypeptides. Conveniently, the *T. cruzi* polypeptides that are used in the multicomponent diagnostic test can be recombinant polypeptides; however they can be naturally occurring polypeptides or polypeptides that have been chemically or enzymatically synthesized, as well.

In one embodiment, the diagnostic test takes the form of a serodiagnostic assay, which detects a humoral (antibody) immune response in the subject. The binding of an antibody that is present in a biological fluid, such as a serum antibody, to any of the various components of the panel is determined. The threshold for a diagnosis of *T. cruzi* infection can be readily determined by the scientist, medical personnel, or clinician, for example based upon the response of known infected and control sera to the particular panel being used. For example, diagnosis criteria can be based on the number of "hits" (i.e., positive binding events) or they can represent a more quantitative determination based, for example, on the intensity of binding and optional subtraction of background. As an illustrative example, the multicomponent panel could contain 15 to 20 antigenic polypeptides, or antigenic analogs or subunits thereof, and a positive diagnosis could be interpreted as, say, 5 or more positive responses. Optionally, the serodiagnostic test could be further refined to set quantitative cutoffs for positive and negative based upon the background response to each individual panel component. So, for example, the response to each polypeptide could be set to be >2 standard deviations above the response of "pooled normal," sera and an individual would have to have responses to a minimum of 5 out of 20 polypeptides.

The serodiagnostic assay of the invention can take any convenient form. For example, standard immunoassays such as indirect immunofluorescence assays (IFA), enzyme-linked immunosorbent assay (ELISA), radioimmunoassay (RIA), fluorescent bead technology and Western blots can be employed. Detection can be by way of an enzyme label, radiolabel, chemical label, fluorescent label, chemiluminescent label, a change in spectroscopic or electrical property, and the like.

In another embodiment, the diagnostic method can take the form of a cellular assay. In this embodiment, a multicomponent panel of antigenic *T. cruzi* polypeptides as described herein is used to assess T cell responses in a mammalian subject, thereby providing another method for evaluating the presence or absence (or stage, etc.) of *T. cruzi* infection. Individuals are known who are serologically negative (based upon conventional tests) but who have T cells reactive with parasite antigens (usually a lysate of trypomastigotes and epimastigotes—but in some cases also against specific *T. cruzi* polypeptides). This suggests that T cell responses may be a sensitive way to assess infection, or to determine the stage of infection or exposure.

Recombinant antigenic *T. cruzi* polypeptides can be readily produced, for example, as histidine-tagged polypeptides. These His-tagged polypeptides can be purified onto a nickel-coated substrate, then added to a blood fraction comprising peripheral blood lymphocytes (e.g., a peripheral blood mononuclear cell, PBMC, fraction). The ability of the T cells to make IFN-gamma is then assessed, for example using an ELISPOT assay (e.g., Laucella et al., J Infect Dis. 2004 Mar. 1; 189(5):909-18). As another example, antigenic *T. cruzi* polypeptides, or antigenic analogs or subunits thereof, can be bound to major histocompatibility complex (MHC) tetramers and presented to T cells, for example in a composition of peripheral blood lymphocytes, in a microarray format. In this assay, smaller polypeptides, for example antigenic peptide subunits of antigenic *T. cruzi* polypeptides described herein, are preferred as they are more readily bound to the MHC tetramers and recognized by the T cells. Antigenic subunits of antigenic *T. cruzi* polypeptides can be predicted using various computer algorithms, and are amenable to chemical synthesis. Binding of T cells to the spots containing MHC-polypeptide complexes indicates recognition and hence *T. cruzi* infection. See, for example, Stone at al (Proc. Nat'l. Acad. Sci. USA, 2005, 102:3744) and Soen et al. (PLoS. Biol, 2003, 1:429) for a description of the general technique.

The panel components can be assembled on any convenient substrate, for example on a microtiter plate, on beads, or in a microarray on a microchip. A microarray format is advantageous because it is inexpensive and easy to read using a standard fluorescence microscope. In this format, one might just use the total number of spots (proteins) positive for each test patient to make a positive or negative diagnosis. In addition, the diagnostic test of the invention is well-suited to adaptation for use with commercially available high-throughput devices and immunoassay protocols, for example those available from Abbott Laboratories and Applied Biosystems, Inc. The serodiagnostic assay can also take the form of an immunochromatographic test, in the form of a test strip loaded with the panel components. The bodily fluid can be wicked up onto the test strip and the binding pattern of antibodies from the fluid can be evaluated.

Blood Supply Screening

The diagnostic test of the invention can be used to detect the presence of *T. cruzi* infection in blood and blood products or fractions include whole blood as well as such as cellular blood components, including red blood cell concentrates, leukocyte concentrates, and platelet concentrates and extracts; liquid blood components such as plasma and serum; and blood proteins such as clotting factors, enzymes, albumin, plasminogen, and immunoglobulins, or mixtures of cellular, protein and/or liquid blood components. Details regarding the make-up of blood, the usefulness of blood transfusions, cell-types found in blood and proteins found in blood are set forth in U.S. Pat. No. 5,232,844. Techniques regarding blood plasma fractionation are generally well known to those of ordinary skill in the art and an excellent survey of blood fractionation also appears in Kirk-Othmer's Encyclopedia of Chemical Technology, Third Edition, Interscience Publishers, Volume 4.

A sample is contacted with a multicomponent panel of the invention, and a positive or negative response is detected as described above for clinical use of the assay in patients suspected of having *T. cruzi* infection. Advantageously, the diagnostic test is readily automated, for example using microchip technology, for the processing of large numbers of samples.

Prophylactic and Therapeutic Immunization

In another aspect, the present invention is directed to both prophylactic and therapeutic immunization against *T. cruzi* infection and the chronic disease state, known as Chagas disease, that often eventually follows initial *T. cruzi* infection. Antigenic *T. cruzi* polypeptides described herein, or identified using a screening method described herein, may be immunogenic. That is, they may elicit a humoral (B cell) response and/or a cell-mediated immune response (i.e., a "T cell" response) in the subject. A cell-mediated response can involve the mobilization helper T cells, cytotoxic T-lymphocytes (CTLs), or both. Preferably, an immunogenic polypeptide elicits one or more of an antibody-mediated response, a $CD4^+$ Th1-mediated response (Th1: type 1 helper T cell), and a CD8+ T cell response. Therapeutic administration of the polynucleotide or polypeptide vaccine to infected subjects is expected to be effective to delay or prevent the progression of the *T. cruzi* infection to a chronic disease state, and also to arrest or cure the chronic disease state that follows *T. cruzi* infection. Prophylactic administration of the polynucleotide or polypeptide vaccine to uninfected subjects is expected to be effective to reduce either or both if the morbidity and mortality associated with infection by *T. cruzi*. Further, if an uninfected, vaccinated subject is subsequently infected with *T. cruzi*, the vaccine is effective to prevent progression of the initial infection to a chronic disease state. As discussed in more detail hereinbelow, the vaccine can contain or encode a single immunogenic polypeptide or multiple immunogenic polypeptides. Methods for identifying nucleotide sequences encoding such polypeptides from a *T. cruzi* genomic library using, for example, expression library immunization (ELI) or DNA microarray analysis are described below.

Advantages of a Genetic Vaccine

The choice of polynucleotide delivery as an immunization technique offers several advantages over other vaccine or antigen delivery systems. Vaccines containing genetic material are favored over traditional vaccines because of the ease of construction and production of the vectors, the potential for modification of the sequences by site-directed mutagenesis to enhance the antigenic potency of the individual epitopes or to abolish epitopes that may trigger unwanted response, in the case of DNA vaccines, the stability of DNA, the lack of the dangers associated with live and attenuated vaccines, their ability to induce both humoral and cell mediated immunity and, in particular, CD8$^+$ T cell responses, and the persistence of the immune responses. Successful induction of humoral and/or cellular immune responses to plasmid-encoded antigens using various routes of gene delivery have been shown to provide partial or complete protection against numerous infectious agents including influenza virus, bovine herpes virus I, human hepatitis B virus, human immunodeficiency virus-1, as well as parasitic protozoans like *Plasmodium* and *Leishmania* (J. Donnelly et al., *Ann. Rev. Immunol.* 15:617-648 (1997)). Representative papers describing the use of DNA vaccines in humans and primates include V. Endresz et al. (*Vaccine* 17:50-58 (1999)), M. McCluskie et al. (*Mol. Med.* 5:287-300 (1999)), R. Wang et al. (*Infect. Immun.* 66:4193-202 (1998)), S. Le Borgne et al. (*Virology* 240:304-315 (1998)), C. Tacket et al. (*Vaccine* 17:2826-9 (1999)), T. Jones et al. (*Vaccine* 17:3065-71 (1999)) and R. Wang et al. (Science 282(5388):476-80 (1998)). The ability to enhance the immune response by the co-delivery of genes encoding cytokines is also well-established.

Polynucleotide Vaccine

The polynucleotide vaccine of the invention includes at least one, preferably at least two, nucleotide coding regions, each coding region encoding an immunogenic polypeptide component from *T. cruzi* as identified herein and/or using the screening method described herein. When it contains two or more nucleotide coding regions, the polynucleotide vaccine is referred to herein as a "multicomponent" polynucleotide vaccine. It is desirable to minimize the number of different immunogenic polypeptides encoded by the nucleotide coding regions in the polynucleotide vaccine; however, it is nonetheless contemplated that a polynucleotide vaccine that generates the highest level of protection will encode 10 or more immunogenic polypeptides.

The polynucleotide vaccine can contain DNA, RNA, a modified nucleic acid, or any combination thereof. Preferably, the vaccine comprises one or more cloning or expression vectors; more preferably, the vaccine comprises a plurality of expression vectors each capable of autonomous expression of a nucleotide coding region in a mammalian cell to produce at least one immunogenic polypeptide or cytokine, as further described below. An expression vector preferably includes a eukaryotic promoter sequence, more preferably the nucleotide sequence of a strong eukaryotic promoter, operably linked to one or more coding regions. A promoter is a DNA fragment that acts as a regulatory signal and binds RNA polymerase in a cell to initiate transcription of a downstream (3' direction) coding sequence; transcription is the formation of an RNA chain in accordance with the genetic information contained in the DNA. A promoter is "operably linked" to a nucleic acid sequence if it is does, or can be used to, control or regulate transcription of that nucleic acid sequence. The invention is not limited by the use of any particular eukaryotic promoter, and a wide variety are known; preferably, however, the expression vector contains a CMV or RSV promoter. The promoter can be, but need not be, heterologous with respect to the host cell. The promoter used is preferably a constitutive promoter.

A vector useful in the present invention can be circular or linear, single-stranded or double stranded and can be a plasmid, cosmid, or episome but is preferably a plasmid. In a preferred embodiment, each nucleotide coding region (whether it encodes an immunogenic polypeptide or a cytokine) is on a separate vector; however, it is to be understood that one or more coding regions can be present on a single vector, and these coding regions can be under the control of a single or multiple promoters.

There are numerous plasmids known to those of ordinary skill in the art useful for the production of polynucleotide vaccines. Preferred embodiments of the polynucleotide vaccine of the invention employ constructs using the plasmids VR1012 (Vical Inc., San Diego Calif.), pCMVI.UBF3/2 (S. Johnston, University of Texas) or pcDNA3.1 (InVitrogen Corporation, Carlsbad, Calif.) as the vector.

Plasmids VR1012 and pCMVI.UBF3/2 are particularly preferred. In addition, the vector construct can contain immunostimulatory sequences (ISS), such as unmethylated dCpG motifs, that stimulate the animal's immune system. Other possible additions to the polynucleotide vaccine constructs include nucleotide sequences encoding cytokines, such as granulocyte macrophage colony stimulating factor (GM-CSF), interleukin-12 (IL-12) and co-stimulatory molecules such B7-1, B7-2, CD40. The cytokines can be used in various combinations to fine-tune the response of the animal's immune system, including both antibody and cytotoxic T lymphocyte responses, to bring out the specific level of response needed to control or eliminate the *T. cruzi* infection.

The polynucleotide vaccine can also encode a fusion product containing the antigenic polypeptide and a molecule, such as CTLA-4, that directs the fusion product to antigen-presenting cells inside the host. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell.

An alternative approach to delivering the polynucleotide to an animal involves the use of a viral or bacterial vector. Examples of suitable viral vectors include adenovirus, polio virus, pox viruses such as vaccinia, canary pox, and fowl pox, herpes viruses, including catfish herpes virus, adenovirus-associated vector, and retroviruses. Exemplary bacterial vectors include attenuated forms of *Salmonella, Shigella,*

*Edwardsiella ictaluri, Yersinia ruckerii*, and *Listeria monocytogenes*. Preferably, the polynucleotide is a vector, such as a plasmid, that is capable of autologous expression of the nucleotide sequence encoding the immunogenic polypeptide.

Preferably, the polynucleotide vaccine further includes at least one nucleotide coding region encoding a cytokine. Preferred cytokines include interleukin-12 (IL-12), granulocyte-macrophage colony-stimulating factor (GM-CSF), interleukin-6 (IL-6), interleukin-18 (IL-18), γ-interferon, α,β-interferons, and chemokines. Especially preferred cytokines include IL-12 and GM-CSF.

Plasmids and other delivery systems are made using techniques well-known in the art of molecular biology. The invention should be understood as including methods of making and using the polynucleotide vaccine.

Polypeptide Vaccine

The polypeptide vaccine of the invention includes at least one, preferably at least two, immunogenic polypeptides from *T. cruzi* as described herein and/or as identified using the screening method described herein. As with the polynucleotide vaccine, it is desirable to minimize the number of different immunogenic polypeptides supplied in the vaccine; however, it is nonetheless contemplated that a polypeptide vaccine that generates the highest level of protection will contain 10 or more immunogenic polypeptides.

Because a $CD8^+$ T cell response cannot normally be directly triggered by the administration of a conventional protein subunit vaccine, the immunogenic polypeptides contained in the polypeptide vaccine preferably include one or more membrane transporting sequences (MTS) fused to their N-terminus or C-terminus or both. A membrane transporting sequence allows for transport of the immunogenic polypeptide across a lipid bilayer, allowing it to be delivered to the inside of a mammalian cell. In a particularly preferred embodiment, the immunogenic polypeptides are shocked with urea, as described further in Example VIII, prior to administration as a vaccine. From there, portions of the polypeptide can be degraded in the proteasome, and the resulting peptides can be displayed as class I MHC-peptide complexes on the cell surface. In this way, a polypeptide vaccine can stimulate a CD8+ T cell immune response. In another preferred embodiment, the immunogenic polypeptides are attached to nanoparticles and administered to a subject (e.g., Plebanski et al., J. Immunol. 2004, 173:3148; Plebanski et al., Vaccine, 2004, 23:258). A polypeptide vaccine of the invention is optionally adjuvanted using any convenient and effective adjuvant, as known to one of skill in the art.

The invention should be understood as including methods of making and using the polypeptide vaccine.

Pharmaceutical Compositions

The polynucleotide and polypeptide vaccines of the invention are readily formulated as pharmaceutical compositions for veterinary or human use. The pharmaceutical composition optionally includes excipients or diluents that are pharmaceutically acceptable as carriers and compatible with the genetic material. The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, salts, and/or adjuvants which enhance the effectiveness of the immune-stimulating composition. Methods of making and using such pharmaceutical compositions are also included in the invention.

Administration of the Polynucleotide Vaccine

The polynucleotide vaccine of the invention can be administered to the mammal using any convenient method, such as intramuscular injection, topical or transdermal application to the mammal's skin, or use of a gene gun, wherein particles coated with the polynucleotide vaccine are shot into the mammal's skin. The amount of polynucleotide administered to the mammal is affected by the nature, size and disease state of the mammal as well as the delivery method; for example, typically less DNA is required for gene gun administration than for intramuscular injection. Further, if a polynucleotide encoding a cytokine is co-delivered with nucleotide coding regions encoding the immunogenic polypeptide from *T. cruzi*, the amount of polynucleotide encoding the immunogenic polypeptide from *T. cruzi* in the vaccine is optionally reduced.

Hundreds of publications have now reported the efficacy of DNA vaccines in small and large animal models of infectious diseases, cancer and autoimmune diseases (J. Donnelly et al., Rev. Immunol. 15:617 (1997). Vaccine dosages for humans can be readily extended from the murine models by one skilled in the art of genetic immunization, and a substantial literature on genetic immunization of humans is now available to the skilled practitioner. For example, Wang et al. (*Science* 282:476-480 (1998)) vaccinated humans with plasmid DNA encoding a malaria protein, and the same group has developed a plan for manufacturing and testing the efficacy of a multigene *Plasmodium falciparum* liver-stage DNA vaccine in humans (Hoffman et al., Immunol. Cell Biol. 75:376 (1997)). In general, the polynucleotide vaccine of the invention is administered in dosages that contain the smallest amount of polynucleotide necessary for effective immunization. It is typically administered to human subjects in dosages containing about 20 µg to about 2500 µg plasmid DNA; in some instances 500 µg or more of plasmid DNA may be indicated. Typically the vaccine is administered in two or more injections at time intervals, for example at four week intervals.

Administration of the Polypeptide Vaccine.

Like the polynucleotide vaccine, the polypeptide vaccine can be administered to the mammal using any convenient method, such as intramuscular or intraperitoneal injection, topical administration, oral or intranasal administration, inhalation, perfusion and the like. The amount of polypeptide administered to the mammal is affected by the nature, size and disease state of the mammal, as well as by the delivery method. Intraperitoneal injection of 25 to 50 ug of polypeptide containing a membrane transducing sequence has been shown to result in import of the protein into nearly 100% of murine blood and spleen cells within 20 minutes (Schwarze et al., *Science* 285:1569-1572 (1999)) and the sensitization of cytotoxic T cells (M.-P. Schutze-Redelmeier et al., J. Immunol. 157:650-655 (1996)). Useful dosages of the polypeptide vaccine for humans can be readily determined by evaluating its activity in vivo activity in mice.

Administration of a Combination of Polynucleotide Vaccine and Polypeptide Vaccine.

The invention contemplates administration of both a polynucleotide vaccine and a polypeptide vaccine to a mammal in a serial protocol. For example, a plasmid-based DNA vaccine may be administered to a mammal to "prime" the immune system, followed by the one or more administrations of a polypeptide vaccine or a viral vaccine (e.g., vaccinia vector carrying the genes that encode the immunogenic polypeptides and, optionally, cytokines) to further stimulate the mammal's immune system. The order of administration of the different types of vaccines, and the nature of the vaccines administered in any given dose (e.g., polypeptide vaccine, plasmid vaccine, viral vector vaccine) can be readily determined by one of skill in the art to invoke the most effective immune response in the mammal.

Screening Method for Identification of Antigenic *T. cruzi* Polypeptides

In another aspect, the invention provides high-throughput method to screen putative *T. cruzi* polypeptides for diagnostic potential. The antigenic polypeptides thus identified can be incorporated into a diagnostic test for *T. cruzi* as described herein.

*T. cruzi* polypeptides that are preferred candidates for screening, either individually or as part of a pool, have one or more of the following characteristics or features. The *T. cruzi* polypeptides may be abundant in the trpomastigote and/or amastigote stages of the *T. cruzi* life cycle in mammals, as described in more detail above. Additionally or alternatively, the *T. cruzi* polypeptides may be, or may be likely to be, surface-associated or secreted. Surface associated-antigenic polypeptides include, for example, *T. cruzi* proteins that are anchored to the plasma membrane by glycosylphosphotidylinositols, or GPIs, and those that have transmembrane domains or are otherwise embedded in the plasma membrane. This property can be evaluated, for example, by analyzing the polypeptide sequence for the presence of an N-terminal leader sequence which directs the polypeptide to the cell membrane; by analyzing the polypeptide sequence for the presence of a known GPI sequence that facilitates attachment of the polypeptide to the cell surface; and/or by analyzing the polypeptide sequence for the presence of a transmembrane domain. Another preferred feature is that the polypeptide is unique to *T. cruzi* and not expressed in other organisms, including other kinetoplastids. This can be determined by performing BLAST searches of GenBank entries for other organisms and/or comparative genomics with *T. brucei* and *Leishmania major*. This feature enhances the specificity of the diagnostic test.

Another preferred feature is that the *T. cruzi* polypeptide be one that is less likely than others to be highly variant. For example, members of large gene families that appear to undergo rearrangements that create new variants are generally not preferred. However, pools of large gene family members (such as the trans-sialidase family, the Mucin-associated surface protein (MASP) family, and other smaller families of genes can be cloned and tested using degenerate primers. In that case, rather than a bead or a spot in the diagnostic test containing only one gene family member, it may have ten or hundreds, thereby circumventing the problem of recombination and variation in these families, and providing a better representation of the family than a single (possibly variant) protein.

The screening method involves providing two substrates that include a plurality of individually addressable candidate antigens derived from *T. cruzi*, in which the antigens present on both substrates are substantially the same. A substrate, as defined herein, is a surface of unreactive material that can be used to contain the individually addressable candidate antigens in isolation from one another. For example, a multiwelled array system such as a 96 well microplate is a substrate useful in the method of screening for serodiagnostic *T. cruzi* antigens. Individually addressed candidate antigens refers to potentially serodiagnostic *T. cruzi* antigens that have been positioned and/or labeled in such a way that differing antigens can be discretely identified using methods known to those skilled in the art. For example, antigens obtained directly or indirectly from *T. cruzi*, labeled with a fluorescent label with a different wavelength sensitivity from other fluorescent labels used with other antigens and positioned within a specific well or set of wells on a multi-welled array system, are individually addressed candidate antigens.

Candidate antigens immobilized on the first substrate are contacted with a body fluid from an organism known to be positive for *T. cruzi* infection based on a detection method such as a T cell assay, polymerase chain reaction (PCR), hemoculture or xenodiagonstic techniques. The organism is preferably a mammal, more preferably a dog or a human. Preferably, the organism exhibits negative serology when tested for *T. cruzi* infection utilize conventional serodiagnostic tests that rely on antigens from either whole to semi-purified parasite lysates, for example from epimastigotes, that react with anti-*T. cruzi* IgG antibodies.

Candidate antigens immobilized on the first substrate are contacted with the second substrate with a body fluid from an organism known or reasonably believed to be unexposed to *T. cruzi* infection. The second substrate serves as a control. The organism does not exhibit a strong positive serological signal indicating infection by *T. cruzi*. Preferably, the organism shows no evidence of *T. cruzi* infection by any other diagnostic test as well. Optionally, the screening method includes testing of additional substrates using body fluids that are strongly, weakly and/or borderline seropositive using conventional tests for *T. cruzi*, as described in more detail below.

The body fluid may be any fluid found within the body of an organism that is capable of containing components of *T. cruzi* or immune system components prepared in response to exposure to *T. cruzi*. For example, an immune system component may be an antibody that specifically binds to a *T. cruzi* antigen. Such body fluids include, for example, blood, plasma, serum, urine, saliva, tears, lymphatic fluid, and the like.

The organism itself may be any organism that can be infected by *T. cruzi*, including vector organisms. For example, organisms may include insect vectors of Chagas disease belonging to the Hemiptera order, Reduviidae family, and Triatominae subfamily. The organism can also be a vertebrate reservoir of *T. cruzi* infection. Mammals are most susceptible to infection with *T cruzi*, with approximately 150 species known to serve as reservoirs. Birds, amphibians, and reptiles are naturally resistant to infection. In the domestic cycle, frequently infected mammals, besides humans, are dogs, cats, mice, rats, guinea pigs, and rabbits. Pigs, goats, cattle, and horses can be infected by *T. cruzi*, but generally only manifest transitory parasitemia. Humans are a preferred organism due to the importance of diagnosing *T. cruzi* infection in humans.

Antigens that exhibit binding to antibodies present in the bodily fluid contacted with the first substrate but little or no binding to antibodies present in the control bodily fluid contacted with the second substrate are identified as antigenic *T. cruzi* polypeptides for use in the muticomponent diagnostic assay. The binding of an antigen to an antibody can be detected by various means known to those skilled in the art. For example, the association may be detected using flow cytometry, or by enzyme immunoassay (EIA) or enzyme-linked immunoassay (ELISA). Preferably, the association of one or more antibodies with multiple antigens is detected using a multiplex analysis system such as the BIO-PLEX multiplex analysis system commercially available from, for example, Bio-Rad® Laboratories (Hercules, Calif.).

The BIO-PLEX suspension array system is a biomarker assay system that includes a flow-based 96-well fluorescent microplate assay reader integrated with specialized software, automated validation and calibration protocols, and assay kits. The multiplex analysis system utilizes up to 100 fluorescent color-coded bead sets, each of which can be conjugated with a different specific antigen. The term "multiplexing" refers to the ability to analyze many different antigens essentially simultaneously. To perform a multiplexed assay, sample and reporter antibodies are allowed to react with the conjugated bead mixture in microplate wells. The constituents of each well are drawn up into the flow-based BIO-PLEX array reader, which identifies each specific reaction based on bead color and quantitates it. The magnitude of the reaction is measured using fluorescently labeled reporter antibodies specific for each antibody that may associate with the antigen being tested.

Figure 1B:
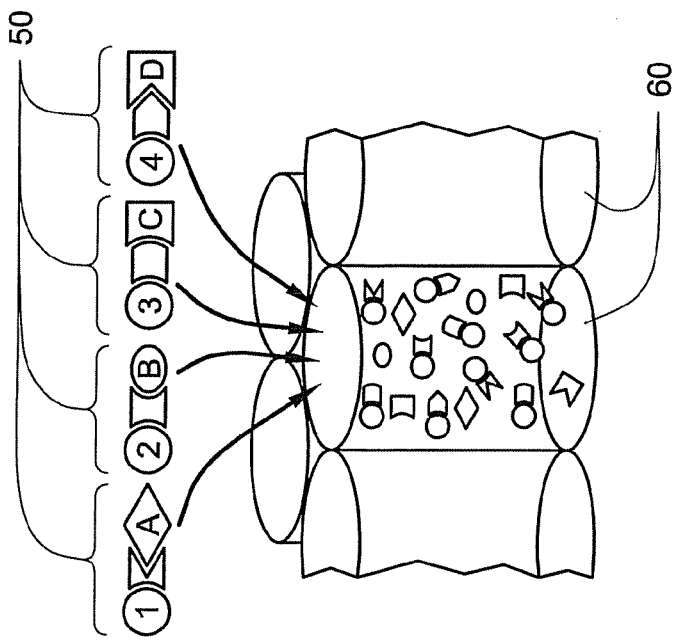
Figure 1A:
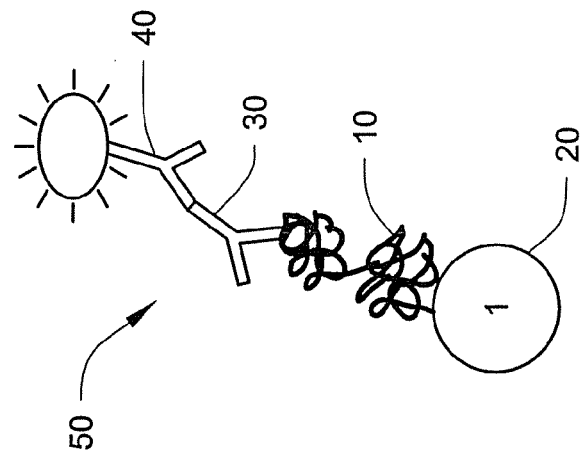

The BIO-PLEX suspension array system uses a liquid suspension array of about 100 sets of micrometer-sized beads, each internally dyed with different ratios of two spectrally distinct fluorophores to assign it a unique spectral address. The overall operation of the BIO-PLEX array system is illustrated in FIGS. 1A through 1C. As shown in FIG. 1A, polypeptide antigen 10 is bound to a microsphere bead 20 by, for example, a histidine tag. The polypeptide antigen 10 is then contacted with a sample of sera containing an antibody; for example, an anti-*T. cruzi* antibody 30. This antibody, in turn, is contacted with a fluorescently labeled reporter antibody 40 to form a microsphere-antigen-antibody complex 50. As shown in FIG. 1B, since the microsphere beads 20 provide a large variety of different colors, and the microsphere beads 20 were earlier attached only to specific polypeptide antigens 10, a number of microsphere-antigen-antibody complexes 50 may be present in a microplate well 60. The complexes 50 are then run through a flow cytometry apparatus 70 that includes a classifying laser 70 and a reporting laser 80. The reporting laser 80 determines the amount of a particular antigen present, based on the amount of fluorescently labeled reporter antibody 40. The classifying laser 90, on the other hand, determines the frequency of fluorescence provided by the microsphere bead 20, and based on this frequency, the identity of the polypeptide antigen 10 can be determined.

In the embodiment used in this invention, the BIO-PLEX assay utilizes dyed beads containing nickel to capture the His-tagged *T. cruzi* polypeptides produced in the host bacterial cells. Each spectrally addressed bead captures a different protein. The protein-conjugated beads are allowed to react with a sample, and biomolecules in the sample (typically antibodies) bind to the bound protein antigens as further described in the Examples.

It should be understood that the invention is not limited to multiplexing as employed in the BIO-PLEX assay; other multiplexed approaches can readily be used. For example, protein arrays can be placed on a matrix, and the response to the individual proteins on the solid-phase array can be assayed.

An important advantage of using a multiplexed method is that a plurality of serodiagnostic antigens may be identified during a single run of the analysis. For example, serological responses to as many as a 100 individual proteins can be screened at one time, and the pattern of responsiveness to all 100, or any subset thereof, can be used to make or assist in making a diagnosis. Tests in current use employ crude antigen preparations from *T. cruzi* itself (an undefined composition thus not very reproducible), or utilize an individual recombinant protein (i.e., a single target thus not very robust) or a string of three portions of three different proteins combined in one synthetic protein. In the latter case, there is more than one target, but still the response to only a single entity is measured, thus the assay lacks robustness.

Optionally, the method of the invention can utilize more than two substrates that include a plurality of individually addressed candidate antigens. These additional substrates can be used, for example, to evaluate the body fluids from organisms classified as providing a very high positive sera response, intermediate positive sera response, very low positive sera response or a borderline positive sera response. When used to supplement data obtained on sera from control (uninfected) organisms and organisms that are or have been infected but show little or no positive serological response, these substrates can provide additional information on candidate *T. cruzi* antigens that may be used as serodiagnostic antigens. Measuring the pattern of responses to many antigens is also useful for evaluating other aspects of the *T. cruzi* infection such as the stage of the disease, its severity, or the particular strain of *T. cruzi* involved.

The method of screening for serodiagnostic *T. cruzi* antigens can also be done at the less specific level of an antigen pool, rather than specific antigens. An antigen pool, as defined herein, is a plurality of antigens in a mixture. Antigen pools may be used either as a means of evaluating a wide number of antigens more rapidly, as a means of evaluating mixtures of antigens for possible interactions, or simply out of necessity when the identify of specific antigens is not known. The method of screening antigen pools can be done either as an independent analysis method, or it may be an optional preliminary step to the screening of individual *T. cruzi* antigens for potential as serodiagnostic antigens. In either case, the method of analyzing antigen pools includes providing two substrates that include a plurality of individually addressable antigen pools derived from *T. cruzi*, where the antigen pools present on the two substrates are substantially the same. The first substrate is then contacted with a body fluid from an organism known to be serologically positive for *T. cruzi* infection, while the second substrate is then contacted with a body fluid from an organism known to be not serologically positive for *T. cruzi* infection. Antigen pools that associate with an antibody present in the body fluid from an organism known to be serologically positive but that are absent or present to a lesser degree in the body fluid of an organism known to be not serologically positive for *T. cruzi* infection are thereby identified as serodiagnostic antigen pools that may be used by themselves or further evaluated to determine that specific antigens involved.

The candidate antigens derived from *T. cruzi* that are screened by the method of the invention can include antigens formed from polypeptides, polysaccharides, polynucleotides, or other substances present in *T. cruzi* that are capable of being specifically bound by antibodies. As polypeptides are known by those skilled in the art to be the most common and diverse antigens, the method of the invention preferably identifies polypeptide antigens. Polypeptide antigens can be obtained directly from *T. cruzi* using biochemical separation technology, particularly protein purification methods. More preferably, the polypeptide antigens are obtained using recombinant DNA technology. Using recombinant DNA technology, nucleotide sequences from *T. cruzi* are inserted into a host organism where they are used to direct product of a polypeptide that may contain one or more antigens that may be detected by the screening method.

The smallest useful peptide sequence contemplated to provide an antigen is generally on the order of about 6 amino acids in length. Thus, this size will generally correspond to the smallest polypeptide antigens that are screened for by the method of the invention. It is proposed that short peptides that incorporate a species-specific amino acid sequence will provide advantages in certain circumstances, for example, in the preparation of vaccines or for use in methods of detecting *T. cruzi*. Exemplary advantages of shorter peptides include the ease of preparation and purification, and the relatively low cost and improved reproducibility of production. However, the size of polypeptide antigens may be significantly larger. Longer polyptide antigens identified by the method may be on the order of 15 to 50 amino acids in length, or may represent an entire protein, including modified proteins such as fusion proteins.

Preparation of the polypeptide antigens will generally include the use of an expression vector. An expression vector is a cloning vector that contains the necessary regulatory sequences to allow transcription and translation of a cloned gene or genes. An expression vector preferably includes a promoter sequence operably linked to one or more coding regions. A promoter is a DNA fragment that acts as a regulatory signal and binds RNA polymerase in a cell to initiate transcription of a downstream (3' direction) coding sequence; transcription is the formation of an RNA chain in accordance with the genetic information contained in the DNA. A promoter is "operably linked" to a nucleic acid sequence if it is does, or can be used to, control or regulate transcription of that nucleic acid sequence. The invention is not limited by the use of any particular promoter. A wide variety of promoters are known by those skilled in the art.

A vector useful in the present invention can be circular or linear, single-stranded or double stranded and can be a plasmid, cosmid, or episome but is preferably a plasmid. In a preferred embodiment, each nucleotide coding region encoding an antigenic polypeptide is on a separate vector; however, it is to be understood that one or more coding regions can be present on a single vector, and these coding regions can be under the control of a single or multiple promoters.

There are numerous expression vectors known to those of ordinary skill in the art useful for the production of polypeptide antigens. A preferred expression vector is an expression vector formed using the GATEWAY® cloning method. The GATEWAY® cloning method is a universal cloning technique that allows transfer of DNA fragments between different cloning g vectors while maintaining the reading frame, and has effectively replaced the use of restriction endonucleases and ligases. The steps involved in the GATEWAY® cloning method are shown in FIG. 2. First, a gene is selected for cloning. For the present invention, this would be a gene selected from *T. cruzi*. The gene is then provided with primers and amplified using PCR technology with the help of an attB tagged primer pair, as readily practiced by those skilled in the art. The PCR fragment then combined with a donor vector (pDONR™) that includes attP sites to provide an entry clone, using the BP reaction. An integration reaction between the attB and the attP sites combines the PCR fragment with the donor vector. The resulting entry clone contains the gene of interest flanked by attL sites. The LR reaction is then used to combine the entry clone with a destination vector to produce an expression vector. In the LR reaction, a recombination reaction is used to link the entry clone with the destination vector (pDEST™) using the attL and attR sites and a CLONASE enzyme. The attL sites are already found in the entry clone, while the destination vector includes the attR sites. The LR reaction is carried out to transfer the sequence of interest into one or more destination vectors in simultaneous reactions, making the technology high throughput. For example, as this method allows multiple genes to be transferred to one or more vectors in one experiment, this method readily allows multiple antigenic polypeptides to be prepared that can then be screened by the method of the invention, potentially revealing a plurality of serodiagnostic antigens.

The *T. cruzi* genes are cloned into expression vectors, as described, which are then expressed in a host cell, such as a bacterial cell, yeast cell, insect cell, protozoan call, or mammalian cell. A preferred host cell is a bacterial cell, for example an *E. coli* cell. Another preferred cell is a protozoan cell, more preferably a kinetoplastid cell, most preferably a *Crithidia* cell (U.S. Pat. No. 6,368,827; Apr. 9, 2002). Proteins are isolated from the host cell, purified, and analyzed. Preferably, the proteins are purified onto beads that are then used in a BIO-PLEX assay, as described. Various serum samples (e.g., negative, mildly positive, strongly positive) can be efficiently screened for reactivity with a large number of gene products to identify those gene products that are associated with *T. cruzi* infection, for example those indicative of the existence of and, optionally, the extent and/or stage of *T. cruzi* infection. Typically, the identified antigens elicit an antibody response *T. cruzi* in a mammal. The genes and gene products thus identified are useful in diagnostic assays for *T. cruzi*.

The Examples that follow provide representative data from a screening of more than 350 *T. cruzi* gene products. Following FIG. 4-6 in the Examples, a procedure including a preliminary screening of antigen pools, followed by screening for specific antigens, is described. Four different substrates were used to provide data for the reactivity of the antigens in sera with various levels of reactivity to *T. cruzi* antigens. One pool, labeled "3K" on FIG. 4D, was selected for further analysis because it showed good reactivity with the positive sera. The "3K" pool was broken down into individual constituent gene products, and four of the gene products (antigens) were identified as potential candidates for diagnostic use. The "top" antigens identified this way can be combined into a single, robust diagnostic assay for *T. cruzi*. Examples of gene products identified in accordance with the invention are also described.

The method of screening is also capable of identifying antigens that do not consistently elicit a strong B cell response. The majority of conventional and commercially available serological methods for diagnosis and blood screening of *T. cruzi* infection utilize either crude or semi-purified parasite lysates typically from epimastigotes. However the complex nature of molecules in these lysates creates a test that routinely gives false positive diagnosis. Research to improve serological diagnosis techniques has focused on the identification, characterization and cloning of particular *T. cruzi* antigens that elicit a strong B cell response. Experiments have demonstrated that some individuals declared negative by current serological tests in fact respond to parasite lysate by producing IFN-gamma in ELISPOT assays. These individuals therefore have T cells that have been exposed to parasite antigen but have a poor B cell antibody response to the antigens in the serological tests that use parasite lysate. The present invention is capable of detecting components present in the sera of such individuals, as shown in FIG. 6.

It is to be understood that other screening methods are applicable to the identification of antigenic *T. cruzi* polypeptides to be included in the multicomponent panel for the diagnostic test. For example, U.S. Pat. No. 6,875,584, issued Apr. 5, 2005, describes screening methods that can be used to identify additional antigenic *T. cruzi* polypeptides for use in a diagnostic test and/or as vaccine components. As another example, a nickel-coated substrate, such as a nanoparticle array, can be used to immobilize His-tagged candidate antigens which can then be contacted with serum or other blood product (in the case of the serodiagnostic test) or MHC-peptide complexes (in the case of the cellular test) to detect evidence of an immune response in the serum.

The present invention is illustrated by the following examples. It is to be understood that the particular examples, materials, amounts, and procedures are to be interpreted broadly in accordance with the scope and spirit of the invention as set forth herein.

EXAMPLES

The majority of current serological tests for *T. cruzi* infection utilize whole to semi-purified parasite lysates and are often inconclusive or result in false positives. Recent studies have identified individuals who are seronegative for *T. cruzi* infection by standard tests but are positive by PCR (Salomone et. al. Emerg. Infect. Disease, 2003, 9:1558) or have demonstrable cellular immune responses to *T. cruzi*. With respect to the latter, our lab has recently demonstrated that some individuals declared negative by current serological tests in fact have demonstrable T cell responses to parasite lysate as seen in ELISPOT assays. These individuals therefore have T cells which have been exposed to parasite antigen but have a poor B cell antibody response to the mix of antigens in the serological test. It is apparent that the use of lysates is a poor test for *T. cruzi* infection and we expect that screening with multiple recombinant proteins will be able to reduce the number of false positives, and more importantly false negatives.

We have therefore developed a high-throughput method to screen large numbers of recombinantly expressed *T. cruzi* proteins for their serodiagnosis potential. Specifically, we combined a set of putative *T. cruzi* genes cloned into the GATEWAY SYSTEM® with the BIOPLEX LIQUICHIP bead technology to screen large numbers of recombinantly expressed proteins for their antigenicity using only a small volume of sample (<100 µl). So far, we have produced 34 pools of approximately 10 proteins each and screened them for antigenicity. From the preliminary testing, 11 pools were found to bind readily detectable amounts of antibodies in the sera of *T. cruzi*-infected subjects. These pools were then broken down and each gene was expressed individually and tested. From these 81 genes we have been able to define more than 15 proteins with serodiagnostic potential.

Our method utilizes a blind screening process that has identified several known antigens as well as previously unidentified antigenic proteins from within pools containing multiple non-antigenic proteins. The use of the BIO-PLEX technology is not limited to antigen screening but its full potential may be realized as a novel method of blood donor screening. The highly antigenic proteins we discovered, and expect to continue to discover, with this method can be used to create a highly sensitive and specific test for *T. cruzi* infection.

Example 1

Buffer and Medium Preparation

A variety of buffers were used in the BIO-PLEX multiplex analysis. The buffers were prepared as follows. To prepare 1 liter of PBS/BSA (10 mM $NaH_2PO_4$, 150 mM NaCl, and 0.1% (w/v) BSA), 8.77 g NaCl (MW 58.44 g/mol) and 1.4 g $NaH_2PO_4$—$H_2O$ (MW 137.99 g/mol) were dissolved in 900 ml $H_2O$ and the pH was adjusted to 7.4 using NaOH. Then, dissolve 1 gram of BSA and adjust the volume to 1 liter. Before use, filter the buffer using a 0.45 µM filter. Sodium Azide should be added to 0.5% when storing the PBS/BSA buffer for long term. Azide should not be used with Carboxy Beads.

To prepare 1 liter of coupling buffer (50 mM MES), 11.67 g MES (MW 233.2 g/mol) was dissolved in 900 ml $H_2O$ and the pH was adjusted to 5.0 using NaOH. The volume was then adjusted to 1 liter using additional $H_2O$. Before use, the buffer should be filtered using a 0.45 µM filter.

To prepare 1 liter of activation buffer (100 mM $NaH_2PO_4$), 13.80 g $NaH_2PO_4$—$H_2O$ (MW 137.99 g/mol) was dissolved in 900 ml $H_2O$ and the pH was adjusted to 6.3 using NaOH. The volume was then adjusted to 1 liter using additional $H_2O$. Before use, the buffer should be filtered using a 0.45 µM filter.

To prepare Buffer Z, 8 M urea, 20 mM Hepes, and 100 mM NaCl are combined and dissolved in deionized water to form a solution. The pH of the solution is adjusted to 8.0, and the solution is filtered through a 0.45 µm filter and stored at room temperature. Imidazole (the side chain molecule in histidine) is added to Buffer Z at varying concentrations to either prevent the cobalt resin from binding non-specifically to something other than the histidine tag, or to out-competing the binding of the histidine tag and thus causing the protein to elute off the resin.

To prepare LB (Luria-Bertani) Medium, 10 g tryptone, 5 g yeast extract, and g. NaCl were dissolved in 1 L deionized water and autoclaved for 25 minutes. For plates, 15 grams of agarose were also dissolved into the water prior to autoclaving.

Example 2

Production of Protein Pools or Individual Proteins

To provide a large set of *T. cruzi* proteins, over 350 proteins in pools of approximately 10 proteins each were prepared. The proteins were prepared using the GATEWAY® universal cloning technique developed by Invitrogen™. The procedure can be carried out by cloning a pool of several genes together, which results in a pool of proteins, or by cloning an individual gene, resulting in the preparation of an individual protein. For preparation of an individual protein, a gene that codes for a desired *T. cruzi* protein is first selected for cloning. This gene is amplified from *T. cruzi* genomic DNA using gene specific primers flanked by lambda phage recombination sites, attB1 (5') and attB2 (3') and polymerase chain reaction. Gel purification of the att-flanked PCR produced was carried out by separating the PCR reaction product on a 1% agarose gel using electrophoresis. The particular gene is identified by comparison with a DNA standard containing bands of known size. The band of the gene of interest is cut out of the gel and purified using Sigma-Aldrich's GenElute Minus EtBr Spin Columns (Catalog No. 5-6501).

The GATEWAY® BP reaction is then used to insert the att-flanked *T. cruzi* gene fragment with a pDONR™201 vector (Catalog No. 11798-014, Invitrogen Corp., Carlsbad, Calif.). The BP reaction is conducted by adding the 5 µl of gel-purified attB-flanked PCR product (40-100 fmoles), 1 µl of the pDONR™201 vector (supercoiled, 150 ng/µl), and 2 µl 5×BP CLONASE™ Reaction Buffer (Catalog No. 11789-013) to obtain a final volume of 8 µl. The BP CLONASE™ enzyme mix (Catalog No. 11789-013, Invitrogen Corp., Carlsbad, Calif.) is mixed gently, and then 2 µl of the enzyme mix was added to the BP reaction mixture and mixed well. The reaction was then incubated at (room temperature) 25° C. overnight. Next, 1 µl of Proteinase K solution (Catalog No. 11789-013, Invitrogen Corp., Carlsbad, Calif. 2 µg/µl) was added, and the mixture was allowed to incubate for 10 minutes at 37° C. Five microliters of the BP reaction are transformed by heat shock into chemical competent DH5α cells and grown up overnight at 37° C. shaking at 280 RPM in 5 mL of LB with 50 mg/L kanamycin to select for pDONR201-transformed cells. The plasmid is then purified from the culture using a QIAprep Spin Miniprep Kit (Catalog No. 27106, Qiagen Inc., Valencia, Calif.).

For the next step of protein production, the GATEWAY LR® recombination reaction was used to insert the gene of interest in pDONR201 into a destination vector to provide the final expression clone. The destination vector in this case is a modified version of Invitrogen's pRSET (Catalog No. V351-20), called pDEST-PTD4. First, the pDEST-PTD4 was linearized by restriction digest of a novel site (PvuII) within the cell death cassette. The linearized plasmid was purified using QIAquick Gel Extraction Kit (Catalog No. 28207, Qiagen Inc., Valencia, Calif.). The LR reaction between the gene of interest in the pDONR™201 vector and the desired pDEST-PTD4 expression vector was then set up. First, 300 ng of the pDONR entry clone (prepared above), 300 ng of linearized pDEST-PTD4 (Invitrogen Corp., Carlsbad, Calif.), and 2 μl LR CLONASE Reaction Buffer (Catalog No. 11791-019, Invitrogen Corp., Carlsbad, Calif.), 2 μl LR CLONASE Enzyme Mix, and deionized water are combined to obtain a final volume of 10 μl and mixed thoroughly by flicking the tube. The reaction was then incubated overnight at 25° C. Next, 2 μl proteinase K solution (2 μg/μl) was added and the mix was allowed to incubate for 10 minutes at 37° C. DH5α cells were then transformed by heat shock with 6 μl of LR reaction products, and plated onto LB agar plates containing 150 mg/L ampicillin and incubated overnight at 37° C. to select for ampicillin-resistant expression clones.

Next, all of the colonies were scraped clean with a clean sterile spatula, and used to inoculate a tube of 5 mL LB containing 150 mg/L ampicillin, and grown overnight at 37° C., 280 RPM. The pDEST-PTD4 containing the gene of interest is purified from the culture using a QIAprep Spin Miniprep Kit (Catalog No. 27106, Qiagen Inc., Valencia, Calif.). The miniprep preparation should contain copies of each gene of the pool from the desired pDEST vector. Three microliters of purified pDEST-PTD4 containing the gene of interest was then transformed into BL21(DE3)pLysS chemical competent cells. The culture was then directly inoculated into 10 ml LB/ampicillin (Amp)/chloramphenicol (CAM) (100 mg/L)/(34 mg/L) and grown overnight, shaking at 37° C. at 280 RPM.

On the fifth day, a 10 ml starter culture was inoculated into 500 ml LB/Amp/CAM and grown to an OD600 of 0.4. Protein expression was then induced with 0.3 mM concentration of IPTG (isopropyl-β-D-thiogalactopyranoside), using 150 μl of 1M IPTG in 500 ml culture. The cells were spun down at 5,000 rpm for 8 minutes and 10 mL Buffer Z (8M urea, 20 mM Hepes, 100 mM NaCl) containing 15 mM imidazole was added. The cells were then sonicated three times for 25 seconds at an amplitude of 40. The samples were spun down at 13,000 rpm for 10 minutes and the supernatant is combined with 1 ml settled BD TALON™ Metal Affinity Resin (BD Biosciences Clontech, Catalog No 635502) and rocked overnight at 4° C.

The resin/cell lysate slurry is then placed into an empty 0.8×4 cm chromatography column and the resin bed is allowed to settle. The liquid was allowed to run through and the resin bed was washed with 10 bed volumes (10 mL) of Buffer Z containing 15 mM imidazole. Once the 10 mL wash has run through, the His-tag protein was eluted with 3 bed volumes (3 mL) of Buffer Z containing 250 mM imidazole. The resulting sample contained the purified protein of interest. The sample was then desalted into Buffer Z (without imidazole) using a PD-10 desalting column (Amersham Biosciences, Catalog No. 17-0851-01). The resulting imidazole-free sample is quantified and diluted to a concentration of 10 μg/mL which is ready to be used to bind to BIO-PLEX beads for testing.

Example 3

Preparation of Bio-Plex Beads

LIQUICHIP™ Ni-NTA beads (Qiagen Inc., Valencia, Calif.) were used to bind His-tagged purified proteins in the BIO-PLEX assay, but had to be prepared before use. First, the protein samples were desalted into Buffer Z that does not contain Imidazole using Amersham PD-10 desalting columns (Amersham Biosciences Corp, Piscataway, N.J.). The protein was then quantified using a BCA assay and diluted to a concentration of 10 μg/ml with Buffer Z. The LIQUICHIP™ Ni-NTA Bead stock was then vortexed for 30 seconds at full speed. Next, 50 μl of bead suspension was pipetted out and placed into a 1.5 ml microcentrifuge tube. His-tagged protein dilution (50 μl) was then added to the 50 μl LIQUICHIP™ Bead suspension. The beads were then incubated at 4° C. in the dark from at least 4 hours to overnight. Buffer (900 μl PBS/BSA (10 mM $NaH_2PO_4$, 150 mM NaCl, 0.1% BSA pH 7.4)) was then added to the protein-coupled LIQUICHIP™ Bead suspension, adding 0.5% azide as a preservative.

Example 4

Preparation of Positive Controls

Positive and negative controls were used in the BIO-PLEX analysis of *T. cruzi* antigens. The positive control consists of proteins from a *T. cruzi* lysate coupled to LIQUICHIP™ Carboxy Beads. The beads thus contain a mix of *T. cruzi* proteins bound to their surface, and function as a general antigen mix. The LIQUICHIP™ Carboxy Beads bind to the proteins in a random manner, forming covalent bonds to amine groups in lysine side chains. The first step in the preparation of positive controls was the activation of Carboxy Beads using EDC/NHS. First, approximately 10 mg each of EDC (N-(3-dimethylaminopropyl)-N'-ethylcarbodiimide (Fluka catalog No. 03449)) and NHS (N-hydroxysulfosuccinimide (Fluka catalog No. 56485)) were weighed into two microcentrifuge tubes. The LIQUICHIP™ CarboxyBead suspension (1 ml) was then centrifuged for 5 minutes at 10,000 rpm in a microcentrifuge. The supernatant was removed with a 200 μl pipette and discarded. The beads were then washed twice by adding 80 μl of activation buffer and centrifuged for 5 minutes at 10,000 rpm. The supernatant was then carefully removed. Activation buffer (80 μl) was then added to the bead pellet at the bottom of the tube. The pellet should not be resuspended. The pellet in activation buffer was then vortexed for at least 2 minutes. De-ionized water was then added to the weighed EDC and NHS aliquots to provide solutions with a concentration of 50 mg/ml. NHS solution (10 μl) and EDC solution (10 μl) were then added to the bead suspension, which was then incubated for 20 minutes in the dark. Finally, the beads were centrifuged for 5 minutes at 10,000 rpm, after which the supernatant was removed and discarded.

The activated beads were then coupled to the *T. cruzi* lysate. First, the *T. cruzi* pellet was freeze/thawed about 5 times. Insoluble particles were removed by centrifugation. The protein stock was then diluted with coupling buffer to a concentration of 100 µl/ml and a volume of 500 µl. Any foreign protein, azide, glycine, Tris, or other reagent containing primary amine groups present in the protein preparation should be removed by dialysis or gel filtration. Coupling buffer (500 µl) was then added to the beads, which were then resuspended by vortexing. The beads were then washed twice by adding 500 µl of coupling buffer, centrifuging for 5 minutes at 10,000 rpm, removing the supernatant, and then repeating the process. Diluted protein solution (500 µl), prepared earlier, was then added. Next, the tube containing the activated beads and the protein solution was gently agitated on a shaker for 2 hours in the dark at room temperature. The beads were then washed twice with PBS/BSA buffer. The beads were then resuspended in 500 µl PBS/BSA, and 0.5% azide was added as a preservative. The bead number was then adjusted to provide the desired concentration per microliter.

Example 5

BIO-PLEX Analysis of Proteins

At the start of the analysis, a dilution series of the serum to be tested was prepared on a MILLIPORE 96 well filtration plate. The BIO-PLEX Bead/Protein preparation, prepared according to Example 3, was then added to the wells on a MILLIPORE 96 well filtration plate. When preparing beads according to the normal protocol, 10 µl of bead suspension is sufficient to make a useful data point. However when testing beads in which multiple proteins are bound to an individual bead, it may be necessary to combine the beads into a single tube and distribute them to wells so that enough of each bead is present in a given well to give an accurate data point. Controls are preferably included for each sample (sera/protein) being analyzed. For example, the BIO-PLEX analysis for *T. cruzi* antigens included a bead coated with ovalbumin (OVA) as a negative control and with *T. cruzi* lysate as a positive control.

To prepare for the BIO-PLEX analysis, 30 µl of PBS/BSA buffer and 10 µl of an individual bead suspension (or a predetermined volume containing multiple beads each with different proteins bound) were added to the MILLIPORE 96 well filtration plate. The filtration plate was then placed on the vacuum manifold and the sample liquid was pulled through the plate. Next, 50 µl of PBS/BSA and 50 µl of serum dilution were added. The beads were then incubated for 1 hour at room temperature while being shaken on a plate shaker. Each well was then washed four times with 200 µl PBS/BSA to remove any unbound IgG antibodies from the well. PBS/BSA buffer (90 µl) was then added to each well and beads that had settled to the bottom of the filtration plate well due to washing were resuspended. An aliquot (10 µl) of the secondary reporter molecule was then added. This provided a 1:30 dilution (0.5 mg/ml) of antibody. A higher dilution may be used, but a 1:30 dilution makes sure that secondary antibody is not limited by residual unbound IgG. The solution was then incubated for 1 hour at room temperature while being shaken.

The assay solution was then drawn into the BIO-PLEX array reader, which illuminates and reads the sample. When a red diode "classification" laser (635 nm) in the BIO-PLEX array reader illuminates a dyed bead, the bead's fluorescent signature identifies it as a member of one of the 100 possible sets. BIO-PLEX Manager software correlates each bead set to the assay reagent that has been coupled to it. In this way the BIO-PLEX system can distinguish between the different assays combined within a single microplate well. A green "reporter" laser (532 nm) in the array reader simultaneously excites a fluorescent reporter tag (phycoerythrin, or PE) bound to the detection antibody used in the assay. The amount of green fluorescence is proportional to the amount of analyte captured in the immunoassay. Extrapolating to a standard curve allowed quantitation of the analyte in each sample. The results for specific proteins are described in Example 8, and shown in FIG. 4-6.

Example 6

BIO-PLEX Assay of VV-Ovalbumin Sera

Figure 3A:
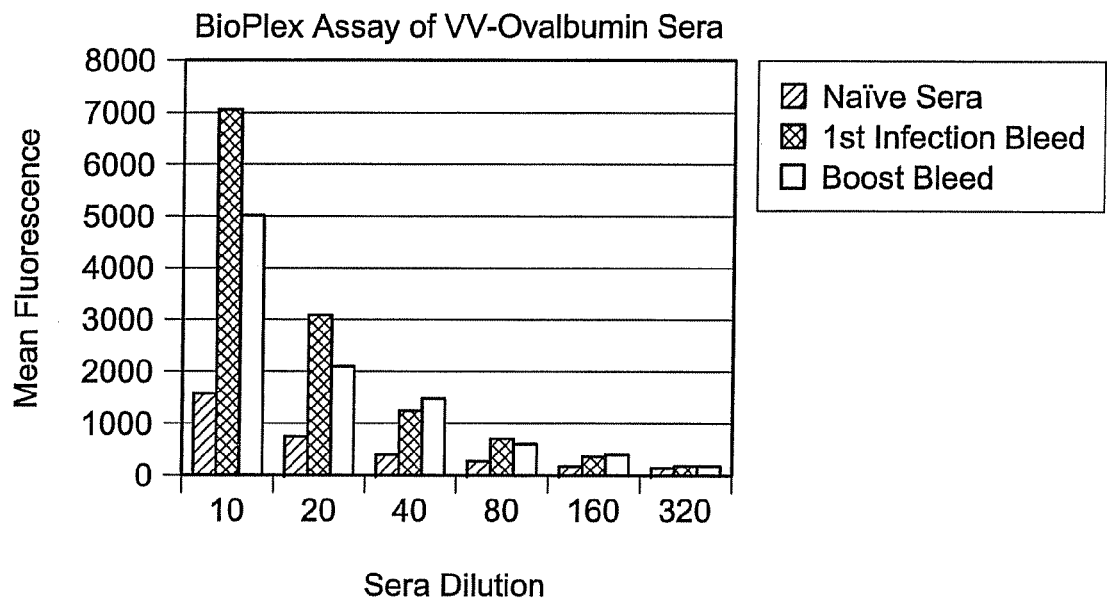
FIG. 3 shows assay development using varicella voster (VV)-ovalbumin sera; A, BIO-PLEX assay; B, ELISA assay.

Ovalbumin (OVA) chosen as the protein antigen to develop the BIO-PLEX method. Mice were infected with Vaccinia virus (VV) containing the OVA gene in order to raise serum antibodies to the protein. Sera was collected at 7 days post infection, followed by a boost and an additional sera collection 7 more days later. OVA protein was expressed in *E. coli* and purified using a His-tag and bound to BIO-PLEX beads via a Ni-NTA residue and adsorbed to an ELISA plate for analysis. The sera was diluted and tested using the BIO-PLEX Assay described in Example 5. The results are shown in FIG. 3A. The results obtained were very comparable to those obtained using ELISA, as described in Example 7.

Example 7

ELISA Assay of VV-Ovalbumin Sera

Figure 3B:
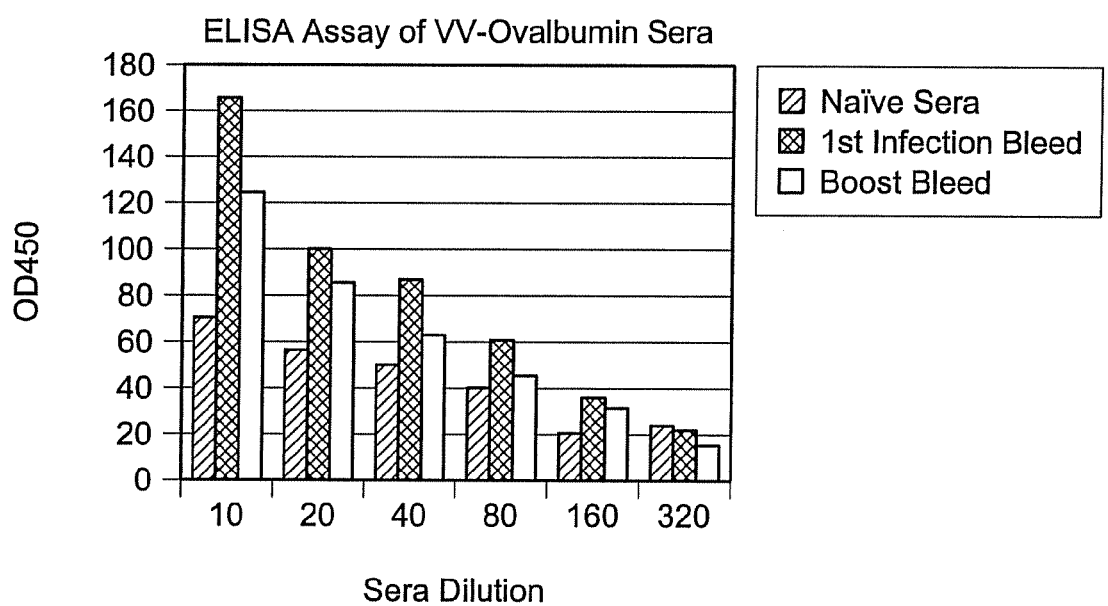

A comparison assay on the ovalbumin of mice infected with Vaccinia virus was run using the ELISA (Enzyme-linked Immunosorbent Assay) method. First, a 96-well polystyrene Immunolon microtiter plate (Dynex Technologies, Chantilly, Va.) was coated with 100 µl of 10 µg/ml ovalbumin (OVA) in PBS overnight at 4° C. or 2 hours at 37° C. The wells were then washed three times with PBS-T (PBS-Tween 20 buffer) and then blocked with 1% BSA for 2 hours. Serum dilutions were then added to each well and the wells were incubated for 2 hours at room temperature or overnight at 4° C. After incubation, the wells were washed five times with PBST. Biotinylated secondary mouse antibody (1:100 dilution) was then added and the wells were allowed to set for 1 hour at room temperature. The wells were then washed again for five times with PBST. Horseradish peroxidase-conjugated streptavidin was then added for 30 minutes at room temperature at a 1:100 dilution. The wells were then washed again five times with PBST. Finally, a developing reagent (2,2'-azido-di-[3-ethylbenzthiazoline sulfonate], ABTS) was added. The results of the ELISA assay of ovalbumin sera are shown in FIG. 3B.

Example 8

BIO-PLEX Assay Results for Pooled and Specific Proteins

Using the method of protein production described in Example 2, over 350 proteins in pools of approximately 10 proteins each were prepared. Each of the pools were screened for antigenicity using the BIO-PLEX technology, as described in Example 5. From the preliminary testing, 11 pools were found to bind readily detectable amounts of antibodies in the sera of *T. cruzi*-infected subjects. These pools were then broken down and each gene was expressed individually and tested. From the over 80 genes expressed, 15 proteins have been confirmed as having serodiagnostic potential.

A Hemagen® Diagnostics Chagas Disease Test Kit (Hemagen Diagnostics, Inc., Columbia, Md.) was used to evaluate and confirm the presence of anti-*T. cruzi* antibodies in sera from areas of active transmission in Argentina. Sera from non-endemic uninfected in-house sera served as the negative controls. Sera from 4 individuals from areas of active transmission, all of which have tested seronegative using standard assays but 1 of which tests positive for T cell reactivity to *T. cruzi*, were used for the very low positive control. Sera from 5 individuals that were borderline positive/negative using standard serological assays were used to make up the borderline positive control and sera from 7 individuals that were consistently seropositive using standard serological assays make up the strong positive control.

Figure 2:
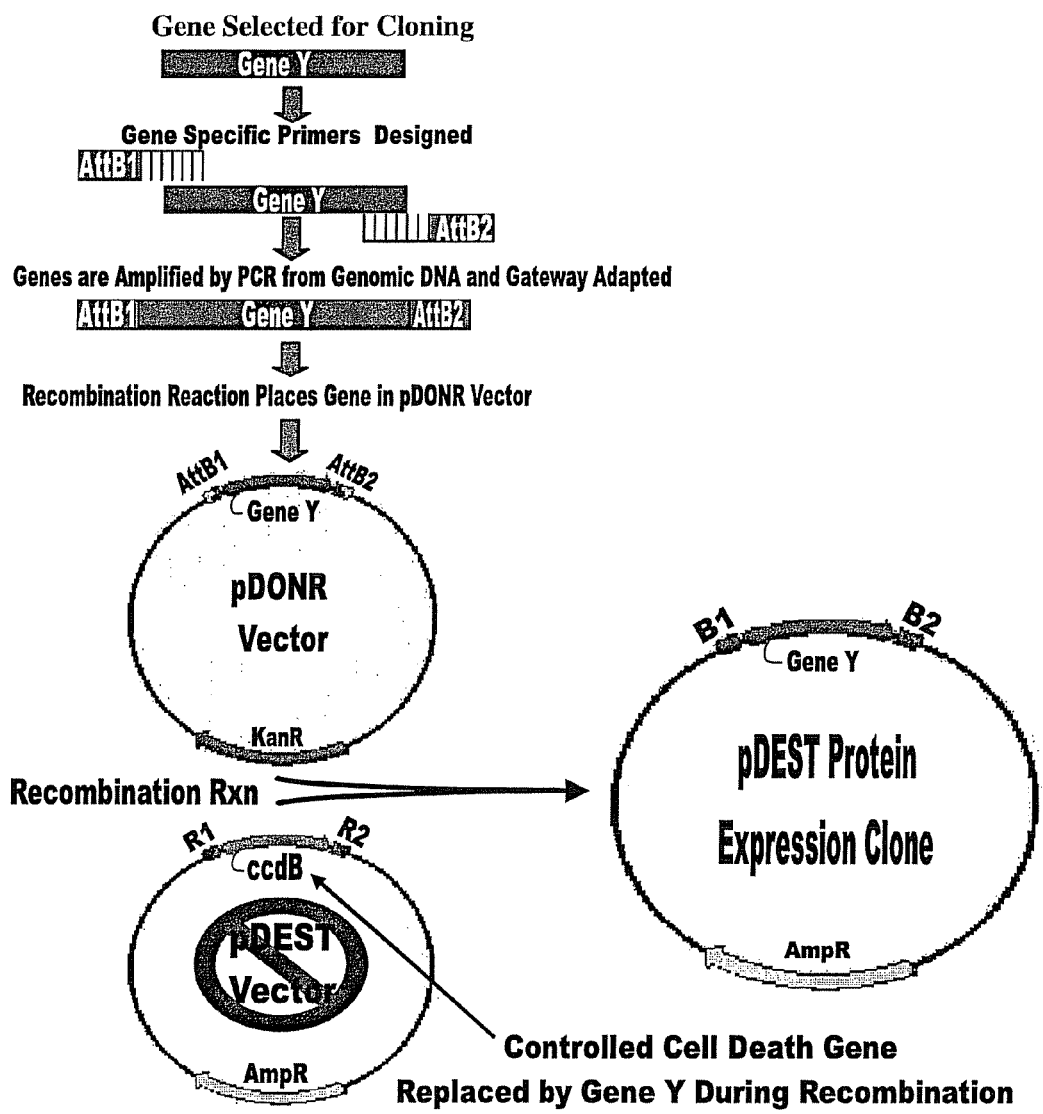
FIG. 2 provides a pictoral overview of the GATEWAY® cloning method used to provide an expression vector used for the preparation of *T. cruzi* polypeptide antigens in one embodiment of the invention.
Figure 4A:
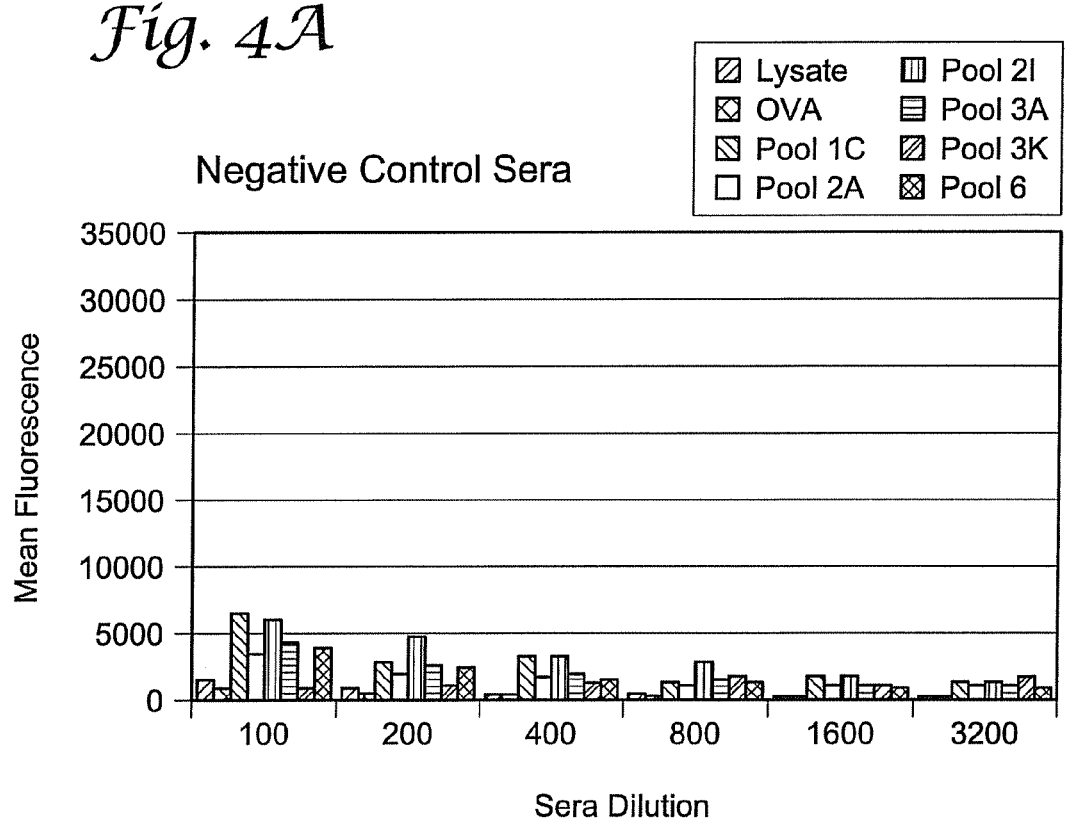
FIG. 4 shows testing of protein pools for antigenic potential using A, negative control sera; B, very low positive sera; C, borderline positive sera; and D, strong positive sera. From left to right, in each panel at each of the sera dilutions, the tested samples are: lysate control, ovalbumin, pool 1C, pool 2A, pool 2I, pool 3A, pool 3K and pool 6. Pool 3K reacted with antibodies from infected individuals and was a candidate for further testing.
Figure 4B:
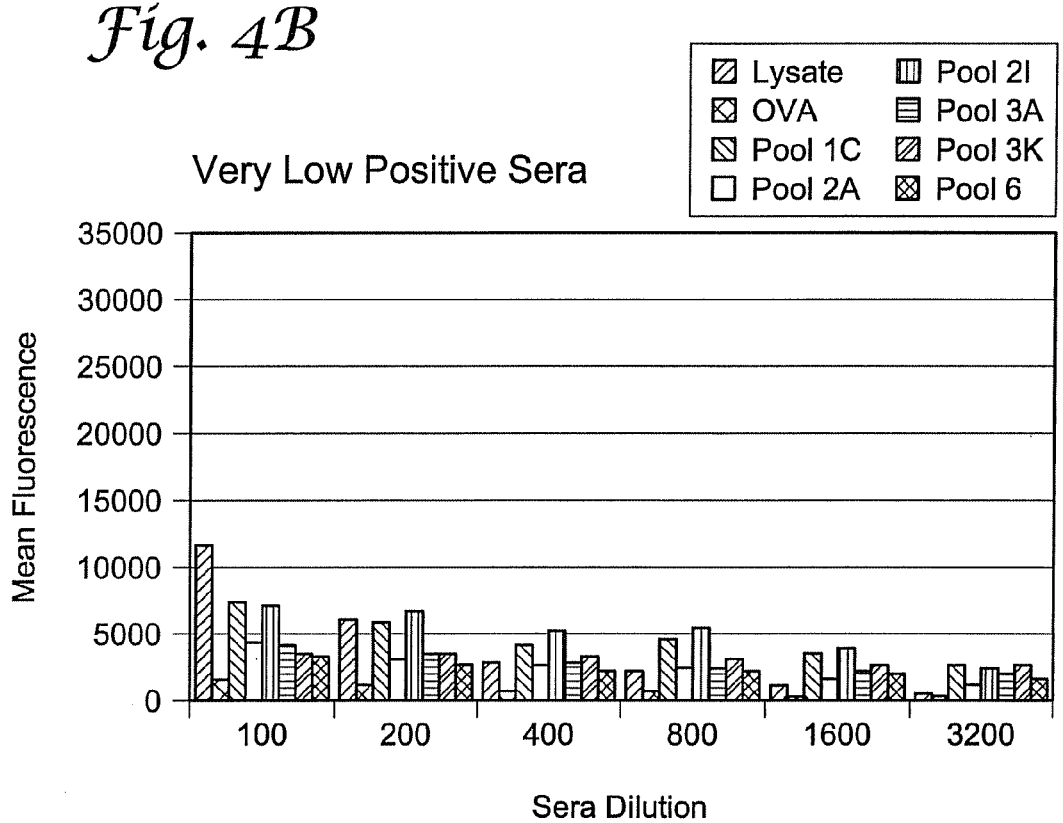
Figure 4C:
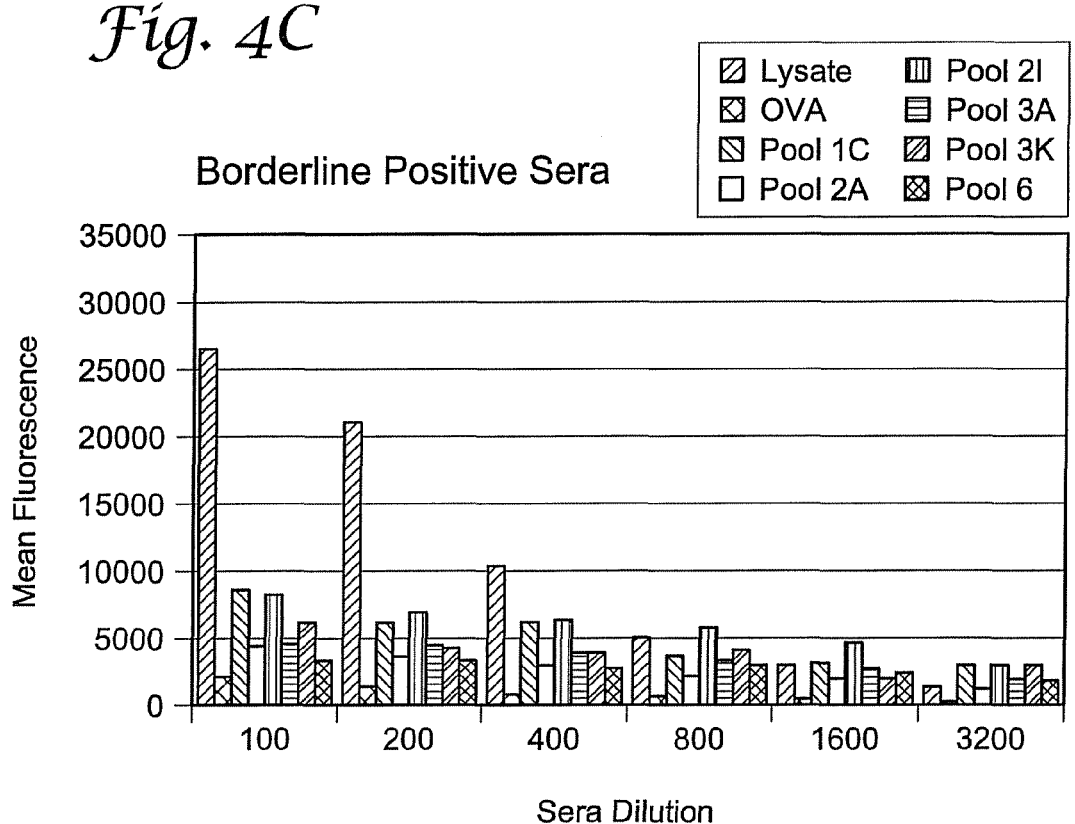
Figure 4D:
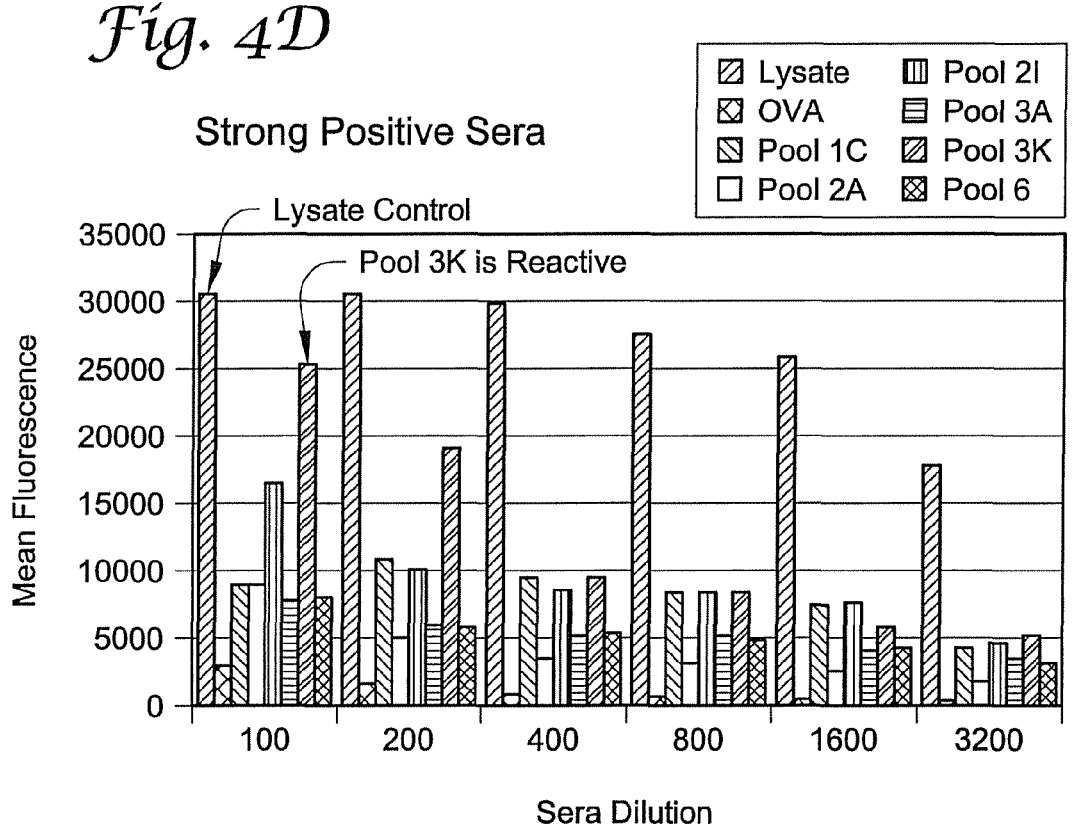

Genes of interest were first cloned into the GATEWAY® holding vectors (pDONR™ vector) and archived as single vectors or are placed into pools. Pools of genes in pDONR™ vectors can be moved simultaneously into either DNA vaccination vectors or protein expression vectors without the loss of individual genes in the pool. The resulting pools were expressed in *E. coli* strain BL21(DE3)pLysS cells, minimizing the possible toxic effects of individual genes. The protein pools are purified and tested using the BIO-PLEX bead technology for antigenicity. The results from analysis of the protein pools using the BIO-PLEX analysis method are shown in FIGS. 4A-2D. The headings in the figures indicate the type of sera being tested, based on the four categories (negative, very low positive, borderline positive, and strong positive) resulting from the evaluation using the Hemagen® Test Kit. As indicated by the arrow, FIG. 4D demonstrates a pool that shows high fluorescence, and hence contains a high level of protein that binds to *T. cruzi*-specific antibodies.

Figure 5A:
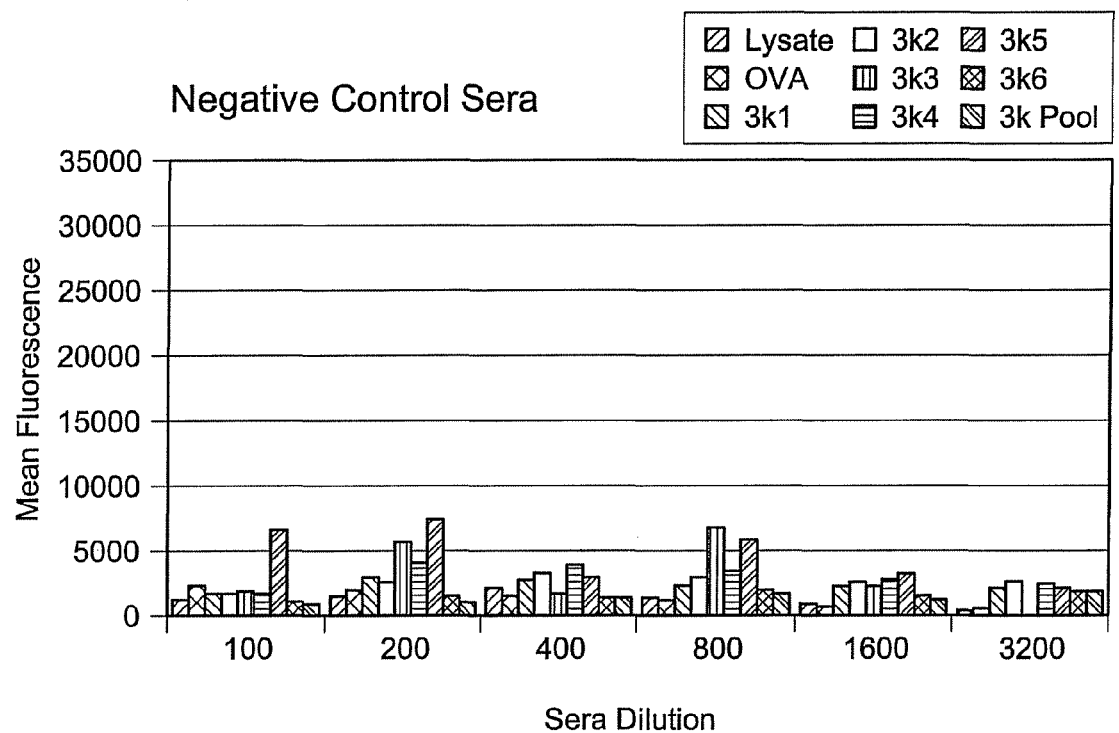
FIG. 5 shows testing of the component proteins of pool 3K for antigenic potential using A, negative control sera; B, very low positive sera; C, borderline positive sera; and D, strong positive sera. From left to right, in each panel at each of the sera dilutions, the tested samples are: lysate control, ovalbumin, protein 3K-1, 3K-2, 3K-3, 3K-4, 3K-5 and 3K-6, and pool 3K. Proteins 3K-1, 3K-2, 3K-3 and 3K-5 demonstrated varying degrees of reactivity to antibodies in sera from infected individuals.
Figure 5B:
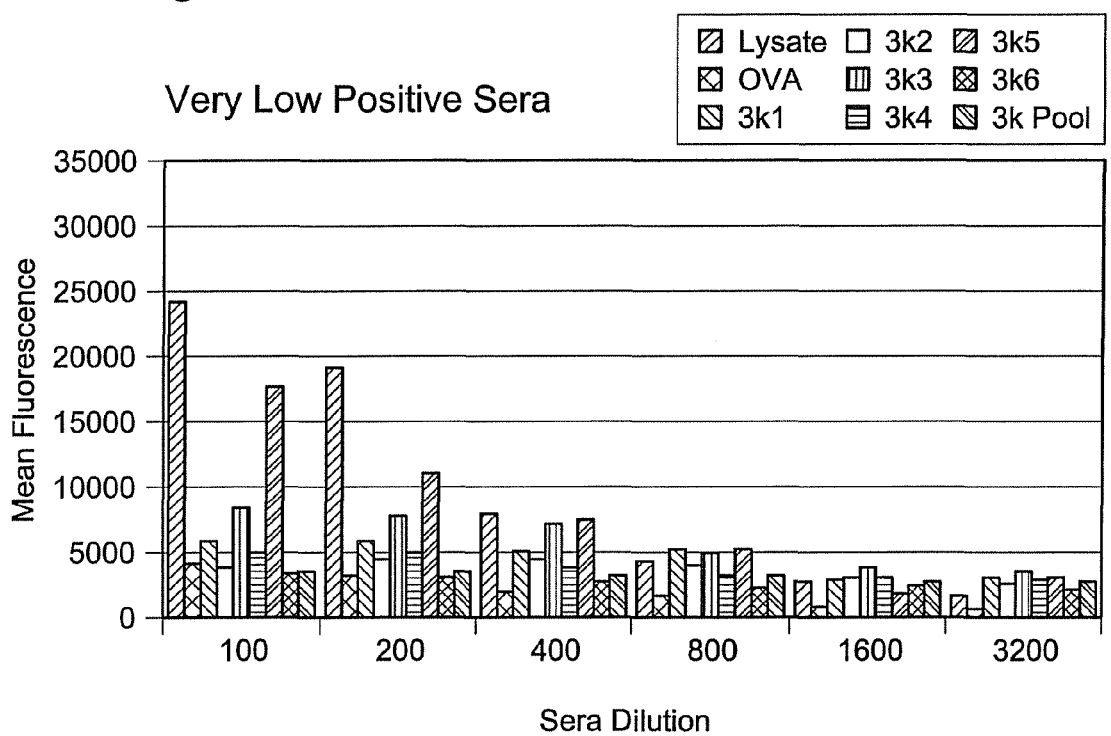
Figure 5C:
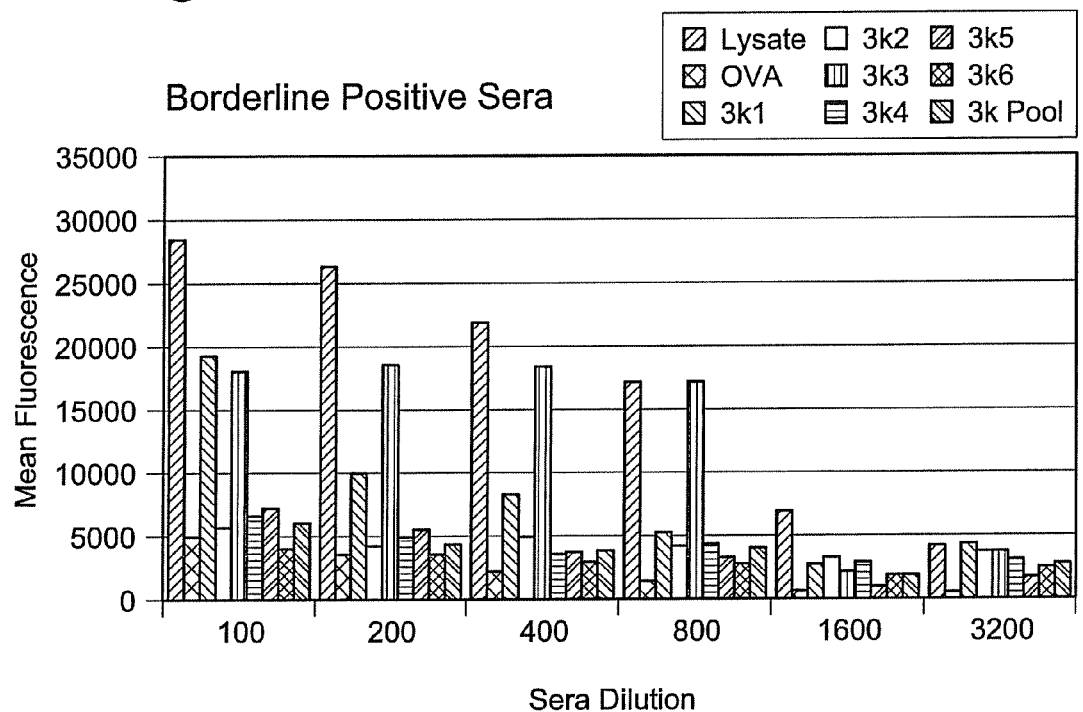
Figure 5D:
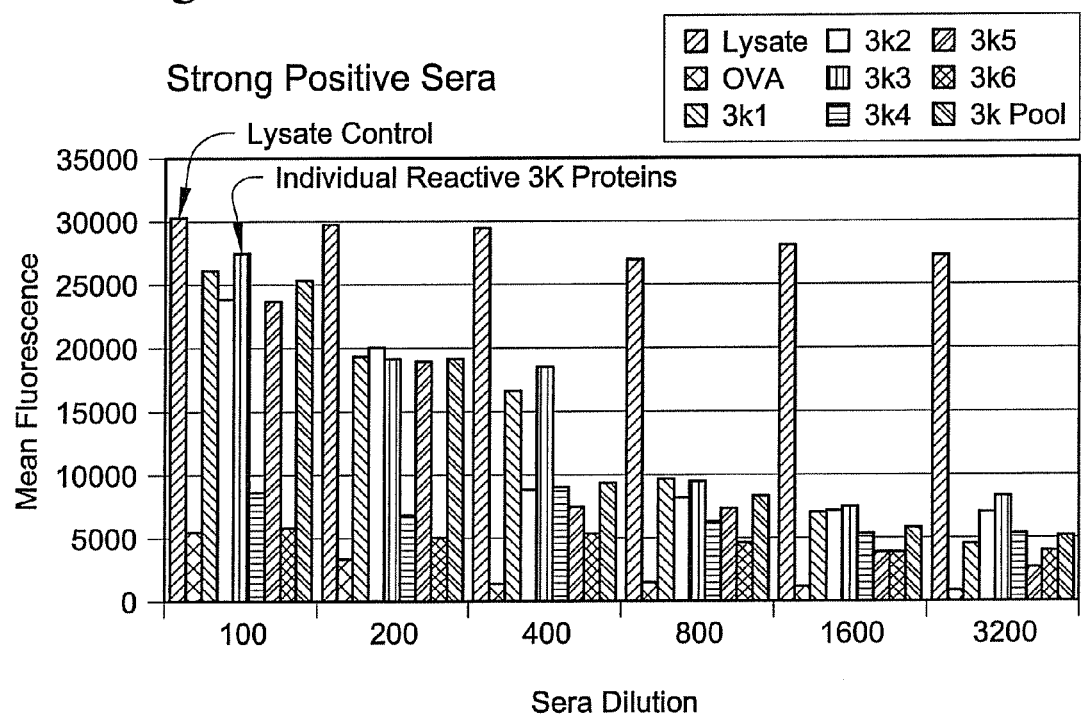
Figure 6A:
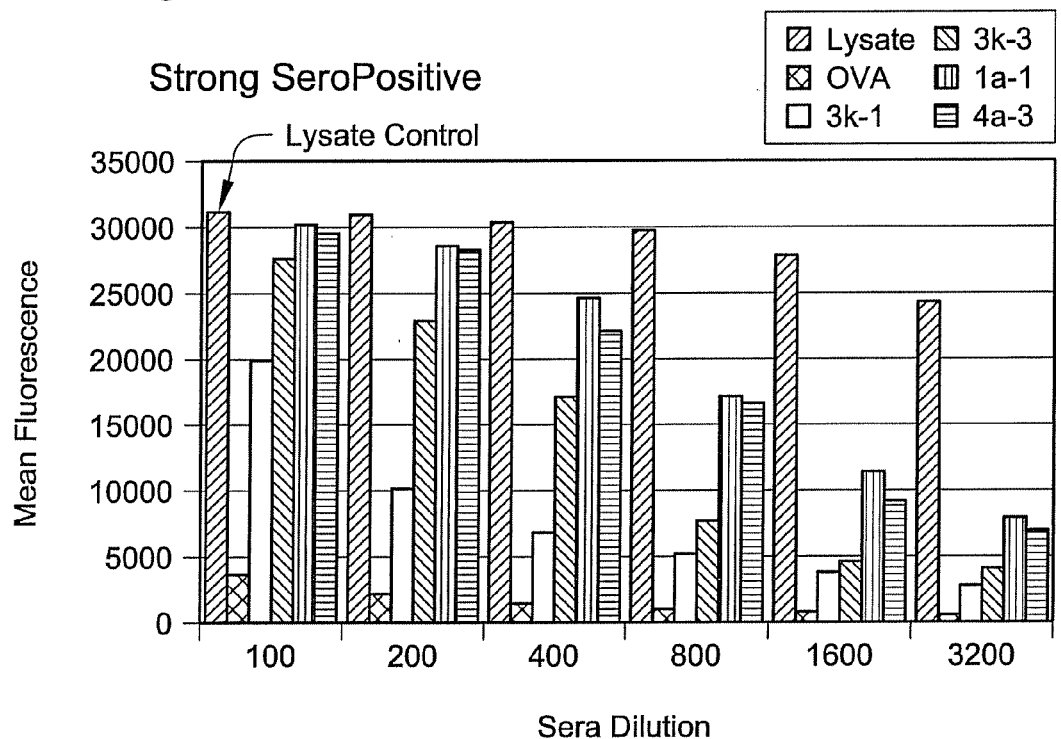
Figure 6B:
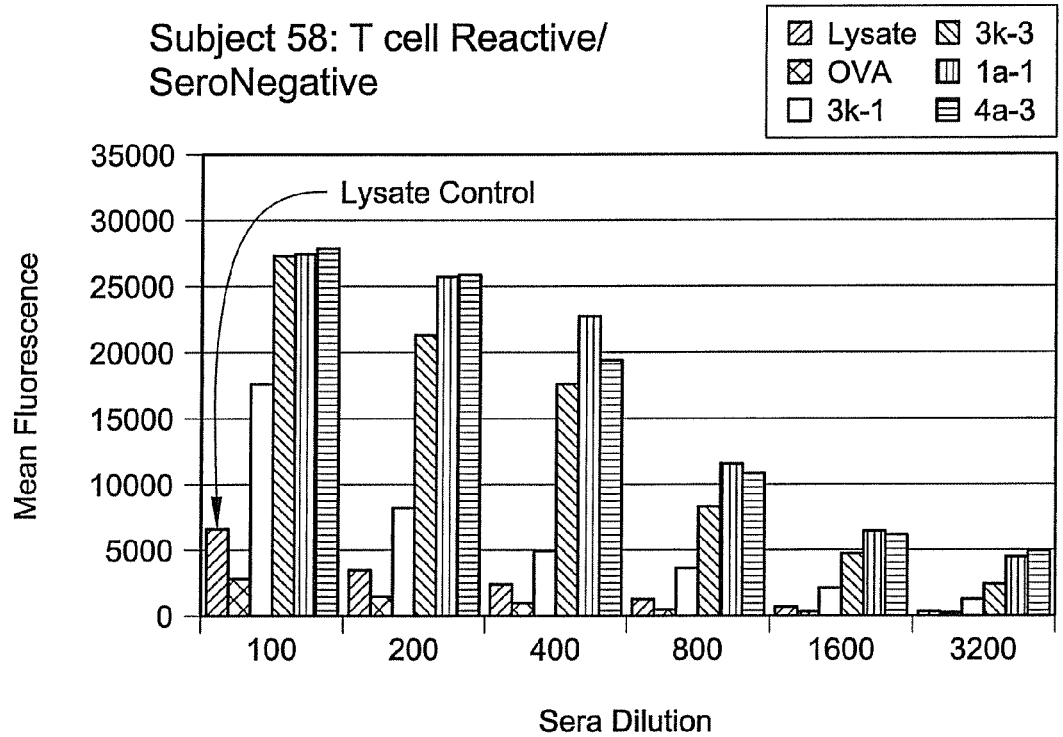
Figure 6C:
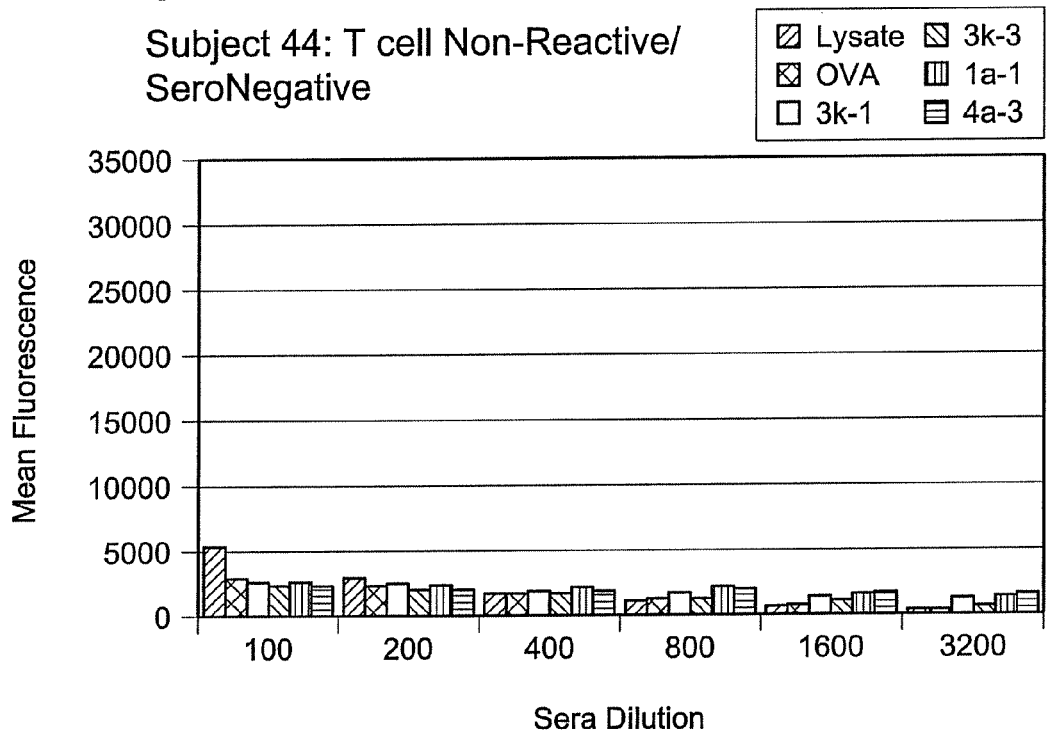
Figure 6D:
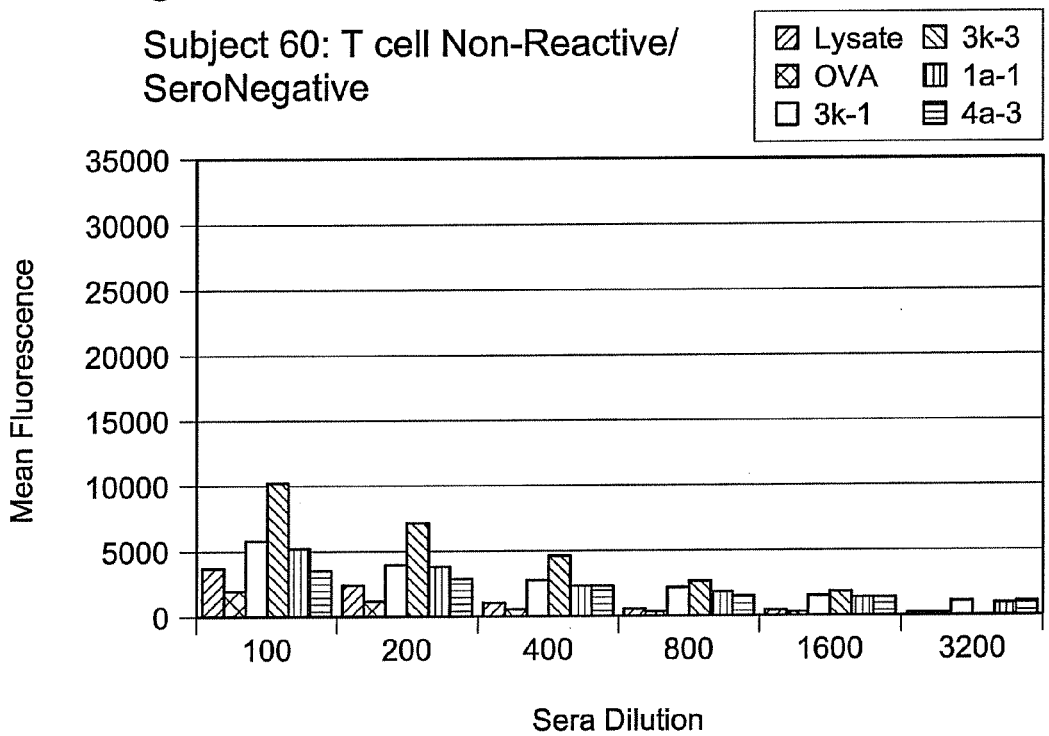

Once a pool of proteins was identified using the BIO-PLEX screening method as having possible antigenic properties, the individual genes in the pool were examined and tested to find which ones provided reactive antigens. The genes were first moved individually from the pDONR holding vector into an expression vector, followed by expression, purification and testing. Those proteins that exhibit binding to antibodies in infected individuals were then retested for confirmation and identified. The results of screening the pools for individual identified. The results of screening the pools for individual proteins is shown in FIGS. 5A-5D. The arrow in FIG. 5D shows a particular protein that reacted strongly with anti-*T. cruzi* antibodies present in strong positive sera.

From the proteins that were screened, many that showed antigenic activity were proteins that had been previously characterized as *T. cruzi* antigens. This provides a level of proof to the capacity of this technique to discover single antigens in pools. Selected ribosomal proteins, ubiquitin, calcium binding proteins, and paraflagellar rod proteins have all been described previously as being possible targets for serological diagnosis of *T. cruzi* infection. A list of the individual proteins identified as *T. cruzi* antigens using the BIO-PLEX screening method are shown below. The "Gene ID numbers" represent gene numbers assigned by annotators of the *T. cruzi* genome and are accessed via the *T. cruzi* genome database on the worldwide web at "TcruziDB.org."

| Assay Protein ID | Protein | Gene ID numbers |
| --- | --- | --- |
| 1a-1 | Tc beta-tubulin | 6998.t00004 |
| 1a-5 | Tc alpha tubulin | 11788.t00001 |
| 1c-3 | 60S ribosomal protein L2, putative | 5568.t00006 |
| 2b-3 | hypothetical protein, conserved | 6986.t00046 |
| 2c-1 | cytochrome C oxidase subunit IV, putative | 6986.t00036 |

-continued

| Assay Protein ID | Protein | Gene ID numbers |
| --- | --- | --- |
| 2c-9 | hypothetical protein | 6986.t00061 |
| 2i-1 | hypothetical protein, conserved | 6003.t00005 |
| 3d-3 | iron superoxide dismutase, putative | 5781.t00004 |
| 3d-4 | trans-splicing factor, putative | 4650.t00004 |
| 3j-1 | 60S ribosomal protein L28, putative | 6890.t00027 |
| 3k-1 | glycosomal phosphoenolpyruvate carboxykinase, putative (Phosphoenolpyruvate Carboxykinase (Pepck)) | 7730.t00002 |
| 3k-2 | ubiquitin-fusion protein, putative (polyubiquitin/ribosomal protein CEP52) | 7355.t00001 |
| 3k-3 | 60S acidic ribosomal subunit protein, putative (Calmodulin-ubiquitin associated protein CUB2.8) | 7695.t00025 |
| 3k-5 | ef-hand protein 5, putative | 6925.t00003 |
| 4a-3 | paraflagellar rod protein 3 | 8152.t00002 |
| B1 | axoneme central apparatus protein, putative | 8553.t00004 |
| B2 | serine carboxypeptidase (CBP1), putative | 8171.t00022 |
| B5 | aminopeptidase, putative | 8647.t00003 |
| B7 | elongation factor-1 gamma, putative | 8322.t00002 |
| B8 | hypothetical protein, conserved | 6987.t00002 |
| D3 | hypothetical protein, conserved | 6967.t00003 |

Research to improve serological diagnosis techniques has focused on the identification, characterization and cloning of particular *T. cruzi* antigens that elicit a strong B cell response. The use of *T. cruzi* specific antigens in a serological test gives a high level of specificity to a serological test, eliminating the problems that arise due to cross-reactivity to a parasite lysate. However using only a single antigen may not be sensitive enough to detect all individuals that are infected, and thus the use of multiple antigens is preferred. Recent evidence demonstrates that some individuals declared negative by current serological tests in fact respond to parasite lysate by producing IFN-γ in ELISPOT assays. These individuals therefore have T cells that have been exposed to parasite antigen, but have a poor B cell antibody response to the antigens in the serological tests that use parasite lysate. The ability to evaluate the T cell reactivity of individual proteins to sera from various subjects using the BIO-PLEX analysis is shown in FIG. 6A-6D.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. An article comprising:

a substrate; and a plurality of different individually addressable antigenic *T. cruzi* polypeptides selected from the polypeptides depicted in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, and SEQ ID NO:21, wherein said polypeptides are immobilized onto a surface of said substrate.

2. The article of claim 1 wherein the polypeptides are immobilized on the substrate surface to form a microarray.

3. The article of claim 1 wherein the substrate comprises at least one nanoparticle, and wherein the polypeptides are immobilized on the surface of the nanoparticle.

4. A kit for diagnosis of *T. cruzi* infection comprising:

an article comprising a substrate and a plurality of different individually addressable antigenic *T. cruzi* polypeptides selected from the polypeptides depicted in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEP ID NO:14, SEQ ID NO:15, SEQ ID NO:16, SEQ ID NO:17, SEQ ID NO:18, SEQ ID NO:19, SEQ ID NO:20, and SEQ ID NO:21, wherein said polypeptides are immobilized onto a surface of said substrate; and packaging materials and instructions for use.

5. A method for detecting contamination of a blood product supply with *T. cruzi*, the method comprising:

selecting a sample from the blood supply;

contacting the sample with the article of claim 1; and evaluating the presence, absence, intensity or pattern of interaction of components of the sample with the immobilized antigenic *T. cruzi* polypeptides to determine whether the blood supply is contaminated with *T. cruzi*.

6. The method of claim 5 wherein the blood product supply comprises whole blood, a blood product, or a blood fraction.

7. The method of claim 5 wherein the blood product supply comprises a cellular blood component, a liquid blood component, a blood protein, or mixtures thereof.

8. The method of claim 5 wherein the blood product supply comprises a red blood cell concentrate, a leukocyte concentrate, a platelet concentrate, plasma, serum, a clotting factor, an enzymes, albumin, plasminogen, or a immunoglobulin, or mixtures of thereof

9. The method of claim 5 wherein the method is a serodiagnostic method, and wherein the sample component that interacts with the immobilized antigenic *T. cruzi* polypeptides is an antibody.

10. The method of claim 5 wherein the method is a cellular assay method, and wherein the sample component that interacts with the immobilized antigenic *T. cruzi* polypeptides is T cell.

* * * * *

SEQUENCE LISTING

<160> NUMBER OF SEQ ID NOS: 21

<210> SEQ ID NO 1
<211> LENGTH: 442
<212> TYPE: PRT
<213> ORGANISM: Trypanosoma cruzi

<400> SEQUENCE: 1

```
Met Arg Glu Ile Val Cys Val Gln Ala Gly Gln Cys Gly Asn Gln Ile
1               5                   10                  15

Gly Ser Lys Phe Trp Glu Val Ile Ser Asp Glu His Gly Val Asp Pro
            20                  25                  30

Thr Gly Thr Tyr Gln Gly Asp Ser Asp Leu Gln Leu Glu Arg Ile Asn
        35                  40                  45

Val Tyr Phe Asp Glu Ala Thr Gly Gly Arg Tyr Val Pro Arg Ala Val
    50                  55                  60

Leu Ile Asp Leu Glu Pro Gly Thr Met Asp Ser Val Arg Ala Gly Pro
65                  70                  75                  80

Tyr Gly Gln Ile Phe Arg Pro Asp Asn Phe Ile Phe Gly Gln Ser Gly
                85                  90                  95

Ala Gly Asn Asn Trp Ala Gln Gly His Tyr Thr Glu Gly Ala Glu Leu
            100                 105                 110

Ile Asp Ser Val Leu Asp Val Cys Arg Lys Glu Ala Glu Ser Cys Asp
        115                 120                 125

Cys Leu Gln Gly Phe Gln Ile Cys His Ser Leu Gly Gly Gly Thr Gly
    130                 135                 140

Ser Gly Met Gly Thr Leu Leu Ile Ser Lys Leu Arg Glu Glu Tyr Pro
145                 150                 155                 160

Asp Arg Ile Met Met Thr Phe Ser Ile Ile Pro Ser Pro Lys Val Ser
                165                 170                 175

Asp Thr Val Val Glu Pro Tyr Asn Thr Thr Leu Ser Val His Gln Leu
            180                 185                 190

Val Glu Asn Ser Asp Glu Ser Met Cys Ile Asp Asn Glu Ala Leu Tyr
        195                 200                 205

Asp Ile Cys Phe Arg Thr Leu Lys Leu Thr Thr Pro Thr Phe Gly Asp
    210                 215                 220

Leu Asn His Leu Val Ser Ala Val Ser Gly Val Thr Cys Cys Leu
225                 230                 235                 240

Arg Phe Pro Gly Gln Leu Asn Ser Asp Leu Arg Lys Leu Ala Val Asn
                245                 250                 255

Leu Val Pro Phe Pro Arg Leu His Phe Phe Met Met Gly Phe Ala Pro
            260                 265                 270

Leu Thr Ser Arg Gly Ser Gln Gln Tyr Arg Gly Leu Ser Val Pro Glu
        275                 280                 285

Leu Thr Gln Gln Met Phe Asp Ala Lys Asn Met Met Gln Ala Ala Asp
    290                 295                 300

Pro Arg His Gly Arg Tyr Leu Thr Ala Ser Ala Leu Phe Arg Gly Arg
305                 310                 315                 320

Met Ser Thr Lys Glu Val Asp Glu Gln Met Leu Asn Val Gln Asn Lys
                325                 330                 335

Asn Ser Ser Tyr Phe Ile Glu Trp Ile Pro Asn Asn Ile Lys Ser Ser
            340                 345                 350

Ile Cys Asp Ile Pro Pro Lys Gly Leu Lys Met Ala Val Thr Phe Val
```

-continued

```
                355                 360                 365
Gly Asn Asn Thr Cys Ile Gln Glu Met Phe Arg Arg Val Gly Glu Gln
        370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Tyr Gln Asp Ala Thr Ile Glu Glu
                420                 425                 430

Glu Gly Glu Phe Asp Glu Glu Glu Gln Tyr
        435                 440

<210> SEQ ID NO 2
<211> LENGTH: 451
<212> TYPE: PRT
<213> ORGANISM: Trypanosoma cruzi

<400> SEQUENCE: 2

Met Arg Glu Ala Ile Cys Ile His Ile Gly Gln Ala Gly Cys Gln Val
1               5                   10                  15

Gly Asn Ala Cys Trp Glu Leu Phe Cys Leu Glu His Gly Ile Gln Pro
            20                  25                  30

Asp Gly Ala Met Pro Ser Asp Lys Thr Ile Gly Val Glu Asp Asp Ala
        35                  40                  45

Phe Asn Thr Phe Phe Ser Glu Thr Gly Ala Gly Lys His Val Pro Arg
    50                  55                  60

Ala Val Phe Leu Asp Leu Glu Pro Thr Val Val Asp Glu Ile Arg Thr
65                  70                  75                  80

Gly Thr Tyr Arg Gln Leu Phe His Pro Glu Gln Leu Ile Ser Gly Lys
                85                  90                  95

Glu Asp Ala Ala Asn Asn Tyr Ala Arg Gly His Tyr Thr Ile Gly Lys
            100                 105                 110

Glu Ile Val Asp Leu Cys Leu Asp Arg Ile Arg Lys Leu Ala Asp Asn
        115                 120                 125

Cys Thr Gly Leu Gln Gly Phe Leu Val Tyr His Ala Val Gly Gly Gly
    130                 135                 140

Thr Gly Ser Gly Leu Gly Ala Leu Leu Leu Glu Arg Leu Ser Val Asp
145                 150                 155                 160

Tyr Gly Lys Lys Ser Lys Leu Gly Tyr Thr Val Tyr Pro Ser Pro Gln
                165                 170                 175

Val Ser Thr Ala Val Val Glu Pro Tyr Asn Ser Val Leu Ser Thr His
            180                 185                 190

Ser Leu Leu Glu His Thr Asp Val Ala Ala Met Leu Asp Asn Glu Ala
        195                 200                 205

Ile Tyr Asp Leu Thr Arg Arg Asn Leu Asp Ile Glu Arg Pro Thr Tyr
    210                 215                 220

Thr Asn Leu Asn Arg Leu Ile Gly Gln Val Val Ser Ala Leu Thr Ala
225                 230                 235                 240

Ser Leu Arg Phe Asp Gly Ala Leu Asn Val Asp Leu Thr Glu Phe Gln
                245                 250                 255

Thr Asn Leu Val Pro Tyr Pro Arg Ile His Phe Val Leu Thr Ser Tyr
            260                 265                 270

Ala Pro Val Ile Ser Ala Glu Lys Ala Tyr His Glu Gln Leu Ser Val
        275                 280                 285
```

-continued

```
Ser Glu Ile Ser Asn Ala Val Phe Glu Pro Ala Ser Met Met Thr Lys
    290                 295                 300

Cys Asp Pro Arg His Gly Lys Tyr Met Ala Cys Cys Leu Met Tyr Arg
305                 310                 315                 320

Gly Asp Val Val Pro Lys Asp Val Asn Ala Ala Val Ala Thr Ile Lys
                325                 330                 335

Thr Lys Arg Thr Ile Gln Phe Val Asp Trp Ser Pro Thr Gly Phe Lys
                340                 345                 350

Cys Gly Ile Asn Tyr Gln Pro Pro Thr Val Val Pro Gly Gly Asp Leu
            355                 360                 365

Ala Lys Val Gln Arg Ala Val Cys Met Ile Ala Asn Ser Thr Ala Ile
    370                 375                 380

Ala Glu Val Phe Ala Arg Ile Asp His Lys Phe Asp Leu Met Tyr Ser
385                 390                 395                 400

Lys Arg Ala Phe Val His Trp Tyr Val Gly Glu Gly Met Glu Glu Gly
                405                 410                 415

Glu Phe Ser Glu Ala Arg Glu Asp Leu Ala Ala Leu Glu Lys Asp Tyr
            420                 425                 430

Glu Glu Val Gly Ala Glu Ser Ala Asp Met Glu Gly Glu Glu Asp Val
    435                 440                 445

Glu Glu Tyr
    450

<210> SEQ ID NO 3
<211> LENGTH: 260
<212> TYPE: PRT
<213> ORGANISM: Trypanosoma cruzi

<400> SEQUENCE: 3

Met Gly Lys Thr Val Leu Thr Cys Arg Lys Gly Asn Gly Ser Val Tyr
1               5                   10                  15

Gln Leu His Gly His Lys Arg Leu Gly Pro Ala Lys Leu Arg Ile Leu
            20                  25                  30

Asp Tyr Ala Glu Arg His Gly Phe Met Arg Gly Val Val Lys Thr Ile
        35                  40                  45

Glu His Glu Pro Gly Arg Gly Ala Pro Leu Ala Arg Val Glu Phe Arg
    50                  55                  60

His Pro Tyr Lys Tyr Arg Arg Val Lys Glu Leu Met Val Ala Pro Glu
65                  70                  75                  80

Gly Met Phe Thr Gly Gln Ser Val Leu Cys Gly Val Lys Ala Pro Leu
                85                  90                  95

Ala Ile Gly Asn Val Leu Pro Leu Gly Gln Ile Thr Glu Gly Cys Ile
            100                 105                 110

Val Cys Asn Val Glu Ala Lys Val Gly Asp Arg Gly Thr Ile Ala Arg
        115                 120                 125

Ala Ser Gly Asp Tyr Cys Ile Ile Ile Ser His Asn His Glu Thr Gly
    130                 135                 140

Arg Thr Arg Leu Lys Leu Pro Ser Gly Gln Lys Lys Thr Val Pro Ser
145                 150                 155                 160

Asn Cys Arg Ala Met Ile Gly Ile Ile Ala Gly Gly Arg Ile Glu
                165                 170                 175

Lys Pro Val Leu Lys Ala Gly Asn Ser Phe Tyr Arg Phe Arg Gly Lys
            180                 185                 190

Arg Asn Cys Trp Pro Lys Val Arg Gly Val Ala Arg Asn Pro Val Glu
        195                 200                 205
```

```
His Pro His Gly Gly Asn His Gln His Ile Gly His Pro Ser Thr
    210                 215                 220

Val Ser Arg His Ala Pro Gly Gln Lys Val Gly Leu Ile Ala Ala
225                 230                 235                 240

Arg Arg Thr Gly Arg Ile Arg Gly Ser Arg Ala Val Lys Gly Ala Trp
                245                 250                 255

His Pro Glu Glu
            260

<210> SEQ ID NO 4
<211> LENGTH: 821
<212> TYPE: PRT
<213> ORGANISM: Trypanosoma cruzi

<400> SEQUENCE: 4

Met His Arg Gln Glu Ser Val Ser Gly Gly Gly Asn Ala Thr Gly
1               5                   10                  15

Arg Gly Ser Leu Thr Thr Ala Glu Val Leu Asp Arg Ala Met Asn Gln
            20                  25                  30

Cys Met Gln Arg Gly Leu Phe Asp Thr Ala Ser Trp Leu Gly Gln Leu
        35                  40                  45

Ala Leu Asn Ala Thr Asp Ser Val Leu Arg Asp Ser Ile Ser Ala Thr
    50                  55                  60

Ser Pro Ala Val Ala Ala Leu Gln Asp Pro Pro Leu Thr Gly Arg Ala
65                  70                  75                  80

His Arg Tyr Leu Val Val Ala Leu Ser Leu Met Gln Lys Ser Glu Tyr
                85                  90                  95

Ile Arg Cys His His Glu Leu Asn Ile Ala Leu Lys Glu Phe Ser Ala
            100                 105                 110

Glu Ser Thr Pro Val Glu Ser Glu Lys Cys Ala Arg Asp His Pro Pro
        115                 120                 125

Met Pro Arg Gly Ser Gly Arg Ser Thr Pro Leu Pro Ala Ala Ser Ser
    130                 135                 140

Ser Pro Met Leu Pro Pro Pro Gln Leu Gln Phe Leu Cys Leu Tyr Ser
145                 150                 155                 160

Leu Tyr Met Ala Gly Glu Cys Ile Lys Ser Thr Ser Ser Asn Pro Arg
                165                 170                 175

Lys Ser Ser Asn Pro His Leu Arg Thr Leu Arg Gly Arg Leu Leu Thr
            180                 185                 190

Leu Leu Glu Gln Gln Arg Arg Ser Leu Ser Ser Pro Ala Ser Ile
        195                 200                 205

Lys Ser Ser Met Lys Pro Thr Pro Leu Ser Ser Ala Ser Met Ala Val
    210                 215                 220

Gly Ala Pro Ala Tyr Gly Asp Pro Phe Leu Cys Trp Leu His Gly Val
225                 230                 235                 240

Val Leu Arg Glu Leu Gly Met Lys Gln Glu Ser Ala Thr Tyr Phe Leu
                245                 250                 255

Ala Ala Leu Cys Asn His Pro Met Leu Trp Cys Ala Trp Glu Asp Leu
            260                 265                 270

Cys Thr Leu Val Ser Arg Glu Asn Gln Ile Glu Glu Ile Glu Ala Ile
        275                 280                 285

Ile Ala Ser Leu Glu Pro Arg Phe Met Ser Glu Ile Phe Leu Ala Ser
    290                 295                 300

Ala Lys Ala Ala Leu Asn Val Ala Pro Met Ser Leu Val Pro Pro Ser
```

```
             305                 310                 315                 320
Leu Ser Thr Ala Ala Ala Ala Met Ala Gln Arg Ser Thr Ser Pro
                325                 330                 335
His Cys Gly Ser Leu Pro Arg Gln Thr Thr Ser Thr Leu Glu Thr Gln
                340                 345                 350
Glu Gln His Tyr Arg Pro Gln His Gln Arg Arg Gly Glu Ser Gly
                355                 360                 365
Val Ser Pro Arg Leu Val Asn Ser Trp Glu Ala Leu Leu Glu Arg Phe
    370                 375                 380
Pro Asn Leu Phe Leu Leu Ala Asn Leu Ala Gly Tyr Tyr Asn
385                 390                 395                 400
Val Lys Lys Asp Leu Glu Lys Ala Gln Ser Leu Tyr Lys Arg Leu His
                405                 410                 415
Glu Met Asn Pro Tyr Arg Leu Glu Ser Met Asp Asp Tyr Ser Ile Val
                420                 425                 430
Leu Phe Leu Arg Gly Asp Arg Ile Gly Leu Ser Ser Leu Ala Gln Gln
                435                 440                 445
Val Tyr Gln Ile Asp Pro Phe Arg Ala Glu Ser Asn Tyr Val Val Gly
    450                 455                 460
Asn Tyr Tyr Val Leu Met Gly Ala His Asp Arg Gly Val Leu His Phe
465                 470                 475                 480
Arg Arg Ala Val Ala Ala Asp Pro Thr Phe Leu Ala Ala Trp Thr Leu
                485                 490                 495
Leu Gly His Ala Tyr Leu Glu Thr Lys Asn Ser Ala Ala Ala Val Glu
                500                 505                 510
Ala Tyr Arg Ala Ala Val Asp Leu Asp Pro Arg Asp Tyr Arg Gly Trp
                515                 520                 525
Tyr Asn Leu Gly Gln Ile Tyr Glu Leu Leu Gln Phe Tyr His His Ala
    530                 535                 540
Leu Tyr Tyr Tyr Trp His Thr Thr Leu Arg Pro Thr Asp Pro Arg
545                 550                 555                 560
Met Trp Ser Ala Val Ala Asn Cys Leu Asp Arg Glu Gly Arg Thr Gly
                565                 570                 575
Glu Ala Val Leu Cys Leu Glu Arg Ala Glu Ala His Glu Ser Ser Ser
                580                 585                 590
Ser Asp Tyr Tyr Pro Pro Leu Val His Arg Leu Gly Leu His Tyr Leu
    595                 600                 605
Gly Ile Arg Arg Leu Asp Arg Ala Val Ile Tyr Leu Glu Lys Leu Ala
    610                 615                 620
Leu Ser Glu Ala Arg Arg Arg Glu Asp Val Leu Phe Ala Ile Pro His
625                 630                 635                 640
Val Val Pro Tyr Tyr Leu Gln Gln Ala Arg Gln Leu Leu Asp Ile Pro
                645                 650                 655
Ser Arg Ser Pro Ser Tyr Glu Pro Gln Pro His Ser Thr Thr Ala
                660                 665                 670
Gly Gly Gly Asp Gly Gln Leu Pro Gln Thr Met Ala Ser Ala Met Gly
                675                 680                 685
Ala Thr Asn Ala Ser Thr Gly Gly Asn Val Tyr Arg Ser Ser Leu Ala
    690                 695                 700
Asp Gln Trp Leu Thr Ala Asp Ala Ala Ala Arg Arg Asn Ile Glu Thr
705                 710                 715                 720
Arg Trp Glu Gln Ala Ala Leu Cys Leu Thr Ser Ser Glu Arg His Leu
                725                 730                 735
```

```
Glu Asn Phe Ala Ser Val Leu Gly Ile Pro Val Ala Ser Ala Ala Asp
            740                 745                 750

Asn Gly Ala Arg Lys Ser Thr Glu Tyr Gly Asp Thr Gly Val Ser Gly
        755                 760                 765

Ser Gly Gly Val Ala Gly Val Thr Met Asp Glu Gly Arg Ser Gln His
        770                 775                 780

Thr Leu Gln Leu Ala Cys Leu Tyr Arg Glu Leu Asn Lys Ile Arg Gln
785                 790                 795                 800

Tyr Leu Thr Ser Gln Gln Glu Gln Val Glu Thr Ala Met Arg Met Arg
                805                 810                 815

Gly Gly Gly Asn Ala
            820

<210> SEQ ID NO 5
<211> LENGTH: 334
<212> TYPE: PRT
<213> ORGANISM: Trypanosoma cruzi

<400> SEQUENCE: 5

Met Leu Ser Arg Arg Ser Leu Thr Thr Ala Phe Ala Ala Met Thr Lys
1               5                   10                  15

Gln Pro Leu Met Gln Gln Arg Arg His Asp His Asp Arg Trp Tyr Gly
            20                  25                  30

His Ala Leu Glu Leu Asp Ser His Asn Tyr Lys Phe Thr Gly Glu Pro
        35                  40                  45

Pro Ser Trp Met Arg Gln Arg Glu Arg Thr Glu Glu Glu Thr Ala Phe
    50                  55                  60

Ala Lys Ser Val Leu Pro His Val Asp Phe Ala Ser Ser Tyr Glu Cys
65                  70                  75                  80

Leu Leu Phe Asp Ala Asp Arg Leu Asn Gly His Leu Asn Arg Lys Glu
                85                  90                  95

Phe Gly Asn Glu Val Thr Phe Arg Leu Glu Lys Gln Ser Asn Thr Val
            100                 105                 110

Ala Arg Ala Gln Gln Met Leu Lys Glu Lys Ser Ser Ser Asp Glu
        115                 120                 125

Arg Leu Glu Asn Thr Met Ile Ala Arg Ile Phe Asp Glu Glu His Val
    130                 135                 140

Gln Ala Glu Met Lys Tyr Val Lys Cys Ile Arg Ala Asn Glu Leu Ala
145                 150                 155                 160

Glu Asp Asn Arg Leu Asp Ile Leu Pro Gly Gly Ser Pro Asn Ser Leu
                165                 170                 175

Arg Glu Lys Thr Arg Trp Asn Val Asn Thr Glu Leu His Pro Ala Asp
            180                 185                 190

Arg Ala Glu Ile Gly Ala Arg Leu Thr Ala Trp Leu Pro Glu Lys Tyr
        195                 200                 205

His Ile Val Tyr Phe Asp Asp Phe Gln Thr Val Ala Ala Asn Asp Pro
    210                 215                 220

Ser Ala Arg Arg Glu Met Leu Asn Ile Val Gln Asn Val Glu Arg Glu
225                 230                 235                 240

Tyr Ala Asp Glu Ala Lys Ser Ser Gly Tyr Glu Lys Asp Leu Lys Glu
                245                 250                 255

Val Val Asn Glu Leu Leu Asp Asp Val Asp Pro Ser Arg His Ile Thr
            260                 265                 270

Pro Glu Ala Ile Lys Ala Cys Thr Asp Leu Asn Gln Leu Glu Glu Trp
```

```
                   275                 280                 285
Ser Arg Val Val His Glu Tyr Asn Gly Asp Asp Arg Ile Leu Asp Ile
    290                 295                 300

Tyr Ala Arg Ala Ala Glu Leu Thr Lys Asn Ala Asp His Gln Ala Leu
305                 310                 315                 320

Val Lys Asn Met Lys Glu Trp Arg Lys Leu Ala Asn Lys Ile
                325                 330

<210> SEQ ID NO 6
<211> LENGTH: 404
<212> TYPE: PRT
<213> ORGANISM: Trypanosoma cruzi

<400> SEQUENCE: 6

Met Met Gly Asp Val Asn Asn Val Glu Ala Lys Glu Lys Lys Met Gly
1               5                   10                  15

Tyr Glu Ala Lys Lys Val Pro Val Ser Pro Val Lys Ser Ser Arg Pro
            20                  25                  30

Thr Ala Tyr Val Arg Lys Pro Ala Ser Ala Arg Asn Val Gly Ser Pro
        35                  40                  45

Ser Ala Lys His Asp Ala Leu Ala Ser Phe Thr Ser Pro Arg Asp Ser
    50                  55                  60

Lys Arg His Val Pro Asp Cys Gly Phe Ala Ser Pro His Ser Ser Arg
65                  70                  75                  80

Arg Pro Tyr Arg Thr Asp Pro Lys His Phe Glu Leu His Val Arg Ser
                85                  90                  95

Ser Val Glu Thr Ser Gly Ala Leu Lys Thr Pro Glu Ala Ala Lys Val
            100                 105                 110

Ser Ala Ser Gly Asn Gly Thr Asp Gly Pro Leu Phe Ser Ser Asp Val
        115                 120                 125

Glu Ser Ala Arg Leu Phe Pro Ser Ile Thr Ala Ala Glu Thr Arg Leu
    130                 135                 140

Pro Phe Leu Asp Gly Cys Phe Arg Pro Asn Thr Asp Gly Gly Ser Val
145                 150                 155                 160

Val Val Trp Ala Gly Gly Arg Arg Gln Gln Leu Gln Gln Gln
                165                 170                 175

Ser Leu Cys Ser Arg Gln Pro Ala Glu Arg Glu Glu Glu Ala Gly
            180                 185                 190

Ala Val Pro Gln Ala Glu Lys Ser Ala Val Phe Leu Pro Glu Ala Leu
        195                 200                 205

His Gln Glu Ala Lys Gly Phe Cys Leu Pro Leu Thr Ala Ser Leu Glu
    210                 215                 220

Asn Phe Thr Ala Ser Gly His Glu Arg Ser Leu His Pro Ser His Val
225                 230                 235                 240

Gly Ser Val Leu Pro Asn Asp Thr Thr Asp Leu Asn Glu Glu Arg Ser
                245                 250                 255

Phe Ala Gln Cys Met Pro Gly Met Asp Leu Ser Ala Ser Pro Leu Arg
            260                 265                 270

Met Asp Ala Arg Val Lys Glu Glu Leu Leu Leu His Phe Leu Asn Leu
        275                 280                 285

Ile Ser Ser Ser Pro Ser Ser Ser Ser Glu Val Gly Ala Ser Phe
    290                 295                 300

Gln Ser Asp Arg Asp Ala Ala Thr Glu Thr Glu Leu Val Thr Val Phe
305                 310                 315                 320
```

```
Val Arg Gly Glu Asp Ala Gly Val Asp Ala Asp Thr Asn Thr Arg Arg
                325                 330                 335

Arg Arg Arg Arg Glu Ala Ser Cys Lys Lys Pro Asp Ala Ile Gln His
            340                 345                 350

Glu Glu Ser Met Ala Met Thr Thr Gln Thr Ser Gly Asn Thr Asp Arg
        355                 360                 365

Ala Gln Leu Gly Arg Tyr Arg Gln Leu Pro Gly Tyr Thr Glu Ala Arg
    370                 375                 380

Arg Met Ala Gln Arg Met Ala Leu Glu Lys Val Arg Gln Gln Phe Cys
385                 390                 395                 400

Cys Ser Ala Glu

<210> SEQ ID NO 7
<211> LENGTH: 442
<212> TYPE: PRT
<213> ORGANISM: Trypanosoma cruzi

<400> SEQUENCE: 7

Met Met Arg Val Cys Arg Pro Gln Leu Leu Arg Val Ser Pro Leu Leu
1               5                   10                  15

Arg Val Trp Ala Ala Glu Glu Asp Asp Ala Asn Ala Pro Pro Thr Thr
            20                  25                  30

Phe Lys Asn Val Lys Pro Gly Arg Leu Leu Arg Leu Trp Arg Gln Ile
        35                  40                  45

Arg His Arg Ser Trp Ile Val Tyr Thr Trp Asp Glu Glu Trp Thr Ser
    50                  55                  60

Pro Gly Ser Glu Gly Tyr Leu His Gln Gln Arg Leu Glu Gln Val Cys
65                  70                  75                  80

Phe Ala Pro Leu Ser Ala Tyr Gly Met Val Pro Gly Ser Tyr Cys Asp
                85                  90                  95

Pro Leu Tyr Asn Thr Lys His Thr Ser Pro Phe Arg Trp His Val
            100                 105                 110

Ala Asn Thr Ser Ser Asp Ile Val Gly His Trp Tyr Met Glu Ala Asp
        115                 120                 125

Glu Ile Phe Arg Ile Lys Asp Trp Gln Pro Lys Asn Pro Asp Asp Pro
    130                 135                 140

Thr Glu Met Phe Pro Arg Pro Gln Gln Ile Leu Lys Trp Asp Glu
145                 150                 155                 160

Thr Val Asp Glu His Gly Asn Arg Thr Phe Arg Tyr Lys Tyr Arg Tyr
                165                 170                 175

Asp Phe Met Gly Pro Thr Gly Met Trp Glu Ala Tyr Pro Arg Tyr Pro
            180                 185                 190

Phe Ser His Ile Tyr Leu Asn Gly Gln Asp His His Gly Arg Ala Glu
        195                 200                 205

Gly Tyr Gly Phe Lys Gln Gly His Leu Leu Arg Cys Ser Glu Glu
    210                 215                 220

Glu Glu Val Leu Arg Arg Ile Met Glu Glu Asp Lys Glu Trp Glu
225                 230                 235                 240

Met Val Lys Arg Thr Glu Val Val Gln Glu Pro Trp Ser Tyr Pro Gly
                245                 250                 255

Lys Ile Arg Pro Gln Asp Phe Lys Gly Ala Val Glu Arg Ala Lys Ala
            260                 265                 270

Arg Phe Arg Glu Gln Ile Lys His Gly Lys Glu Thr Asp Pro Ser Glu
        275                 280                 285
```

```
Asp Pro Asp Tyr Asp Leu Val Gln Ala Gly Glu Phe Val Glu Pro Arg
    290                 295                 300

Asp Gly Pro Arg Ala Glu Trp Arg His Leu Trp Thr Ser Asn Arg Pro
305                 310                 315                 320

Lys Gly Glu Pro Leu Pro Tyr Gln Val Thr Phe Asn Asp Gly Ile Thr
                325                 330                 335

Phe Glu Asp Asn Glu Gly Arg Pro Pro Val His Pro Glu Ser His Tyr
            340                 345                 350

Glu Gln Thr Pro Lys Glu Ala Pro Tyr Lys Lys Tyr Glu Glu Gln Asp
        355                 360                 365

Thr Lys Glu Glu Glu Glu Gln Lys Arg Arg Lys Ser Ala Trp Asp
370                 375                 380

Gln Ser Phe Lys Glu Ser Ile Ala Lys Tyr Glu Glu Arg Tyr Gly Val
385                 390                 395                 400

Glu Ala Lys Lys Gly Asp Ser Asp Lys Lys Ser Ser Ser Asp Thr Gly
                405                 410                 415

Lys Ser Ser Gly Gly Asp Gly Ser Thr Pro Pro Ser Ser Ser
                420                 425                 430

Ser Ser His Glu Gly Gln Asp Gly Lys Lys
            435                 440

<210> SEQ ID NO 8
<211> LENGTH: 233
<212> TYPE: PRT
<213> ORGANISM: Trypanosoma cruzi

<400> SEQUENCE: 8

Met Leu Arg Arg Ala Val Asn Ile Ser Ile Ala Arg Gly Arg Met Ala
1               5                   10                  15

Leu Met Ser Tyr Ala Thr Leu Pro Asp Leu Leu Lys Pro Ser Gly Ala
                20                  25                  30

Pro Ala Glu Leu Pro Lys Leu Gly Phe Asn Trp Lys Asp Gly Cys Ala
            35                  40                  45

Pro Val Phe Ser Pro Arg Gln Met Glu Leu His Tyr Thr Lys His His
        50                  55                  60

Lys Ala Tyr Val Asp Lys Leu Asn Ala Leu Ala Gly Thr Thr Tyr Asp
65                  70                  75                  80

Gly Lys Ser Ile Glu Glu Ile Leu Ala Val Ala Asn Asp Ala Glu
                85                  90                  95

Lys Lys Gly Leu Phe Asn Gln Ala Ala Gln His Phe Asn His Thr Phe
            100                 105                 110

Tyr Phe Arg Cys Ile Thr Pro Asn Gly Lys Ala Met Pro Lys Ser Leu
        115                 120                 125

Glu Ser Ala Val Thr Ala Gln Phe Gly Ser Val Glu Gln Phe Lys Asp
    130                 135                 140

Ala Phe Val Gln Ala Gly Val Asn Asn Phe Gly Ser Gly Trp Thr Trp
145                 150                 155                 160

Leu Cys Val Asp Pro Ser Asn Lys Asn Gln Leu Val Ile Asp Asn Thr
                165                 170                 175

Ser Asn Ala Gly Cys Pro Leu Thr Lys Gly Leu Arg Pro Val Leu Ala
            180                 185                 190

Val Asp Val Trp Glu His Ala Tyr Tyr Lys Asp Phe Glu Asn Arg Arg
        195                 200                 205

Pro Asp Tyr Leu Lys Glu Ile Trp Ser Val Ile Asp Trp Glu Phe Val
    210                 215                 220
```

```
Ala Lys Met His Ala Gln Ala Ile Lys
225                 230

<210> SEQ ID NO 9
<211> LENGTH: 354
<212> TYPE: PRT
<213> ORGANISM: Trypanosoma cruzi

<400> SEQUENCE: 9

Met Asp Glu Asn Glu Gly Gly Trp Glu Glu Phe Ala Glu Glu Pro Gln
1               5                   10                  15

Gln Tyr Gly Glu Ala Glu Asp Ala Ala Asp Ile Tyr Ala Glu Glu Thr
            20                  25                  30

Leu Ala Thr Ala Gln Lys Ile Ala Ser Asp Asp Ala Leu Arg Phe
        35                  40                  45

Asp Ser Val Lys Glu Val Thr Leu Leu Leu Arg Ser Ala Tyr Met Ser
    50                  55                  60

Arg Met Leu Gln Lys Leu Gly Asp Tyr Ser Glu Gln Glu Val Val Lys
65                  70                  75                  80

Lys Thr Ile Leu Pro Glu Asp Pro Glu Tyr Gln Phe Val Ile Asp Ser
                85                  90                  95

Ser Thr Leu Val Leu Arg Ile Glu Val Glu Lys Ser Lys Ala Val Val
            100                 105                 110

Tyr Leu Arg Ala His Tyr Gly Gln Arg Phe Pro Glu Leu Ala Met Phe
        115                 120                 125

Phe Ser Asp Ser Val Leu Tyr Ala Arg Ile Val Arg Leu Ile Gln Asn
    130                 135                 140

Asn Met Asp Leu Ser Val Val Ile Asp Gln Leu Asp Glu Leu Ile Pro
145                 150                 155                 160

Ser Gln Leu Thr Ala Val Val Ile Ala Cys Ala Ser Thr Thr Ala Gly
                165                 170                 175

Arg Glu Leu Ser Glu Glu Glu Leu His Arg Val Val Glu Ala Cys Gln
            180                 185                 190

Glu Ile Asp Ile Leu Glu Ala Ala Lys Gln Thr Phe Leu Glu Tyr Ile
        195                 200                 205

Gln Arg Ser Met Pro Leu Ile Cys Pro Asn Leu Cys Ala Phe Leu Gly
    210                 215                 220

Thr Gly Ile Thr Ser Gln Leu Phe Ala Ile Ala Gly Gly Val Ser Ala
225                 230                 235                 240

Leu Ser Thr Met Asp Ser Thr Glu Leu Ala Arg Leu Gly Ser Lys Arg
                245                 250                 255

Ala Asp Ser Ser Gly Val Leu Ile Arg Thr Thr Gly Phe Leu Ser Asn
            260                 265                 270

Ser Asp Leu Val Val Asn His Pro Pro Gln Met Arg Pro Lys Ala Leu
        275                 280                 285

Arg Leu Val Ala Ser Thr Thr Ser Met Leu Ala Arg Ile Asp Ala Asn
    290                 295                 300

Arg Arg Ala Ser Ser Gln His Glu Gly Tyr Arg Gln Arg Glu Met Val
305                 310                 315                 320

Arg Leu Lys Met Leu Ser Trp Leu Asp Pro Pro Val Leu Arg Gly Ala
                325                 330                 335

Ala Asn Asn Thr Tyr Ala Arg Arg Gly Arg Lys Arg Pro Arg Arg Gln
            340                 345                 350

Thr Arg
```

<210> SEQ ID NO 10
<211> LENGTH: 146
<212> TYPE: PRT
<213> ORGANISM: Trypanosoma cruzi

<400> SEQUENCE: 10

Met Thr His Ser Thr Asp Leu Gln Trp Leu Val Arg Gln Asn Ser
1               5                   10                  15

Lys Phe Leu Gln Lys Arg Asn Gly Ile Arg Leu Ser Ser Asp Pro Phe
                20                  25                  30

Asn Asn Asn Ala Asn Trp Thr Lys Arg His Ala Gly Phe Leu Asn Thr
            35                  40                  45

Lys Ala Ala Val Val Lys Thr Lys Gly Asp Arg Ile Leu Val Thr Thr
50                  55                  60

Lys Asp Gly Lys Ala Gly Asn Lys Pro Lys Ser Met Tyr Lys Lys Ala
65                  70                  75                  80

Val Met Asp Ala Gly Val Glu Ala Ser Val Val Ser Lys Ala Val Ala
                85                  90                  95

Ala Val Arg Pro Asp Leu Ala Ser Ile Ala Ser Arg Arg Ala Arg Lys
            100                 105                 110

Met Ala Ser Thr Leu Glu His Met Lys Lys Val Arg Ala Ala Arg Lys
        115                 120                 125

Glu Arg Ser Ser Lys Ile Thr Phe Gln Arg Lys Ala Val Arg Pro Lys
    130                 135                 140

Arg His
145

<210> SEQ ID NO 11
<211> LENGTH: 525
<212> TYPE: PRT
<213> ORGANISM: Trypanosoma cruzi

<400> SEQUENCE: 11

Met Pro Pro Thr Ile His Arg Asn Leu Leu Ser Pro Glu Leu Val Gln
1               5                   10                  15

Trp Ala Leu Lys Ile Glu Lys Asp Ser Arg Leu Thr Ala Arg Gly Ala
                20                  25                  30

Leu Ala Val Met Ser Tyr Ala Lys Thr Gly Arg Ser Pro Leu Asp Lys
            35                  40                  45

Arg Ile Val Asp Thr Asp Val Arg Glu Asn Val Asp Trp Gly Lys
        50                  55                  60

Val Asn Met Lys Leu Ser Glu Glu Ser Phe Ala Arg Val Lys Lys Ile
65                  70                  75                  80

Ala Lys Glu Phe Leu Asp Thr Arg Glu His Leu Phe Val Val Asp Cys
                85                  90                  95

Phe Ala Gly His Asp Glu Arg Tyr Arg Leu Lys Val Arg Val Phe Thr
            100                 105                 110

Thr Arg Pro Tyr His Ala Leu Phe Met Arg Asp Met Leu Ile Val Pro
        115                 120                 125

Thr Pro Glu Glu Leu Ala Thr Phe Gly Glu Pro Asp Tyr Val Ile Tyr
    130                 135                 140

Asn Ala Gly Glu Cys Lys Ala Asp Pro Ser Ile Pro Gly Leu Thr Ser
145                 150                 155                 160

Thr Thr Cys Val Ala Leu Asn Phe Lys Thr Arg Glu Gln Val Ile Leu
                165                 170                 175

```
Gly Thr Glu Tyr Ala Gly Glu Met Lys Lys Gly Ile Leu Thr Val Met
            180                 185                 190

Phe Glu Leu Met Pro Arg Met Asn His Leu Cys Met His Ala Ser Ala
        195                 200                 205

Asn Val Gly Lys Gln Gly Asp Val Thr Val Phe Phe Gly Leu Ser Gly
    210                 215                 220

Thr Gly Lys Thr Thr Leu Ser Ala Asp Pro His Arg Asn Leu Ile Gly
225                 230                 235                 240

Asp Asp Glu His Val Trp Thr Asp Arg Gly Val Phe Asn Ile Glu Gly
                245                 250                 255

Gly Cys Tyr Ala Lys Ala Ile Gly Leu Asn Pro Lys Thr Glu Lys Asp
            260                 265                 270

Ile Tyr Asp Ala Val Arg Phe Gly Ala Val Ala Glu Asn Cys Val Leu
        275                 280                 285

Asp Lys Arg Thr Gly Glu Ile Asp Phe Tyr Asp Glu Ser Ile Cys Lys
    290                 295                 300

Asn Thr Arg Val Ala Tyr Pro Leu Ser His Ile Glu Gly Ala Leu Ser
305                 310                 315                 320

Lys Ala Ile Ala Gly His Pro Lys Asn Val Ile Phe Leu Thr Asn Asp
                325                 330                 335

Ala Phe Gly Val Met Pro Pro Val Ala Arg Leu Thr Ser Ala Gln Ala
            340                 345                 350

Met Phe Trp Phe Val Met Gly Tyr Thr Ala Asn Val Pro Gly Val Glu
        355                 360                 365

Ala Gly Gly Thr Arg Thr Ala Arg Pro Ile Phe Ser Ser Cys Phe Gly
    370                 375                 380

Gly Pro Phe Leu Val Arg His Ala Thr Phe Tyr Gly Glu Gln Leu Ala
385                 390                 395                 400

Glu Lys Met Gln Lys His Asn Ser Arg Val Trp Leu Leu Asn Thr Gly
                405                 410                 415

Tyr Ala Gly Gly Arg Ala Asp Arg Gly Ala Lys Arg Met Pro Leu Arg
            420                 425                 430

Val Thr Arg Ala Ile Ile Asp Ala Ile His Asp Gly Thr Leu Asp Arg
        435                 440                 445

Thr Glu Tyr Glu Glu Tyr Pro Gly Trp Gly Leu His Ile Pro Lys Tyr
    450                 455                 460

Val Ala Lys Val Pro Glu His Leu Leu Asn Pro Arg Lys Ala Trp Lys
465                 470                 475                 480

Asp Val Arg Gln Phe Asn Glu Thr Ser Lys Glu Leu Val Ala Met Phe
                485                 490                 495

Gln Glu Ser Phe Ser Ala Arg Phe Ala Ala Lys Ala Ser Gln Glu Met
            500                 505                 510

Lys Ser Ala Val Pro Arg Tyr Val Glu Phe Ala Arg Leu
            515                 520                 525

<210> SEQ ID NO 12
<211> LENGTH: 128
<212> TYPE: PRT
<213> ORGANISM: Trypanosoma cruzi

<400> SEQUENCE: 12

Met Gln Ile Phe Val Lys Thr Leu Thr Gly Lys Thr Ile Ala Leu Glu
1               5                   10                  15

Val Glu Ser Ser Asp Thr Ile Glu Asn Val Lys Ala Lys Ile Gln Asp
```

```
                   20                  25                  30

Lys Glu Gly Ile Pro Pro Asp Gln Gln Arg Leu Ile Phe Ala Gly Lys
                35                  40                  45

Gln Leu Glu Asp Gly Arg Thr Leu Ala Asp Tyr Asn Ile Gln Lys Glu
            50                  55                  60

Ser Thr Leu His Leu Val Leu Arg Leu Arg Gly Gly Val Met Glu Pro
65                  70                  75                  80

Thr Leu Glu Ala Leu Ala Lys Lys Tyr Asn Trp Glu Lys Lys Val Cys
                85                  90                  95

Arg Arg Cys Tyr Ala Arg Leu Pro Val Arg Ala Ser Asn Cys Arg Lys
            100                 105                 110

Lys Ala Cys Gly His Cys Ser Asn Leu Arg Met Lys Lys Lys Leu Arg
            115                 120                 125

<210> SEQ ID NO 13
<211> LENGTH: 323
<212> TYPE: PRT
<213> ORGANISM: Trypanosoma cruzi

<400> SEQUENCE: 13

Met Pro Ser Val Ser Glu Ala Lys Arg Glu Tyr Glu Arg Phe Asn
1               5                   10                  15

Gly Cys Leu Thr Lys Tyr Gly Arg Val Leu Phe Cys Leu Met Asp Asn
                20                  25                  30

Val Arg Ser Gln Gln Val His Asp Val Arg Arg Asp Leu Arg Gly Leu
            35                  40                  45

Gly Glu Leu Val Met Gly Lys Lys Thr Leu Gln Lys Lys Ile Val Glu
        50                  55                  60

Arg Arg Ala Glu Asp Lys Lys Ala Ser Ala Tyr Asp Lys Leu Leu Tyr
65                  70                  75                  80

Asn Thr Cys Ile Glu Lys Lys Leu Leu Cys Gly Asn Thr Ala Leu Ile
                85                  90                  95

Phe Thr Asn Glu Glu Ile Pro Val Ile Thr Ala Val Leu Asp Lys His
            100                 105                 110

Arg Val Gln Ala Pro Ala Arg Val Gly Ala Ile Ala Pro Cys Asp Val
        115                 120                 125

Ile Val Pro Ala Gly Asn Thr Gly Met Glu Pro Lys Ala Thr Ser Phe
        130                 135                 140

Phe Gln Ala Leu Asn Ile Ala Thr Lys Ile Ala Lys Gly Thr Val Glu
145                 150                 155                 160

Ile Val Ser Asp Lys Lys Val Leu Ser Val Gly Asp Arg Val Asp Asn
                165                 170                 175

Ser Thr Ala Thr Leu Leu Gln Lys Leu Asp Ile Ser Pro Phe Tyr Tyr
            180                 185                 190

Gln Val Glu Val Gln Ser Val Trp Asp Arg Gly Met Leu Phe Leu Arg
        195                 200                 205

Glu Asp Leu Ser Ile Thr Asp Asp Val Val Glu Lys Tyr Leu Leu Glu
    210                 215                 220

Gly Ile Ser Asn Val Ala Ala Leu Ser Leu Gly Ala Gly Ile Pro Thr
225                 230                 235                 240

Ala Ala Thr Leu Pro His Met Ile Met Asp Ala Phe Lys Thr Leu Leu
                245                 250                 255

Gly Ala Ser Val Ala Thr Glu Tyr Glu Phe Asp Glu Phe Asp Gly Lys
            260                 265                 270
```

```
Asn Leu Arg Lys Ala Ala Leu Glu Gly Asn Leu Gly Gly Gly Val Ala
        275                 280                 285

Asp Ala Ala Ala Ala Asp Thr Gly Ala Ala Ala Pro Ala Ala
    290                 295                 300

Ala Ala Glu Pro Glu Glu Glu Asp Asp Asp Asp Phe Gly Met Gly
305                 310                 315                 320

Ala Leu Phe

<210> SEQ ID NO 14
<211> LENGTH: 208
<212> TYPE: PRT
<213> ORGANISM: Trypanosoma cruzi

<400> SEQUENCE: 14

Met Gln Ala Arg Gly Thr Val Lys Val Gln Gly Asp Ala Asn Val Asp
1               5                   10                  15

Gly Lys Met Ser Thr Gly Gln His Pro His Gln His Leu Asn Ser
            20                  25                  30

Thr Gln Ala Asn Ala Thr Thr Thr Ala Leu Glu Tyr Arg Ala Met Asn
        35                  40                  45

Arg Pro Leu Tyr Arg Gly Pro Ile Ser His Asn Ile Ile Ser Glu Met
    50                  55                  60

Ala Glu Gly Phe Tyr Val Leu Ser Gly Gly Tyr Lys Lys Leu Phe Ile
65                  70                  75                  80

Pro Ser Lys Asp Val Tyr Ala Leu Met Gln Asn Val Gly Met His Leu
                85                  90                  95

Thr Glu Glu Glu Phe His Asp Ala Leu Arg Val Ile Gly Gln Ser Glu
            100                 105                 110

Pro Gln Asn Ala Asp Glu Leu Ser Phe Ser Asp Phe Leu Leu Met
        115                 120                 125

Thr Arg Glu Val Asp Asp Thr Met Ala Asp Glu Leu Arg Ser Ala Phe
130                 135                 140

Phe His Tyr Asp Lys His Lys Thr Gly Tyr Val Thr Arg Lys Gln Phe
145                 150                 155                 160

Thr Glu Leu Phe Ala Thr Leu Gly Glu Arg Ser Thr Pro Glu Glu Leu
                165                 170                 175

Glu Glu Leu Leu Ala Val Ala Glu Val Asp Glu Thr Asp Asp Lys Ile
            180                 185                 190

Asp Tyr Asn Arg Phe Val Asn Glu Leu Thr Ser Arg Val Asn Cys Met
        195                 200                 205

<210> SEQ ID NO 15
<211> LENGTH: 589
<212> TYPE: PRT
<213> ORGANISM: Trypanosoma cruzi

<400> SEQUENCE: 15

Met Ser Ala Glu Glu Ala Thr Gly Leu Glu Ala Ala Arg Lys Gln Lys
1               5                   10                  15

Ile His Asn Leu Lys Leu Lys Thr Ala Cys Leu Glu Asn Glu Leu
            20                  25                  30

Ile Gln Glu Leu His Val Ser Asp Trp Ser Glu Thr Gln Arg Gln Lys
        35                  40                  45

Leu Arg Gly Ala His Leu Lys Ala Glu Glu Leu Val Ala Ser Val Asp
    50                  55                  60

Val Gly Thr Lys Trp Asn Leu Thr Glu Ala Tyr Asp Leu Ala Lys Leu
```

-continued

```
             65                  70                  75                  80
        Met Arg Val Cys Gly Leu Glu Met Ser Gln Arg Glu Leu Tyr Arg Pro
                        85                  90                  95
        Glu Asp Lys Ala Gln Phe Met Asp Ile Ile Gly Val Lys Lys Val Leu
                       100                 105                 110
        Gln Asp Leu Lys Gln Asn Arg Asn Lys Thr Arg Val Val Ser Phe Thr
                       115                 120                 125
        Gln Met Ile Asp Asn Ala Ile Ala Lys Met Glu Lys Val Glu Glu Glu
                   130                 135                 140
        Leu Arg Arg Ser Gln Leu Asp Ala Thr Gln Leu Ala Gln Val Pro Thr
        145                 150                 155                 160
        Arg Thr Leu Lys Gln Ile Glu Asp Ile Met Asn Ala Thr Gln Ile Gln
                       165                 170                 175
        Asn Ala Leu Ala Ser Thr Asp Asp Gln Ile Lys Thr Gln Leu Ala Gln
                       180                 185                 190
        Leu Glu Lys Thr Asn Glu Ile Gln Asn Val Ala Met His Asp Gly Glu
                       195                 200                 205
        Met Gln Val Ala Glu Gln Met Trp Thr Lys Val Gln Leu Gln Glu
                   210                 215                 220
        Arg Leu Ile Asp Leu Ile Gln Asp Lys Phe Arg Leu Ile Thr Lys Cys
        225                 230                 235                 240
        Glu Glu Glu Asn Gln Pro Phe Lys Lys Ile Tyr Glu Val Gln Lys Gln
                       245                 250                 255
        Ala Asn Gln Glu Thr Ser Gln Met Lys Asp Ala Lys Arg Arg Leu Lys
                       260                 265                 270
        Gln Arg Cys Glu Thr Asp Leu Lys His Ile His Asp Ala Ile Gln Lys
                       275                 280                 285
        Ala Asp Leu Glu Asp Ala Glu Met Lys Arg His Ala Ala Asn Arg
                   290                 295                 300
        Glu Lys Ser Asp Gly Phe Val Arg Glu Asn Glu Arg Gln Glu Glu
        305                 310                 315                 320
        Ala Trp Asn Lys Ile Gln Asp Leu Glu Arg Gln Leu Gln Lys Leu Gly
                       325                 330                 335
        Thr Glu Arg Phe Glu Glu Val Lys Arg Arg Ile Glu Glu Val Asp Arg
                       340                 345                 350
        Glu Glu Lys Arg Arg Val Glu Tyr Ser Gln Phe Leu Glu Val Ala Ser
                       355                 360                 365
        Gln His Lys Lys Leu Leu Glu Leu Thr Val Tyr Asn Cys Asp Leu Ala
                   370                 375                 380
        Ile Arg Cys Thr Gly Leu Val Glu Glu Leu Val Ser Glu Gly Cys Ala
        385                 390                 395                 400
        Ala Val Lys Ala Arg His Asp Lys Thr Ser Gln Asp Leu Ala Ala Leu
                       405                 410                 415
        Arg Leu Glu Val His Lys Glu His Leu Glu Tyr Phe Arg Met Leu Tyr
                       420                 425                 430
        Leu Thr Leu Gly Ser Leu Ile Tyr Lys Lys Glu Lys Arg Met Glu Glu
                       435                 440                 445
        Ile Asp Arg Asn Ile Arg Thr Thr His Ile Gln Leu Glu Phe Cys Val
                   450                 455                 460
        Glu Thr Phe Asp Pro Asn Ala Lys Arg His Ala Asp Met Lys Lys Glu
        465                 470                 475                 480
        Leu Tyr Lys Leu Arg Gln Gly Val Glu Glu Glu Leu Ala Met Leu Lys
                       485                 490                 495
```

```
Glu Lys Gln Ala Lys Ala Leu Glu Asp Phe Lys Glu Ser Glu Ala
                500                 505                 510

Leu Asp Ala Ala Gly Ile Glu Phe Asn His Pro Val Asp Glu Asn Asn
            515                 520                 525

Glu Glu Val Leu Thr Arg Arg Ser Lys Met Val Glu Tyr Arg Ser His
530                 535                 540

Leu Ser Lys Gln Glu Glu Val Lys Ile Ala Ala Glu Arg Glu Ile
545                 550                 555                 560

Lys Arg Ala Arg Leu Leu Arg Thr Gly Gly Gly Ser Gly Glu Gln
                565                 570                 575

Pro Arg Ile Gly Asn Asn Thr Ala Pro Ala Arg Leu Glu
            580                 585

<210> SEQ ID NO 16
<211> LENGTH: 513
<212> TYPE: PRT
<213> ORGANISM: Trypanosoma cruzi

<400> SEQUENCE: 16

Met Pro Asn Arg Gln Ile Ile Gln Val Phe Glu Glu Tyr Gln Arg Ala
1               5                   10                  15

Arg Val Lys Phe Val Gln Thr Ile Ala Asp Leu Ala Ser Lys Pro Gln
                20                  25                  30

His Ile Glu Ala Leu Gln Gln Ala Gly Val Met Gln Leu Leu Arg Pro
            35                  40                  45

Leu Leu Leu Asp Ser Val Pro Ser Ile Gln Gln Ser Ala Ala Leu Ala
        50                  55                  60

Leu Gly Arg Leu Ala Asn Tyr Ser Glu Glu Leu Ala Glu Asn Val Val
65                  70                  75                  80

Ser Gly Asp Ile Leu Ala Gln Leu Val Tyr Ser Leu Ser Asp Gln Ser
                85                  90                  95

Arg Phe Tyr Lys Lys Ser Ala Ala Phe Val Leu Arg Ser Val Ala Arg
            100                 105                 110

His Ser Pro Gln Leu Ala Gln Ala Val Val Asp Ser Gln Ala Val Glu
        115                 120                 125

Ala Leu Val Gly Cys Leu Glu Glu Phe Asp Pro Thr Val Lys Glu Ser
    130                 135                 140

Ala Ala Trp Ala Leu Gly Tyr Val Ala Arg His Asn Ala Pro Leu Ala
145                 150                 155                 160

Gln Glu Val Val Asp Lys Gly Ala Ile Pro Pro Leu Val Leu Cys Val
                165                 170                 175

Gln Glu Pro Glu Leu Ser Leu Lys Arg Thr Ala Ala Ser Thr Leu Ser
            180                 185                 190

Asp Ile Ala Lys His Leu Pro Glu Leu Ala Gln Ala Val Val Asp Gln
        195                 200                 205

Asp Ala Val Thr His Leu Ala Pro Leu Ile Met Ser Asn Asp Ser Lys
    210                 215                 220

Leu Arg Arg Gln Val Cys Gln Cys Leu Ala Gln Ile Ser Lys His Ser
225                 230                 235                 240

Val Glu Leu Ala Glu Leu Val Val Glu Gly Glu Ile Phe Pro Lys Ile
                245                 250                 255

Phe Thr Leu Leu Lys Asp Ser Asp Glu Val Val Arg Lys Asn Ala Ala
            260                 265                 270

Thr Cys Ile Arg Glu Ile Ala Lys His Thr Pro Glu Leu Ala Gln Leu
```

-continued

```
                275                 280                 285
Val Val Asn Ala Gly Gly Val Gly Ala Leu Val Asp Tyr Thr Ser Glu
            290                 295                 300

Ser Arg Asp Ser Ala Arg Leu Pro Gly Ile Met Thr Leu Gly Phe Ile
305                 310                 315                 320

Ser Ala Phe Ser Glu Thr Leu Ala Leu Ala Val Ile Val Ser His Gly
                325                 330                 335

Ile Val Pro Leu Ala Asp Ala Leu Glu Lys Glu Pro Glu Asp His Ile
            340                 345                 350

Lys Ala Ala Ala Ala Trp Ser Leu Gly Gln Ile Gly Arg His Ser Ala
                355                 360                 365

Asp His Ala Lys Ala Val Ala Asp Cys Asn Val Leu Pro Arg Leu Leu
            370                 375                 380

Asp Val Tyr Leu Asn Pro Lys Ser Ser Glu Asp Leu Arg Met Lys Ser
385                 390                 395                 400

Lys Arg Ala Leu Lys Asn Ile Ile Gln Arg Cys Leu Gln Leu Pro Ala
                405                 410                 415

Leu Glu Pro Leu Leu His Pro Asp Ala Pro Gln Lys Val Leu Lys Tyr
            420                 425                 430

Val Cys Gly Gln Phe Ala Lys Val Leu Pro Thr Asp Ile Ala Ala Lys
            435                 440                 445

Arg Glu Phe Val Ala Asn Arg Gly Leu Ala Thr Val Gln Arg Ile His
450                 455                 460

Pro Glu Pro Gly Ser Lys Leu Ala Glu Tyr Ile Gln Ser Ile Asn Asn
465                 470                 475                 480

Cys Tyr Pro Pro Glu Ile Val Gln Tyr Tyr Ser Pro Gln Tyr Ala Gln
                485                 490                 495

Thr Phe Leu Glu Lys Ile Glu Asn Tyr His Val Gln Asn Val Gln Gln
            500                 505                 510

Ser

<210> SEQ ID NO 17
<211> LENGTH: 466
<212> TYPE: PRT
<213> ORGANISM: Trypanosoma cruzi

<400> SEQUENCE: 17

Met Ala Arg Pro Leu Ile Tyr Pro Ile Leu Ser Leu Val Ala Ala Ala
1               5                   10                  15

Thr Leu Val Thr Thr Ala Val Glu Ala Leu Tyr Val Val Pro Gln Gly
            20                  25                  30

Arg Leu Arg Glu Thr Gly Ser Gly Trp His Pro Cys Asp Pro Asp Val
        35                  40                  45

Pro Gln Trp Ser Gly Tyr Phe Asp Ile Pro Gly Arg Glu Gly Asp Lys
    50                  55                  60

His Tyr Phe Tyr Trp Ala Phe Gly Pro Arg Asn Gly Asn Pro Glu Ala
65                  70                  75                  80

Pro Val Leu Leu Trp Met Thr Gly Gly Pro Gly Cys Ser Ser Met Phe
                85                  90                  95

Ala Leu Leu Ala Glu Asn Gly Pro Cys Leu Val Asn Glu Thr Thr Gly
            100                 105                 110

Asp Ile Tyr Lys Asn Asn Tyr Ser Trp Asn Asn Glu Ala Tyr Val Ile
        115                 120                 125

Tyr Val Asp Gln Pro Ala Gly Val Gly Phe Ser Tyr Ala Glu Val Glu
```

-continued

```
            130                 135                 140
Asp Tyr Asp Ser Asn Glu Glu Val Ser Asp Met Tyr His Phe
145                 150                 155                 160

Leu Gln Ala Phe Phe Gly Ala His Gln Lys Leu Arg Lys Asn Lys Leu
                165                 170                 175

Phe Val Val Gly Glu Ser Tyr Gly Gly His Tyr Ala Pro Ala Thr Ala
                180                 185                 190

His Tyr Ile Asn Lys Ala Asn Arg Glu His Val Gly Leu Pro Ile Arg
                195                 200                 205

Leu Ala Gly Leu Ala Val Gly Asn Gly Leu Thr Asp Pro His Thr Gln
210                 215                 220

Tyr Ala Ala Tyr Pro Ser Leu Ala Trp Gly Trp Cys Arg Glu Lys Leu
225                 230                 235                 240

Gly Glu Pro Cys Val Ser Glu Gly Tyr Gln Gln Met Ser Ser Met
                245                 250                 255

Val Thr Pro Cys Gln Lys Ala Ile Glu Ile Cys Asn Ser Asp Asn Asn
                260                 265                 270

Phe Ile Ala Lys Ala Ala Cys Val Thr Ala Arg Val Leu Cys Asn Pro
                275                 280                 285

Ile Ile Gly Val Tyr Ser Ala Thr Gly Leu Asn Asn Tyr Asp Ile Arg
                290                 295                 300

Lys Pro Cys Ile Gly Thr Leu Cys Tyr Asn Phe Asp Ala Leu Asn Ala
305                 310                 315                 320

Phe Met Asn Arg Glu Asp Val Gln Ser Ser Leu Gly Ala Lys Arg Gln
                325                 330                 335

Val Trp Gln Ser Cys Asn Met Glu Val Asn Leu Met Phe Leu Met Asp
                340                 345                 350

Trp Phe Lys Asn Phe Asn Tyr Thr Val Pro Thr Leu Leu Glu Asp Gly
                355                 360                 365

Val Ser Val Met Ile Tyr Ala Gly Glu Met Asp Phe Ile Cys Asn Trp
                370                 375                 380

Ile Gly Asn Lys Gln Trp Thr Thr Ala Leu Asn Trp Pro Gly Lys Ala
385                 390                 395                 400

Val Phe Asn Ala Ala Pro Asp Glu Pro Phe Arg Ala Pro Asp Gly Thr
                405                 410                 415

Val Ala Gly Leu Val Arg Thr Ala Ala Ala Ser Thr Ser Asn Leu
                420                 425                 430

Thr Phe Val Gln Val Tyr Asn Ala Gly His Met Val Pro Met Asp Gln
                435                 440                 445

Pro Ala Ser Ala Phe Val Met Ile Ser Asn Phe Leu Gln Gly Arg Pro
450                 455                 460

Phe Asn
465
```

<210> SEQ ID NO 18
<211> LENGTH: 381
<212> TYPE: PRT
<213> ORGANISM: Trypanosoma cruzi

<400> SEQUENCE: 18

```
Met Ser Arg Asn Val Ala Ala Glu Glu Glu Trp Glu Asp Val Asp Ala
1               5                   10                  15

Pro Asn Glu Glu Asp Glu Glu Glu Asp Thr Thr Ile Asn Asn Ser
                20                  25                  30
```

Asp Val Met Met Arg Tyr Lys Lys Ala Ala Leu Trp Cys Asn Glu Thr
         35                  40                  45

Leu Gln Leu Leu Leu Asp Ala Thr Lys Pro Gly Ala Lys Val His Glu
 50                  55                  60

Leu Cys Lys Leu Gly Asp Glu Thr Val Ala Lys Lys Leu Lys Thr Met
65                  70                  75                  80

Phe Lys Gly Thr Glu Lys Gly Leu Ala Phe Pro Thr Cys Ile Ser Val
                 85                  90                  95

Asn Ser Cys Val Ala His Asn Ser Pro Ser Ala Asp Asp Glu Val Ala
             100                 105                 110

Ser Gln Glu Ile Gln Leu Gly Asp Val Val His Ile Asp Leu Gly Ile
         115                 120                 125

His Val Asp Gly Tyr Cys Ala Gln Val Ala His Thr Val Gln Val Thr
     130                 135                 140

Glu Asn Asn Glu Leu Ala Ala Asp Asp Ala Ser Lys Val Ile Ser
145                 150                 155                 160

Ala Thr Tyr Gly Ile Leu Asn Thr Ala Met Arg Lys Met Arg Pro Gly
                 165                 170                 175

Val Ser Val Tyr Glu Val Thr Glu Val Ile Glu Lys Ala Ala His
             180                 185                 190

Tyr Gly Val Thr Pro Val Asp Gly Val Leu Ser His Met Leu Lys Arg
         195                 200                 205

Tyr Ile Val Asp Ser Phe Arg Cys Val Pro Gln Arg Lys Val Ala Glu
     210                 215                 220

His Leu Val His Asp Tyr Thr Leu Glu Ala Gly Gln Val Trp Thr Leu
225                 230                 235                 240

Asp Ile Val Met Ser Ser Gly Lys Gly Lys Leu Lys Glu Arg Asp Val
                 245                 250                 255

Arg Pro Thr Val Tyr Lys Val Ala Leu Asp Ser Asn Tyr Thr Met Lys
             260                 265                 270

Met Glu Ser Ala Arg Glu Leu Gln Arg Glu Ile Glu Ala Lys Tyr Gln
         275                 280                 285

Thr Phe Pro Phe Ala Leu Arg Asn Leu Glu Thr Lys Arg Ala Arg Leu
     290                 295                 300

Gly Leu Ser Glu Met Leu Lys His Gly Ala Val Val Pro Tyr Pro Val
305                 310                 315                 320

Leu Tyr Glu Arg Asp Gly Glu Val Val Gly His Phe Lys Ile Thr Leu
                 325                 330                 335

Leu Ile Thr Ala Lys Lys Ile Glu Pro Val Thr Gly Leu Lys Pro Gln
             340                 345                 350

Lys Ala Pro Thr Leu Pro Ala Tyr Thr Asp Glu Leu Leu Leu Glu Ala
         355                 360                 365

Ser Lys Leu Pro Leu Thr Leu Glu Lys Lys Arg Lys Asn
     370                 375                 380

<210> SEQ ID NO 19
<211> LENGTH: 411
<212> TYPE: PRT
<213> ORGANISM: Trypanosoma cruzi

<400> SEQUENCE: 19

Met Ser Leu Thr Leu Trp Ser Gly Val Asn Pro Glu Asn Ala Arg Thr
1               5                   10                  15

His Lys Leu Leu Ala Ala Ala Ala Leu Ala Asn Val Ala Val Thr Leu
             20                  25                  30

```
Lys Ala Cys Glu Tyr Gly Arg Glu Asn Glu Thr Ala Glu Tyr Cys Arg
         35                  40                  45

Asn Cys Ser Pro Cys Gly Arg Tyr Pro Val Leu Gln Thr Glu Glu Gly
     50                  55                  60

Cys Val Phe Glu Ser Asn Ala Ile Leu Arg His Ile Ala Arg Leu Asp
 65                  70                  75                  80

Arg Ser Gly Gly Phe Leu Tyr Gly Arg Thr Pro Leu Glu Gly Ser Gln
                 85                  90                  95

Val Asp Met Trp Leu Asp Phe Ser Ala Thr Glu Leu Asp Ala Ala Ser
             100                 105                 110

Glu Pro Phe Val His His Ala Phe Arg Gly Glu Pro Leu Pro Ala Asn
         115                 120                 125

Ala Met Asp Arg Val His Glu Val Leu Arg Ala Leu Glu Ala Trp Leu
     130                 135                 140

Glu Thr Arg Thr Phe Leu Val Gly Glu Arg Met Thr Val Ala Asp Val
145                 150                 155                 160

Ala Val Ala Phe Ala Leu Gln Trp His Tyr Arg Leu Asn Gly Ala Glu
                 165                 170                 175

Gly Glu Ala Leu Thr Lys Lys Tyr Arg Asn Ala Tyr Arg Leu Tyr Asn
             180                 185                 190

Thr Val Met Gln Gln Pro Lys Thr Val Glu Val Leu Arg Ser Gln Gly
         195                 200                 205

Ala Thr Phe Gly Pro Val Lys Ala Glu Arg Lys Gly Lys Asp Ala Ala
     210                 215                 220

Ala Pro Ala Arg Ala Glu Lys Lys Pro Lys Ala Ala Ala Ala Ala Ala
225                 230                 235                 240

Asp Gly Ala Glu Glu Asp Glu Ala Pro Arg Glu Lys Lys Lys Pro
                 245                 250                 255

Asn Pro Leu Asp Glu Leu Pro Pro Ser Pro Phe Val Leu Asp Ala Phe
             260                 265                 270

Lys Arg Glu Tyr Ser Asn Thr Asp Thr Arg Thr Val Ala Ala Pro Tyr
         275                 280                 285

Phe Phe Gln His Tyr Asp Ala Ala Gly Tyr Thr Thr Phe Trp Cys Arg
     290                 295                 300

Tyr Lys Tyr Asn Glu Asp Asn Lys Met Gln Phe Met Thr Ala Asn Leu
305                 310                 315                 320

Ile Arg Gly Trp Phe Gln Arg Met Glu His Val Arg Lys Tyr Ala Phe
                 325                 330                 335

Gly Val Ala Leu Ile Ile Gly Glu Glu Arg Arg His Asp Ile Val Ala
             340                 345                 350

Leu Trp Val Phe Arg Gly Arg Met Pro Ala Ile Val Glu Asp Val
         355                 360                 365

Glu Asp Thr Glu Leu Phe Asp Trp Glu Glu Val Ala Asp Val Ala Ala
     370                 375                 380

Gln Arg Glu Arg Ile Thr Asp Tyr Leu Cys Trp Glu Gly Pro Thr Ile
385                 390                 395                 400

Pro Arg Pro Val Leu Glu Gly Arg Val Phe Lys
                 405                 410

<210> SEQ ID NO 20
<211> LENGTH: 982
<212> TYPE: PRT
<213> ORGANISM: Trypanosoma cruzi
```

<400> SEQUENCE: 20

```
Met Ser Gly Asp Gly Asp Ser Ser Leu Asp Pro Ser Ile Leu Val Val
 1               5                  10                  15

Glu Ala Arg Phe Asn Glu Ser Leu Gly Asn Gln Ser Val Ser Gly Gly
                20                  25                  30

Gly Gly Ser Glu Arg Trp Gln His His Glu Glu Lys Gln Gln Gln Gln
            35                  40                  45

Gln Gln Pro Leu Ser Leu Pro Pro Arg Ser Arg Gly Asp Val Asn Trp
        50                  55                  60

Asn Ala Ser Ser Ser Ser Pro Ser Thr Ile Glu Glu Ala Glu Gly
 65                  70                  75                  80

Gly Asp Gly Asp Arg Arg Thr Ala Asp Arg Arg Trp Ser Asp Asp Gly
                85                  90                  95

Ser Asn Ala Gly Asn Asp Arg Asp Gly Gly Ile Glu Thr Asn Glu Glu
            100                 105                 110

Asn Glu Asp Glu Ile Ala Glu Arg Val Leu Arg Ala Leu Arg Cys Lys
        115                 120                 125

Asp Met Leu Met Asp Glu Gln Ala Arg Lys Leu Gln Arg Arg Glu Met
    130                 135                 140

Glu Ala Arg Gln Leu Arg Arg Glu Leu Asp Glu Leu Arg Gly Glu Lys
145                 150                 155                 160

Gln Leu Leu Met Gln Gln Leu Arg Gly Phe Leu Asp Gly Ser Thr Pro
                165                 170                 175

Met Thr Thr Ala Ser Glu Thr Gly Pro Leu Lys Asp Ser Gly Gln Leu
            180                 185                 190

Tyr Pro Ser Met Leu Leu Gln Arg Ala Asp Ser Gln Leu Gln Asp Glu
        195                 200                 205

Arg Ala Glu Arg Gln Gln Asp Ala Arg His Phe Met Ala His Ile Glu
    210                 215                 220

Gln Leu Thr Ala Gln Leu Ala Glu Ala Gln His Glu Ala Arg Thr Arg
225                 230                 235                 240

Glu Ala Arg His Ala Gln Asp Leu Asp Thr Ile Gln Gln Glu Met Gln
                245                 250                 255

Glu Leu Ser Thr Val Val Asp Asp Met His Ala Thr Lys Ala Ala Leu
            260                 265                 270

Cys Arg Thr Gln Glu Gln Leu Ala Lys Ala Asn Glu Glu Lys Ala Gln
        275                 280                 285

Cys Gln Leu Glu Arg Asp Arg Leu Val Arg Ser Leu Gln Glu Ala Leu
    290                 295                 300

Arg Arg Glu Gly Ser Glu His Gln Arg Thr Leu Glu Arg Met Arg Ala
305                 310                 315                 320

Glu Ala Gly Ala Tyr Glu Arg Ala Lys Ala Ala Glu Ala Lys Cys
                325                 330                 335

Arg Arg Ala Glu Ala Glu Leu Lys Leu Ala Glu Glu Leu Arg Ala
        340                 345                 350

Leu Arg Ile Glu Met Gln Gln Leu Val Asp Glu Asn Ala Ala Leu Thr
    355                 360                 365

Leu Arg Met Glu Ser Ser Glu Gln Gln Leu Arg Ala Gln Lys Gln
        370                 375                 380

His Val Glu Glu Arg Ala Ala Glu Ala Glu Arg Arg Leu Gln
385                 390                 395                 400

Glu Glu Leu Asp Ala Lys Val Arg Glu Met Ala Gln Leu Arg Ser Thr
                405                 410                 415
```

```
Arg Asp Ala Gln Ser Gln Leu Leu Val Glu Glu Gly Arg His Ala
            420                 425                 430

Leu Phe Gln Ala Glu Val Glu Glu Cys Val Gln Ser Thr Arg Gln Leu
            435                 440                 445

Glu Glu Ala Leu Met Arg Cys Glu Arg Arg Cys Glu Ala Glu Glu
            450                 455                 460

Arg Glu Thr Arg Val Ala Ala Glu Arg Asp Ala Leu Arg Val Gln Leu
465                 470                 475                 480

Gln Arg Val Thr Ala Ala Ser Arg Gln Glu Leu Leu Glu Gln Gln
                485                 490                 495

Leu Thr Glu Glu Met Arg Ser Phe His Gln Ala Lys Leu Gln Gln Met
            500                 505                 510

Gln Gln Ala Ala Glu His Gln Arg Gln Ala Glu Arg Leu Glu Glu
            515                 520                 525

Lys Ser Glu Glu Ala Val Arg Glu Tyr Arg Thr Leu Gln Ala Leu Leu
530                 535                 540

Asp Ser Thr Gln Arg Gln Met Glu Glu Val Ala Gly Lys Leu His Glu
545                 550                 555                 560

Leu Arg Gln Gln Arg Met Ser Leu Glu Ser Met Leu Ala Glu Thr Gln
            565                 570                 575

Gln Glu Asn Asn Glu Cys Ala Ala Arg Glu Lys Asn Ala Ala Ala Gln
            580                 585                 590

Leu Asp Ala Ile Arg Ser Arg Leu Lys Gln Arg Glu Cys Ala Trp Arg
            595                 600                 605

Glu Leu Arg Ala Lys Met Gln Arg Leu Glu Glu Arg Glu Gln Arg Arg
610                 615                 620

Arg Leu Ala Glu Ala Ala Asp Ser Leu Leu Arg Met Arg Gln Asn His
625                 630                 635                 640

His Ser Gln Gly Lys Cys Lys Thr Lys Leu Gln Thr Cys Ile Arg Asp
            645                 650                 655

Lys Ile Ser Arg Ala Arg Leu Glu Glu Asn Leu Leu Asp Asn Ile Ala
            660                 665                 670

Gly Val Asp Val Asn Thr Thr Leu Ser Thr Lys Glu Pro Ser Ser Met
            675                 680                 685

Thr Ala Pro Pro Pro Pro Glu Thr Lys Arg Thr Pro Leu Arg Gly
            690                 695                 700

Pro Gln Leu Asp Ala Trp Gln Ala Lys Leu Gln Ala Leu Glu Ala Arg
705                 710                 715                 720

Asn Ala Asn Leu Glu Arg Gln Leu Ala Ser Arg Gln Ile Gly His Arg
            725                 730                 735

Ala Leu Val Glu Asp Arg Lys Ala Leu His Gln Gln Met His Thr Leu
            740                 745                 750

Gln Glu Thr Ala Gln Gly Leu Met Ser Ala Leu Glu Arg Gln His Arg
            755                 760                 765

Asp Ala Ile Lys His Leu Glu Glu Ala His Arg His Thr Leu Val
            770                 775                 780

Ala Cys Arg Glu Ala Ser Asp Ala Leu Ala Ser His Glu Ser Cys Val
785                 790                 795                 800
```

```
Arg Ser Gly Val Val Arg Val Ser Glu Leu Met Ala Phe Ile Arg
            805                 810                 815

Ala Leu Glu Ala Asn Ala Thr Leu Val Ala Arg His His Glu Arg Leu
            820                 825                 830

Gln Glu Ala Pro Val Gln Met Ala Asp Asp Asp Lys Glu Asn Met
            835                 840                 845

Leu Arg Ala Ala Cys Asp Asp Ile Thr Arg Asn Phe Leu Gly Val Glu
850                 855                 860

Gly Gly Trp Glu Ala Leu Leu Gln His Ser Leu Arg Thr Thr Ser Gly
865                 870                 875                 880

Arg Lys Ser Ser Arg Ala Asp Gly Gly Ser Leu Thr Ala Ala Met Arg
                885                 890                 895

Arg Arg Ile Arg Cys Phe Leu Met Asp Tyr Leu Gln Ala Gln Leu Leu
                900                 905                 910

Gly Lys Pro Ala Ala Val Leu Pro Ala Leu Arg Arg Gln Ser Gly
            915                 920                 925

Asn Lys Lys Lys Ala Leu Asn Val Ser Phe Ala Ala Ser Ser Asp Gly
            930                 935                 940

Ser Thr Glu Ser His Asp Asp Trp Asp Glu Glu Gln Glu Asn Cys Gly
945                 950                 955                 960

Glu Arg Pro Leu Val Glu Leu Leu Met Glu Arg Val Arg Cys Val Tyr
                965                 970                 975

Gly Asp Asp Thr Pro Tyr
            980

<210> SEQ ID NO 21
<211> LENGTH: 221
<212> TYPE: PRT
<213> ORGANISM: Trypanosoma cruzi

<400> SEQUENCE: 21

Met Pro Asn Leu Arg Glu Arg Leu Arg Gly Gln Gln Ser Ser Pro Pro
1               5                   10                  15

Gln Leu Ser Phe Leu Leu Phe Leu Leu Ser Thr Ala Leu Leu Ser Leu
                20                  25                  30

Thr Val Cys Leu Ile Gly Val Glu Ala Ala Thr Thr Val Gly Ser
            35                  40                  45

Gly Glu Lys Leu Cys Leu Arg Glu Val Val Pro Pro Gln Ser Arg Val
50                  55                  60

Thr Phe Gln Phe Gln Val Val Gly Gly Asn His Asp Ile Arg Ala
65                  70                  75                  80

Ser Val Ala Asp Gln Glu Gly His Ile Leu Lys Glu Trp Gly Glu Thr
                85                  90                  95

Ser Asp Gly Leu Tyr Glu Val Leu Ala Gln Ser Gly Thr Lys Ala Ile
            100                 105                 110

Val Ala Cys Leu Asp Asn Thr Tyr Ala His Tyr Thr Pro Lys Leu Ile
            115                 120                 125

Val Phe His Phe Arg Tyr His Val Asp Tyr Thr Ser Val Ala Lys Gln
            130                 135                 140

Ser Glu Leu Asp Pro Val Glu Arg Lys Val Glu His Ile Ser Ser Leu
145                 150                 155                 160
```

-continued

```
Met Arg Gln Val Glu Ser Leu Gln Met Leu Leu Arg Thr Gln Gln Lys
                165                 170                 175

Glu His Arg Ala Thr Val Glu Glu Ser Ser Glu Arg Leu Leu Ile Trp
            180                 185                 190

Ser Val Phe Gln Val Leu Thr Leu Val Ile Met Ser Cys Phe Gln Leu
        195                 200                 205

Tyr Phe Leu Lys Arg Phe Leu Glu Arg Lys Ser Phe Val
    210                 215                 220
```